(12) United States Patent
Bode et al.

(10) Patent No.: US 12,233,073 B2
(45) Date of Patent: Feb. 25, 2025

(54) SKIN CARE FORMULATIONS AND SKIN CANCER TREATMENT

(71) Applicant: Regents of the University of Minnesota, Minneapolis, MN (US)

(72) Inventors: Ann M. Bode, Cannon Falls, MN (US); Zigang Dong, Austin, MN (US); Eunmiri Roh, Austin, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 444 days.

(21) Appl. No.: 16/620,382

(22) PCT Filed: Jun. 8, 2018

(86) PCT No.: PCT/US2018/036720
§ 371 (c)(1),
(2) Date: Dec. 6, 2019

(87) PCT Pub. No.: WO2018/227129
PCT Pub. Date: Dec. 13, 2018

(65) Prior Publication Data
US 2020/0179404 A1 Jun. 11, 2020

Related U.S. Application Data

(60) Provisional application No. 62/517,257, filed on Jun. 9, 2017, provisional application No. 62/517,319, filed on Jun. 9, 2017.

(51) Int. Cl.
*A61K 35/04* (2006.01)
*A61K 9/00* (2006.01)
*A61K 31/573* (2006.01)
*A61K 31/58* (2006.01)
*A61P 35/04* (2006.01)
*A61K 45/06* (2006.01)

(52) U.S. Cl.
CPC .......... *A61K 31/573* (2013.01); *A61K 9/0014* (2013.01); *A61K 31/58* (2013.01); *A61P 35/04* (2018.01); *A61K 45/06* (2013.01)

(58) Field of Classification Search
CPC .... A61K 31/573; A61K 31/58; A61K 9/0014; A61K 45/06; A61P 35/04
See application file for complete search history.

(56) References Cited

U.S. PATENT DOCUMENTS

| | | | |
|---|---|---|---|
| 4,789,667 A | 12/1988 | Makino et al. | |
| 6,015,548 A | 1/2000 | Siddiqui | |
| 6,090,369 A | 7/2000 | Stewart | |
| H2043 H | 8/2002 | Deckner | |
| 7,915,243 B2 | 3/2011 | Puglia et al. | |
| 8,048,456 B2 | 11/2011 | Burke-Colvlin et al. | |
| 8,071,578 B2 | 12/2011 | Sefton | |
| 9,056,063 B2 | 6/2015 | Hanson | |
| 9,278,061 B2 | 3/2016 | Florence | |
| 9,937,119 B2 | 4/2018 | Mendoza et al. | |
| 10,105,357 B2 | 10/2018 | Chen et al. | |
| 10,500,152 B2 | 12/2019 | Gan et al. | |
| 2003/0027776 A1 | 2/2003 | Roschke | |
| 2006/0069055 A1* | 3/2006 | Dajee ...................... A61P 17/14 |
| | | | 514/44 R |
| 2006/0251598 A1 | 11/2006 | Ramirez et al. | |
| 2009/0247477 A1 | 10/2009 | Talalay et al. | |
| 2009/0258841 A1 | 10/2009 | Murphy | |
| 2011/0044920 A1 | 2/2011 | Hines et al. | |
| 2011/0064832 A1 | 3/2011 | Burke-Colvin et al. | |
| 2011/0269699 A1 | 11/2011 | Keegan et al. | |
| 2011/0319277 A1 | 12/2011 | Park et al. | |
| 2012/0015064 A1 | 1/2012 | Burke-Colvin et al. | |
| 2012/0128606 A1 | 5/2012 | Igiebor | |
| 2013/0315846 A1 | 11/2013 | Collier et al. | |
| 2014/0161746 A1 | 6/2014 | Ramirez et al. | |
| 2015/0045289 A1 | 2/2015 | West et al. | |
| 2015/0250709 A1 | 9/2015 | Gan et al. | |

(Continued)

FOREIGN PATENT DOCUMENTS

DE 2633556 A * 2/1977
DE 202015001779 U1 7/2015

(Continued)

OTHER PUBLICATIONS

Clement et al., The use of the hairless mouse to develop topical cytostatic combination chemotherapy, 1984, Clinical and Experimental Dermatology, vol. 9, pp. 127-138. (Year: 1984).*

Singal et al., Facial Basal Cell Carcinoma Treated with Topical 5% Imiquimod Cream with Dermoscopic Evaluation, Jun. 15, 2016, Journal of Cutaneous and Aesthetic Surgery, vol. 9 iss. 2, pp. 122-125. (Year: 2016).*

Misago et al., Sebaceous carcinoma in association with actinic keratosis: A report of two cases with an immunohistochemical study, Mar. 21, 2015, The Journal of Dermatology, vol. 42, pp. 616-620. (Year: 2015).*

(Continued)

*Primary Examiner* — Ali Soroush
(74) *Attorney, Agent, or Firm* — Shumaker & Sieffert, P.A.

(57) ABSTRACT

An example technique for treating a skin cancer condition includes administering a therapeutically effective amount of a p53-related protein kinase (PRPK) inhibitor to a patient having skin cancer or having a high risk of developing skin cancer. An example composition includes a therapeutically effective amount of a PRPK inhibitor for treating a skin cancer condition. An example composition includes a pharmaceutically effective amount of at least one anti-solar ultraviolet (anti-sUV) combination for preventing a skin cancer condition. The at least one anti-sUV combination is chosen from the combinations: avobenzone and octinoxate; octocrylene and zinc oxide; avobenzone, octocrylene, and titanium dioxide; or avobenzone, octocrylene, and zinc oxide.

20 Claims, 60 Drawing Sheets

(56) References Cited

U.S. PATENT DOCUMENTS

| | | | |
|---|---|---|---|
| 2015/0290121 | A1 | 10/2015 | Gurge |
| 2015/0313819 | A1 | 11/2015 | Edelson |
| 2015/0328098 | A1 | 11/2015 | Soroudi |
| 2016/0015813 | A1 | 6/2016 | Gan et al. |

FOREIGN PATENT DOCUMENTS

| | | | | |
|---|---|---|---|---|
| DE | 202014010806 U1 | 9/2016 | | |
| EP | 2266527 A2 | 12/2010 | | |
| EP | 2255781 B1 | 8/2012 | | |
| WO | 1991/007166 | 5/1991 | | |
| WO | 1997/046219 A1 | 12/1997 | | |
| WO | 2011/046771 | 4/2011 | | |
| WO | 2015/030702 A2 | 3/2015 | | |
| WO | 2016/062285 | 4/2016 | | |
| WO | WO-2016062285 A1 * | 4/2016 | ........... | A61K 31/085 |
| WO | 2016/090247 | 6/2016 | | |
| WO | 2016/090252 A1 | 6/2016 | | |

OTHER PUBLICATIONS

Atzmony et al., "Treatments for Cutaneous Lichen Planus: A Systematic Review and Meta-Analysis," American Journal of Clinical Dermatology, vol. 17, No. 1, Feb. 2016, 13 pp.

Berg et al., "Skin Cancer in Organ Transplant Recipients: Epidemiology, Pathogenesis, and Management," Journal of the American Academy of Dermatology, vol. 47, No. 1, Jul. 2002, 20 pp.

Brash et al., "Sunlight and Sunburn in Human Skin Cancer: p53, Apoptosis, and Tumor Promotion," Journal of Investigative Dermatology Symposium Proceedings., vol. 1, No. 2, Apr. 1996, 7 pp.

Edlund et al., "Data-Driven Unbiased Curation of the TP53 Tumor Suppressor Gene Mutation Database and Validation by Ultradeep Sequencing of Human Tumors," Proceedings of the National Academy of Sciences of the United States of America, vol. 109, No. 24, Jun. 2012, 6 pp.

Facchin et al., "Phosphorylation and activation of the atypical kinase p53-related protein kinase (PRPK) by Akt/PKB," Cellular and Molecular Life Sciences, vol. 64, Aug. 2007, 10 pp.

Ferrone et al., "Clinicopathological features of and risk factors for multiple primary melanomas," Journal of the American Medical Association (JAMA), vol. 294, No. 13, Oct. 2005, 8 pp.

Giles et al., "Multiple primary melanomas: an analysis of cancer registry data from Victoria and New South Wales," Melanoma Research, vol. 5, No. 6, Dec. 1995, 6 pp.

Hensler et al., "Inflammation and Skin Cancer: Old Pals Telling New Stories," Cancer Journal, vol. 19, No. 6, Nov./Dec. 2013, 8 pp.

Jemal et al., "Cancer statistics, 2010," CA Cancer J. Clin, vol. 60, No. 5, Sep./Oct. 2010, 24 pp.

Jung et al., "Myricetin Inhibits UVB-Induced Angiogenesis by Regulating PI-3 Kinase in vivo," Carcinogenesis, vol. 31, No. 5, May 2010, 7 pp.

Jung et al., "Myricetin Suppresses UVB-Induced Skin Cancer by Targeting Fyn," Cancer Research, vol. 68, No. 14, Jul. 2008, 9 pp.

Jung et al., "Myricetin suppresses UVB-induced wrinkle formation and MMP-9 expression by inhibiting Raf," Biochemical Pharmacology, vol. 79, No. 10, May 2010, 7 pp.

Jung et al., "Naringenin targets ERK2 and suppresses UVB-induced photoaging," Journal of Cellular Molecular Medicine, vol. 20, No. 5, May 2016, 11 pp.

Kim et al., "Novel TOPK inhibitor HI-TOPK-032 effectively suppresses colon cancer growth," Cancer Research, vol. /2, No. 12, Jun. 2012, 9 pp.

Lanigan et al., "Final report on the Safety Assessment of EDTA, Calcium Disodium EDTA, Diammonium EDTA, Dipotassium EDTA, Disodium EDTA, TEA-EDTA, Tetrasodium EDTA, Tripotassium EDTA, Trisodium Edta, Hedta, and Trisodium HEDTA," International Journal of Toxicolocy, vol. 21, No. 2, Suppl., Oct. 2002, 48 pp.

Lee et al., "5-Deoxykaempferol Plays a Potential Therapeutic Role by Targeting Multiple Signaling Pathways in Skin Cancer," Cancer Prevention Research, vol. 3, No. 4, Apr. 2010, 13 pp.

Lee et al., "Myricetin is a Novel Natural Inhibitor of Neoplastic Cell Transformation and MEK1," Carcinogenesis, vol. 28, No. 9, Sep. 2007, 10 pp.

Lim et al., "MLK3 is a Direct Target of Biochanin A, which Plays a Role in Solar UV-Induced COX-2 Expression in Human Keratinocytes," Biochemical Pharmacology, vol. 86, No. 7, Oct. 2013, 18 pp.

Lim et al., "The daidzein metabolite, 6,7,4'-Trihydroxyisoflavone, is a Novel Inhibitor of PKCalpha in Suppressing Solar UV-induced Matrix Metalloproteinase 1," International Journal of Molecular Sciences, vol. 15, No. 11, Nov. 2014, 14 pp.

Lu et al., "Tumorigenic Effect of Some Commonly Used Moisturizing Creams When Applied Topically to UVB-pretreated High-Risk-Mice," Journal of Investigative Dermatology, vol. 129, No. 2, Aug. 2008, 8 pp.

Luxen et al., "[Rocuronium and sugammadex in emergency medicine: requirements of a muscle relaxant for rapid sequence induction]," Der Anaesthesist, vol. 63, No. 4, Apr. 2014, 7 pp. (Translation provided for only the Abstract).

Marcil et al., "Risk of Developing a Subsequent Nonmelanoma Skin Cancer in Patients With a History of Nonmelanoma Skin Cancer: A Critical Review of the Literature and Meta-analysis," Archives of Dermatology, vol. 136, No. 12, Dec. 2000, 7 pp.

Marshall et al., "Research and development of aminosteroid neuromuscular blocking agents: past and future," European Journal of Anaesthesiology, vol. 12, Supplement 11, Aug. 1995, 6 pp.

McMeniman et al., "Risk factors in a cohort of patients with multiple primary melanoma," Australasian Journal of Dermatology, vol. 51, No. 4, Nov. 2010, 4 pp.

Missero et al., "Crosstalk among p53 family members in cutaneous carcinoma," Experimental Dermatology, vol. 23, No. 3, Mar. 2014, 4 pp.

Niendorf et al., "Cutaneous melanoma: family screening and genetic testing," Dermatologic Therapy, vol. 19, No. 1, Jan. 2006, 8 pp.

Rhodes et al., "Risk factors for cutaneous melanoma, A practical method for recognizing predisposed individuals," Journal of the American Medical Association (JAMA), vol. 258, No. 21, Dec. 1987, 9 pp.

Roh et al., "Molecular Mechanisms of Green Tea Polyphenols with Protective Effects against Skin Photoaging," Critical Reviews in Food Science and Nutrition, vol. 57, No. 8, accepted author version posted online Jun. 2015, published online Mar. 2017, published May 2017, 7 pp.

Yokogawa et al., "Imiquimod attenuates the growth of UVB-induced SCC in mice through Th1/TH17 cells," Molecular Carcinogenesis, vol. 52, No. 10, Oct. 2013, 17 pp.

Zhu et al., "Bidirectional signals transduced by TOPK-ERK interaction increase tumorigenesis of HCT116 colorectal cancer cells," Gastroenterology, vol. 133, No. 1, Jul. 2007, 13 pp.

Zykova et al., "The T-LAK Cell-originated Protein Kinase Signal Pathway Promotes Colorectal Cancer Metastasis," EbioMedicine, vol. 18, 2017, 10 pp.

International Preliminary Report on Patentability from International Application No. PCT/US2018/036720, mailed Dec. 19, 2019, 7 pp.

International Search Report and Written Opinion from International Application No. PCT/US2018/036720, mailed Sep. 7, 2018, 9 pp.

* cited by examiner

Rocuronium bromide

Betamethasone 17-valerate

Group 5

Group 6

Group 8

Group 7

SKIN CARE FORMULATIONS AND SKIN CANCER TREATMENT

This application is a National Stage application under 35 U.S.C. § 371 of PCT Application No. PCT/US2018/036720, entitled "SKIN CARE FORMULATIONS AND SKIN CANCER TREATMENT" and filed on Jun. 8, 2018, which claims the benefit of U.S. Provisional Patent Application No. 62/517,319, titled "SKIN CANCER TREATMENT", filed Jun. 9, 2017 and U.S. Provisional Patent Application No. 62/517,257, titled "SKIN CARE FORMULATIONS", filed Jun. 9, 2017. The entire contents of application Nos. PCT/US2018/036720, U.S. 62/517,319 and U.S. 62/517,257 are incorporated herein by reference.

GOVERNMENT RIGHTS

This invention was made with government support under Grant No. 2P01CA027502-28A2 awarded by the National Institutes of Health. The government has certain rights in the invention.

TECHNICAL FIELD

This disclosure relates to skin care formulations and skin cancer treatment, and in particular, to anticancer techniques and compositions, to sunscreen and sunblock skin care formulations, and to noncarcinogenic skin case formulations.

BACKGROUND

Solar ultraviolet (sUV) light (i.e., sunlight) is an environmental carcinogen that may result in inflammation and skin cancer development, which is the most common cancer worldwide. One out of three new cancers is a skin cancer, making skin cancer the most common malignancy worldwide. Approximately 4.5 million cases of non-melanoma skin cancer (NMSC) occur annually. As incidence rates for NMSC continue to rise, an increasing and substantial impact on morbidity and health care costs occur and account for significant costs in skin cancer treatment. In particular, the incidence of non-melanoma cutaneous squamous cell carcinoma (cSCC) increases every year. Basal cell carcinomas (BCCs) rarely metastasize, whereas some cSCCs metastasize to regional lymph nodes or other distant sites accounting for ~15-20% of skin cancer deaths. Reducing the incidence of potentially dangerous cSCC skin cancers would not only reduce their potentially severe morbidity and mortality, but also dramatically reduce the multibillion-dollar costs typically associated with surgical and medical treatments required for non-melanoma skin cancers (NMSC) for affected individuals. Actinic keratosis (AK) acts as a precursor to cSCC and is a premalignant skin lesion characterized by proliferation of atypical keratinocytes confined to the epidermis induced by sUV. Although surgery may provide an effective treatment against early-stage non-melanoma skin cancer, chronic solar ultraviolet (sUV)-induced cutaneous squamous cell carcinoma (cSCC) can recur locally and may be characterized by invasion and metastasis. Skin care formulations may be used to maintain skin health, or to prevent or treat skin conditions. For example, moisturizing creams and ointments may be used for the prevention and treatment of dry skin. Sunscreen or sunblock may be used to reduce or prevent sUV wavelengths from penetrating skin.

SUMMARY

The disclosure describes techniques and compositions for treating a skin cancer condition. In some embodiments, a technique for treating a skin cancer condition includes administering a therapeutically effective amount of a p53-related protein kinase (PRPK) inhibitor to a patient having skin cancer or having a high risk of developing skin cancer.

In some embodiments, a composition includes a therapeutically effective amount of a PRPK inhibitor for treating a skin cancer condition. The PRPK inhibitor may include one or both of rocuronium bromide or betamethasone 17-valerate.

In some embodiments, the disclosure describes a composition including a pharmaceutically effective amount of at least one anti-solar ultraviolet (anti-sUV) combination for preventing a skin cancer condition. The at least one anti-sUV combination is chosen from the combinations: avobenzone and octinoxate; octocrylene and zinc oxide; avobenzone, octocrylene, and titanium dioxide; or avobenzone, octocrylene, and zinc oxide.

The details of one or more examples are set forth in the accompanying drawings and the description below. Other features, objects, and advantages will be apparent from the description and drawings, and from the claims.

DETAILED DESCRIPTION

Figure 1:
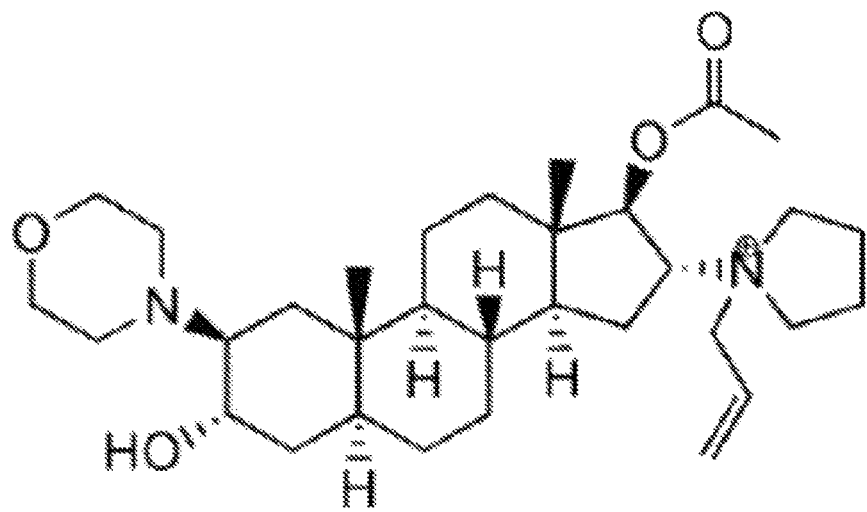
FIG. 1 is a conceptual and schematic diagram illustrating the molecular structure of rocuronium bromide.

The disclosure describes techniques and compositions for treating skin cancer conditions. While cancer may occur in healthy individuals, high-risk patients (for example, immunosuppressed organ transplant patients, HIV, cancer patients and other persons with compromised or deficient immune systems) may have a higher susceptibility to cancer, including skin cancer. Skin cancer may result from exposure to solar ultraviolet (sUV) or solar simulated light (SSL) wavelengths. SSL is light that simulates the effect of sUV exposure, for example, by including wavelengths or wavelength bands included in sUV. In this disclosure, the term sUV includes sUV and SSL wavelengths.

The T-LAK cell-originated protein kinase (TOPK) is a serine-threonine kinase that is a member of the mitogen-activated protein kinase kinase (MAPKK) family and is involved in many cellular functions, including tumor development, growth, apoptosis and inflammation. TOPK is highly expressed in many cancers. The p53-related protein kinase (PRPK), which is downstream of TOPK, is overexpressed in skin cancer and is a critical player in skin cancer development.

Without being bound by theory, PRPK is a downstream kinase of T-LAK cell-originated protein kinase (TOPK), a tumor promoter involved in sUV-induced skin carcinogenesis. Knockout of TOPK may inhibit PRPK phosphorylation and confer resistance to sUV-induced skin cancer development. TOPK-dependent PRPK signaling may be attenuated by PRPK inhibitors, for example, rocuronium bromide or betamethasone 17-valerate. Topical application of either compound may attenuate SSL-induced epidermal hyperplasia, neovascularization and cSCC development in Skh: hairless-1 mice by inhibiting PRPK activation, and expression of COX-2, cyclin D1 and MMP-9.

Rocuronium bromide and betamethasone 17-valerate are FDA-approved drugs for other applications. Rocuronium bromide is a substitute for succinylcholine as a neuromuscular blockade during rapid sequence induction (RSI) as long as sugammadex is available for reversal during surgery or mechanical ventilation. It acts by competing for cholinergic receptors at the motor end-plate. This action is antagonized by acetylcholinesterase inhibitors, such as neostigmine and edrophonium. Betamethasone 17-valerate is indicated for the relief of the inflammatory and pruritic anifestations of corticosteroid-responsive dermatoses.

As discussed elsewhere in the disclosure, knocking out TOPK expression completely blocked sUV-induced skin cancer development in an SCC mouse model. TOPK is highly expressed in AKs, SCCs, and BCCs compared to normal tissues. Phosphorylated and total TOPK protein levels in SCC metastasized to skin or lymph nodes are significantly higher compared to human SCC primary tumors.

TOPK directly binds to PRPK and strongly phosphorylates Ser250, a site that is important for PRPK activity. PRPK is highly phosphorylated in AKs and SCCs compared to normal human skin, and phosphorylated PRPK is absent in TOPK$^{-/-}$ (knockout) mice exposed to chronic SSL compared with wild-type mice. SSL exposure increases the expression of phosphorylated and total PRPK and TOPK in a time dependent manner.

Knocking down PRPK (shPRPK) expression in A431 cells significantly decreases colony formation compared with shMock cells. Phosphorylated PRPK levels in skin from TOPK−/− (knockout) mice are lower compared with SKH-1 TOPK+/+ (wildtype) mice stimulated with chronic or acute sUV irradiation.

Computer models for rocuronium bromide and betamethasone 17-valerate reveal the interaction of each drug with PRPK. Computer models indicated that rocuronium bromide fits into the ATP binding site of PRPK with close contacts at Val147, Val158, Ile116 and Leu169 residues. A hydrogen bond is observed between rocuronium bromide and Ile116. Betamethasone 17-valerate also docks into the ATP binding site of PRPK with close contacts at the Val47, Val58, Ile116, Arg123, and Ile182 residues. Betamethasone 17-valerate forms hydrogen bonds with Ile116 and Arg123.

Inflammation essentially contributes to tumor development and progression and metastasis often arises in acute and chronic inflammatory skin conditions and increased epidermal thickness is a sign of sUV-induced inflammatory responses. PRPK phosphorylation is induced by sUV as a potent stimulator of skin inflammation. Topical treatment with rocuronium bromide or betamethasone 17-valerate treats inflammation, and reduces both tumor volume and tumor number. Thus, PRPK inhibitors, for example, rocuronium bromide or betamethasone 17-valerate, or other PRPK inhibitors, may be used to prevent or treat skin cancer.

Figure 2:
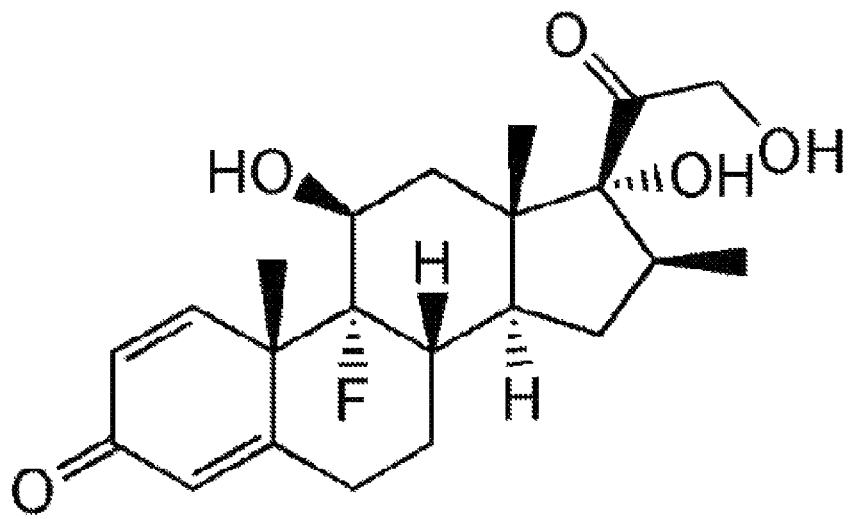
FIG. 2 is a conceptual and schematic diagram illustrating the molecular structure of betamethasone 17-valerate.

In some embodiments, a technique for treating a skin cancer condition includes administering a therapeutically effective amount of a p53-related protein kinase (PRPK) inhibitor to a patient having skin cancer. In some embodiments, a composition includes a therapeutically effective amount of a PRPK inhibitor for treating a skin cancer condition. The PRPK inhibitor may include one or both of rocuronium bromide or betamethasone 17-valerate. FIG. 1 is a conceptual and schematic diagram illustrating the molecular structure of rocuronium bromide. FIG. 2 is a conceptual and schematic diagram illustrating the molecular structure of betamethasone 17-valerate.

In some embodiments, a composition may include a therapeutically effective amount of a PRPK inhibitor for treating a skin cancer condition. For example, the skin cancer condition may include one or more of actinic keratosis, squamous cell carcinoma, or basal cell carcinoma. The PRPK inhibitor may include one or more of a steroid, a steroid derivative, a corticosteroid, or a gonane derivative. In some embodiments, the PRPK inhibitor comprises one or both of rocuronium bromide or betamethasone 17-valerate, or respective derivatives thereof. A derivative of a scaffold is a structure formed by replacing one or more molecules of the scaffold with predetermined functional groups, atoms, or molecules. For example, one or more sites of a scaffold may be substituted with one or more of H, CH$_3$, OH, Cl, NH$_2$, or another predetermined group or atom. The substitution may be in one or more of a base ring, a core structure, a side group, or a side chain of the scaffold. Thus, the term derivative includes structural analogs.

For example, betamethasone analogs may include one or more of prednisolone, methylprednisolone, budesonide, or compounds having one of the following structures:

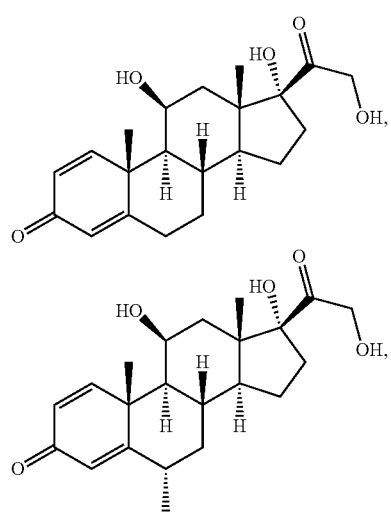

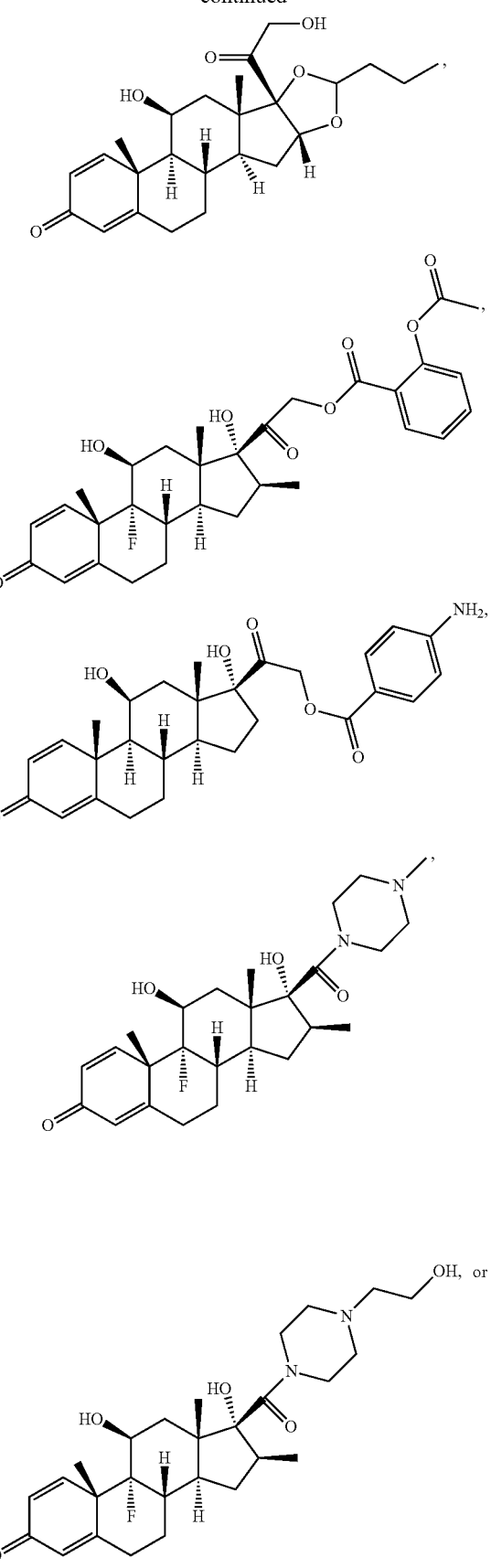

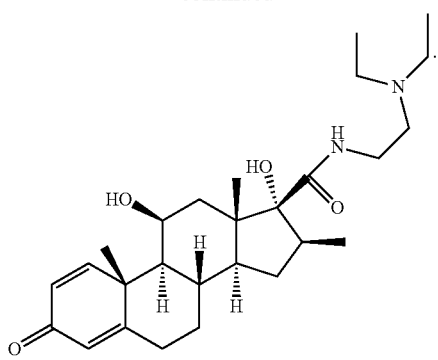
For example, rocuronium analogs may include one or more of vecuronium bromide, pipercurium bromide, or compounds having one of the following structures:
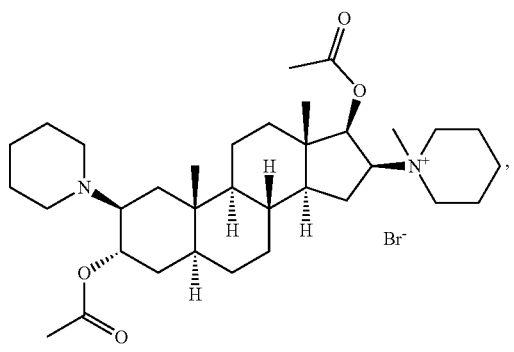
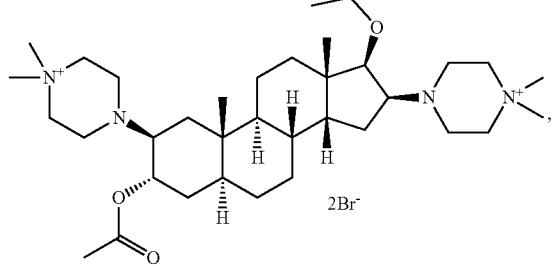
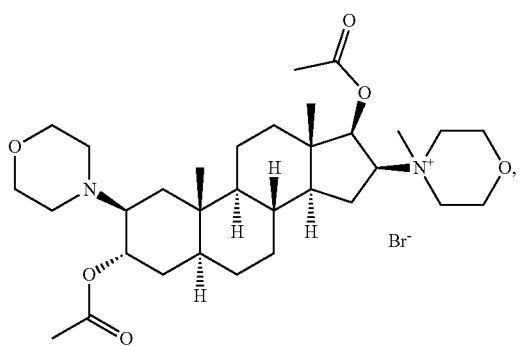
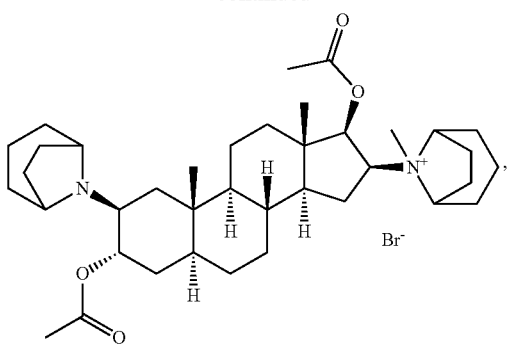
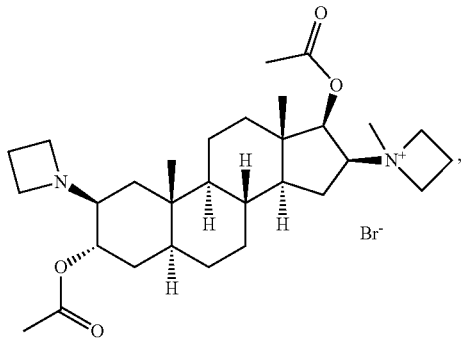
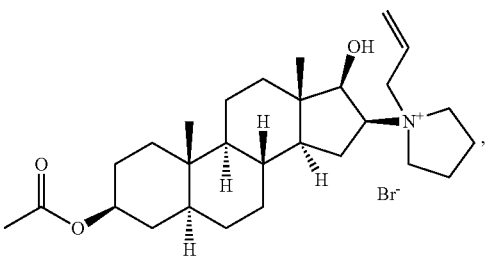
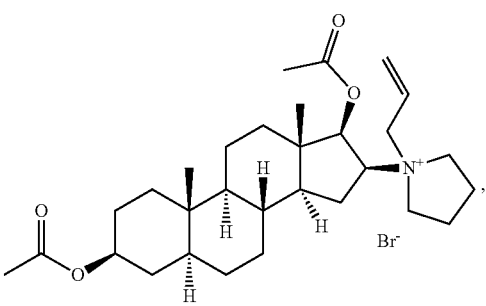

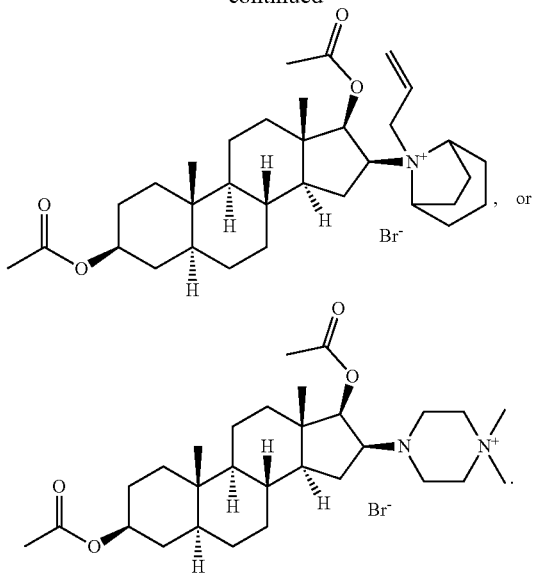

In some embodiments, the PRPK inhibitor includes at least one compound having the structure:

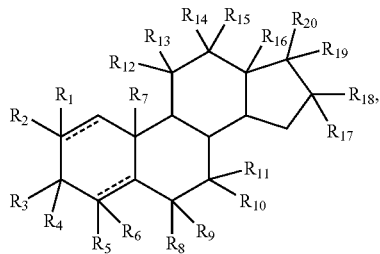

For example, any of $R_1$ to $R_{16}$=any of H, halo, hydroxy, substituted hydroxy, amino, substituted (acyl, alkyl, aralkyl, heteroaryl, cycloalkyl, aryl) amino, or carbonyl; any of $R_{17}$ or $R_{18}$=any of H, halo, hydroxy, substituted hydroxy, amino, substituted (acyl, alkyl, aralkyl, heteroaryl, cycloalkyl, aryl) amino, or quaternary ammonium group; any of $R_{19}$ or $R_{20}$=H, halo, hydroxy, substituted hydroxy, amino, or substituted (acyl, alkyl, aralkyl, heteroaryl, cycloalkyl, aryl) amino, or

wherein Q=H, allyl, substituted alkyl, aryl, substituted aryl, heteroaryl, substituted heteroaryl, hydroxy, substituted hydroxy, amino, substituted (acyl, alkyl, aralkyl, heteroaryl, cycloalkyl, aryl) amino, alkanol, alkenyl, or substituted alkenyl.

In some embodiments, each of $R_2$, $R_4$, $R_5$, $R_6$, $R_7$, $R_8$, $R_9$, $R_{10}$, $R_{11}$, $R_{12}$, $R_{14}$, $R_{15}$, and $R_{18}$=H, any of $R_1$, $R_3$, $R_7$, $R_{13}$, $R_{16}$, $R_{17}$, or $R_{20}$=any of H, allyl, substituted alkyl, aryl, substituted aryl, heteroaryl, substituted heteroaryl, sulfonyl, halo, hydroxy, substituted hydroxy, amino, dialkylamino, substituted (acyl, alkyl, aralkyl, heteroaryl, cycloalkyl, aryl) amino, carbonyl, substituted quarternary amino, O-glycosylated, alkenyl, substituted alkenyl, alkynyl, or substituted alkynyl, and

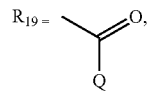

wherein Q=H, allyl, substituted alkyl, aryl, substituted aryl, heteroaryl, substituted heteroaryl, hydroxy, substituted hydroxy, amino, substituted (acyl, alkyl, aralkyl, heteroaryl, cycloalkyl, aryl) amino, alkanol, alkenyl, or substituted alkenyl.

In some embodiments, suitable salts of the PRPK inhibitors may be used, for example, a salt of one or more PRPK inhibitors and one or more of cations or anions. The cation may include one or more of aluminum, arginine, benzathine, calcium, chloroprocaine, choline, diethanolamine, ethanolamine, ethylenediamine, histidine, lithium, lysine, magnesium, meglumine, potassium, procaine, sodium, triethylamine, or zinc, or any other suitable cation. The anion may include one or more of acetate, aspartate, benzenesulfonate, benzoate, besylate, bicarbonate, bitartrate, bromide, camsylate, carbonate, chloride, citrate, decanoate, edetate, estolate, esylate, fumarate, gluceptate, gluconate, glutamate, glycolate, glycollylarsanilate, hexanoate, hexylresorcinate, hydrabamine, hydroxynaphthoate, iodide, isethionate, isethionate, lactate, lactobionate, malate, maleate, mandelate, mesylate, methylbromide, methylnitrate, methylsulfate, mucate, napsylate, nitrate, octanoate, oleate, pamoate, pantothenate, phosphate, polygalacturonate, propionate, salicylate, stearate, subacetate, succinate, sulfate, tartrate, teoclate, tosylate, or triethiodide, or any other suitable anion.

The composition may include any concentration of the PRPK inhibitor that may be provide a therapeutically effective amount of the PRPK inhibitor. For example, the composition may include 0.01%, 0.1%, 1%, 2%, 5%, or 10% (weight/weight) of the PRPK inhibitor. In some examples, different concentrations of different PRPK inhibitors may be used. For example, the composition may include a first concentration of a first PRPK inhibitor, for example, rocuronium bromide, or an analog, and a second concentration of a second PRPK analog, for example, betamethasone 17-valerate, or an analog.

In some embodiments, the composition may include a pharmaceutically acceptable carrier. For example, the pharmaceutically acceptable carrier may include one or more of a cream, a lotion, a spray, a gel, an ointment, a paste, a solution, a suspension, an emulsion, a powder, a liquid, or a solid. In some embodiments, a formulation may include a composition according to the disclosure, and the formulation may be a topical, injectable, parenteral, or oral formulation. For example, a topical formulation may include a composition according to the disclosure. In some embodiments, forms of administering the PRK inhibitor may include impregnated or coated gauzes, bandages, or transdermal patches.

In some embodiments, the topical formulation may include a sunscreen or a sunblock composition, for example, sunscreen or sunblock compositions described elsewhere in the disclosure. For example, the formulation may include one or more components that reduce or block sUV wavelengths from penetrating skin. In some embodiments, the topical formulation may include a noncarcinogenic composition, for example, noncarcinogenic compositions as described elsewhere in the disclosure.

The disclosure describes example techniques for treating a skin cancer condition. In some embodiments, a technique for treating a skin cancer condition includes administering a therapeutically effective amount of a p53-related protein kinase (PRPK) inhibitor to a patient having skin cancer. For example, the skin cancer condition may include one or more of actinic keratosis, squamous cell carcinoma, or basal cell carcinoma. The skin cancer condition may be associated with T-LAK cell-originated protein kinase (TOPK)-dependent PRPK phosphorylation.

In some embodiments, the technique may further include comparing the concentration of phosphorylated PRPK (p-PRPK) in a first biological sample of the patient obtained prior to the administration of the PRPK inhibitor and in a second biological sample of the patient obtained after the administration of the PRPK inhibitor. A clinician may monitor the progress of the treatment and the status of the skin cancer condition based on the comparison. For example, a lower concentration of p-PRPK in the second biological sample compared to the concentration of p-PRPK in the first biological sample is indicative of inhibition of PRPK phosphorylation by the PRPK inhibitor.

In some embodiments, the example technique may further include adjusting a dosage of the PRPK inhibitor administered to the patient based on the comparison. For example, the clinician may adjust the dosage of the PRPK inhibitor in response to the comparison, by increasing the dosage if the comparison is indicative of low or insufficient inhibition, and by maintaining or reducing the dosage if the comparison is indicative of sufficient inhibition of PRPK to advance the treatment of the skin cancer condition.

The dosage may be measured in terms of weight of PRPK inhibitor per unit weight of the patient, or in terms of weight or amount of PRPK inhibitor administered per predetermined treatment period. For example, the patient may be administered at least 0.1 mg/day, 1 mg/day, 5 mg/day, 10 mg/day, 20 mg/day, 50 mg/day, or 100 mg/day of the PRPK inhibitor. In some embodiments, the dosage may be measured in terms of amount of PRPK inhibitor applied per area of skin. For example, the patient may be administered at least 0.001 mg/sq. cm, 0.05 mg/sq. cm, 0.1 mg/sq. cm, 0.2 mg/sq. cm, 0.5 mg/sq. cm, or 1 mg/sq. cm per day.

The PRPK inhibitor may be delivered via a pharmaceutically acceptable carrier. Thus, in some embodiments, administering the PRPK inhibitor may include administering a pharmaceutically acceptable carrier including the PRPK inhibitor to the patient. For example, the pharmaceutically acceptable carrier may include a topical formulation including the PRPK inhibitor.

The terms treat, treating, or treatment in this disclosure refers to reducing the conditions or symptoms associated with a disease, or effects of the disease. For example, treatment may refer to partial, substantially complete, or complete reduction in conditions or symptoms, for example, inflammation, number, and volume of tumors, discomfort, pain, itching, or other symptoms or conditions. Treatment may not necessarily refer to a cure or complete abatement of the disease, or conditions or symptoms associated with the disease.

Other treatments or regimes may be used in addition to administering the PRPK inhibitor. For example, in some embodiments, the technique includes administering at least another treatment comprising one or more of chemotherapy, immunotherapy, radiation therapy, DNA therapy, RNA therapy, nanotherapy, adjuvant therapy, viral therapy, photodynamic therapy, electrocautery, laser therapy, or surgery.

As discussed elsewhere in the disclosure, administering the PRPK inhibitor may provide a therapeutic effect. For example, the therapeutic effect may include one or more of a reduction or a stability in one or more of an average volume of lesions, an average number of lesions, an average volume of tumors, an average number of tumors, or partial remission, complete remission, or metastasis.

In some aspects, the present disclosure describes compositions that can be used as, for example, a component in a skin care formulation, or as a skin care formulation. In some embodiments, the skin care formulation may be a sunscreen formulation or a sunblock formulation. In some examples, the compositions or skin care formulations may additionally include one or more PRPK inhibitors, for example, as described elsewhere in the disclosure with reference to compositions including PRPK inhibitors.

Ultraviolet light, for example, light including ultraviolet A (UVA) and ultraviolet B (UVB) wavelengths, may induce skin cancer or tumors. Skin care formulations such as sunscreen or sunblock formulations may be used to reduce or block UVA and UVB exposure, collectively, solar ultraviolet (sUV) exposure. Components of skin care formulations that absorb sUV wavelengths may contribute to the effectiveness of the formulation as a sunscreen or a sunblock to different extents, depending on the structure and the concentration of the respective components. Thus, different components of a skin care formulation may provide different extent of protection from sUV-induced skin cancer.

Different compounds that may provide anti-sUV protection include avobenzone, octocrylene, oxybenzone, octinoxate, octisalate, titanium dioxide, or homosalate. Without being bound by theory, combinations of compounds may be more effective than using single compounds. The anti-sUV effectiveness of a compound or a combination of compounds may be measured in terms of the % reduction in one or both of the average volume or number of tumors. In some embodiments, the anti-sUV effectiveness of a compound or a combination of compounds is measured in terms of the % reduction in the average volume of tumors. For example, if the average volume of tumors for untreated mice is $V_U$, and the average volume of tumors for mice treated with a particular composition including a compound or combination of compounds is $V_C$, the anti-sUV effectiveness may be determined as $100 \times (V_U - V_C)/V_U$. While single compounds such as octocrylene, oxybenzone, octinoxate, and zinc oxide may provide an effectiveness of more than or about 90%, predetermined combinations may provide relatively higher anti-sUV effectiveness. For example, combinations of avobenzone and octinoxate, or octocrylene and zinc oxide, or avobenzone, octocrylene, and titanium dioxide, may provide anti-sUV effectiveness of at least 95%. Combinations of octocrylene and zinc oxide, or avobenzone, octocrylene, and titanium dioxide, may provide anti-SUV effectiveness of at least 99%.

Thus, in some embodiments, a composition includes a pharmaceutically effective amount of at least one anti-solar ultraviolet (anti-sUV) combination for preventing a skin cancer condition. The at least one anti-sUV combination is chosen from the combinations: avobenzone and octinoxate, or octocrylene and zinc oxide, or avobenzone, octocrylene, and titanium dioxide. Any suitable amounts or concentrations of the respective compounds that is pharmaceutically effective to treat a skin cancer condition can be used. For example, the skin cancer condition may include one or more of actinic keratosis, squamous cell carcinoma, or basal cell carcinoma. The at least one anti-sUV combination may be chosen from the combinations: 3% (weight/weight) avobenzone and 7.5% (weight/weight) octinoxate, or 7% (weight/weight) octocrylene and 6.9% (weight/weight) zinc oxide, or 3% (weight/weight) avobenzone, 7% (weight/weight) octocrylene, and 6% (weight/weight) titanium dioxide. The respective concentrations are with reference to a total weight of the composition.

Thus, in some embodiments, the pharmaceutically effective amount of the at least one anti-sUV combination has an anti-sUV effectiveness of at least 95% against the skin cancer condition, where the anti-sUV effectiveness is a percentage reduction in average tumor volume or number. In some embodiments, the anti-sUV effectiveness is at least 99%.

In addition to the at least one combination, the composition may include additional compounds. For example, the composition may further include at least one anti-sUV agent chosen from avobenzone, octocrylene, oxybenzone, octinoxate, octisalate, titanium dioxide, zinc oxide, or homosalate.

Avobenzone (CAS no. 70356-09-1) is an oil-soluble ingredient that absorbs the full spectrum of UVA rays. The maximum absorption is 357 nm. Avobenzone exhibits a change of approximately 36% in UV absorbance following one hour of exposure to sunlight. Octocrylene (CAS no. 6197-30-4) is an organic compound that is an ester that may be formed by the condensation of a diphenylcyanoacrylate with 2-ethylhexanol. It is a viscous, oily liquid that is clear and colorless. The extended conjugation of the acrylate portion of the molecule absorbs UVB and short-wave UVA rays with wavelengths between 280 and 320 nm, protecting the skin from direct DNA damage. The ethylhexanol portion is a fatty alcohol, adding emollient and oil-like (water resistant) properties. Oxybenzone (benzophenone-3) (CAS no. 131-57-7) is a compound belonging to the class of aromatic ketones known as benzophenones. It provides broad-spectrum UV coverage, including UVB and short-wave UVA rays. As a photoprotective agent, it has an absorption profile spanning from 270 to 350 nm with absorption peaks at 288 and 350 nm. Octinoxate (octyl methoxycinnamate) (CAS no. 5466-77-3) absorbs UVB rays from the sun, to protect the skin from damage. Octisalate (octyl salicylate or 2-ethylhexyl salicylate) (CAS no. 118-60-5) is an organic compound that absorbs UVB rays from the sun. Titanium dioxide (CAS no. 13463-67-7 or zinc oxide (CAS no. 1314-13-2) may be used in skin care formulations. Titanium dioxide ($TiO_2$) may be used as a pigment, sunscreen or as a thickener. Titanium dioxide is relatively more effective against UVB, while zinc oxide (ZO) is relatively more effective in the UVA range, and the combination of these particles provides a broad-band UV protection. However, these components have an opaque appearance. Nanoparticles (for example, average size less than 100 nm) of titanium dioxide or zinc dioxide may exhibit reduced or substantially no opacity. Homosalate (CAS no 118-56-9) is an ester of salicylic acid and 3,3,5-trimethylcyclohexanol, a derivative of cyclohexanol. It may be used as a chemical UV filter. The salicylic acid portion of the molecule absorbs UVB rays with wavelengths from 295 nm to 315 nm, protecting the skin from sun damage. The hydrophobic cyclohexanol portion provides greasiness that prevents it from dissolving in water.

The anti-sUV agents and combinations may be provided in a pharmaceutically acceptable or cosmetically acceptable carrier. Thus, in some embodiments, the composition may include the pharmaceutically acceptable carrier or the cosmetically acceptable carrier. For example, the pharmaceutically acceptable carrier or the cosmetically acceptable carrier may include one or more of a cream, a lotion, a spray, a gel, an ointment, a paste, a solution, a suspension, an emulsion, a powder, a liquid, or a solid.

In some embodiments, a skin care formulation may include a composition according to the disclosure. For example, a topical formulation may include any composition according to the disclosure. In some embodiments, formulations or compositions according to the disclosure may include solutions, mixtures, gels, pastes, sprays, creams, lotions, or any other forms suitable for topical application.

In some embodiments, formulations or compositions according to the disclosure may include alternative or additional components or ingredients, including one or more of colorants, pigments, opacifiers, fragrances, preservatives, stabilizers, emulsifiers, emollients, skin conditioners, humectants, surfactants, pharmaceutically active agents, or other suitable components.

In some embodiments, cosmetic formulations or skin care formulations may include one or more preservatives, for example, one or more of benzyl alcohol, phenoxyethanol, sorbic acid, benzoic acid, chlorphenesin, dehydroacetic acid, salicylic acid, methylparaben, ethylparaben, propylparaben, isobutylparaben, butylparaben, imidazolidinyl urea, and diazolidinyl urea. In some embodiments, the compositions and skin care formulations according to the disclosure do not include allergenic preservatives.

Compositions and skin care formulations according to the disclosure may include an emulsion formed by emulsifying two phases. For example, the emulsion may include an oil in water emulsion. An oil in water emulsion is an emulsion in which an aqueous phase is a continuous phase while an oil or hydrophobic phase may be a dispersed phase. In contrast, a water in oil emulsion is an emulsion in which an oil phase is a continuous phase while an aqueous phase may be a dispersed phase. Without wishing to be bound by theory, an oil in water emulsion may be perceived on skin to be smoother and less greasy than a water in oil emulsion, and may be easier to remove from the skin, for example, after a treatment period.

The pH of compositions or formulations according to the disclosure may be set to any suitable pH. In some embodiments, the pH of a composition may be about 7, or close to that of water. For example, a composition may have a pH in a range from 6.8 to 7.5. The pH may be adjusted by adjusting the relative concentrations within the first phase or the second phase, or the relative concentration of the first phase to the second phase. The pH may be adjusted by adding a pH buffering agent to the composition, for example, an agent that maintains a pH within a predetermined range. Buffering agents may include one or more of alpha hydroxy acids, triethanolamine, malic acid, calcium carbonate, sodium phosphate, or any suitable buffering agent for use in cosmetics or skin care formulations.

Thus, compositions and formulations according to the disclosure may be used as skin care formulations, cosmetics, pharmaceutical excipients for topical application to skin. Any suitable techniques may be used for preparing compositions and formulations according to the disclosure. In some embodiments, formulations or compositions according to the disclosure may be packaged into tubes, sprays, bottles, tubs, bags, applicators, kits, or any other suitable containers.

While techniques have been described above, any suitable techniques may be used to prepare formulations and compositions according to the disclosure. Thus, techniques according to the disclosure may be used to prepare compositions and formulations for use as noncarcinogenic skin care formulations, cosmetics, pharmaceutical excipients for topical application to skin.

In some aspects, the present disclosure describes compositions that can be used as, for example, a component in a skin care formulation, or as a skin care formulation. In some embodiments, the skin care formulations may be noncarcinogenic. For example, compared to untreated skin exposed to ultraviolet (UV) wavelengths, skin treated with some compositions of the present disclosure did not exhibit increased incidence of papillomas. Thus, in some embodiments, compositions according to the disclosure may not cause or increase the prevalence of cancers such as, for example, skin cancer. The present disclosure also describes techniques for making the compositions.

Without wishing to be bound by theory, the results of in vivo studies described elsewhere in the disclosure indicate that treatment with compositions according to the disclosure did not exhibit toxicity, and did not damage skin to which compositions were applied. For example, the application of compositions to skin before or after UV exposure did not promote skin cancer compared to skin that was exposed to UV without being treated with compositions. These results indicate that, in some embodiments, compositions according to the disclosure did not have phototoxicity when applied to skin, with or without exposure to solar UV irradiation.

Compositions according to the disclosure are suitable for use as skin care formulations, and may be used as a base composition to which optional additional ingredients or components may be added. Further, compositions according to the disclosure may include a relative low or reduced number of ingredients compared to other skin care compositions. This may reduce the possibility of adverse effects or side effects resulting from the application of compositions to skin.

Some cosmetic formulations or skin care formulations may include one or more preservatives, for example, one or more of benzyl alcohol, phenoxyethanol, sorbic acid, benzoic acid, chlorphenesin, dehydroacetic acid, salicylic acid, methylparaben, ethylparaben, propylparaben, isobutylparaben, butylparaben, imidazolidinyl urea, and diazolidinyl urea. However, susceptible individuals may exhibit allergies to one or more of these preservatives. For example, these and similar preservatives may allergenic preservatives, and may be one of the major causes of allergic contact dermatitis resulting from the use of cosmetic or skin care formulations. In some embodiments, the compositions and skin care formulations according to the disclosure do not include allergenic preservatives.

Compositions according to the disclosure may include ethylenediamine tetra-acetic acid (EDTA) or a salt of EDTA. One or more EDTA salts used in compositions may act as a preservative. EDTA is a chelating agent and may be used, for example, as a preservative or stabilizer. EDTA may prevent catalytic oxidative discoloration, for example, discoloration that may be catalyzed by metal ions. Without being bound by any theory, EDTA and salts of EDTA are believed to be nonallergenic, especially at relatively low concentrations, as described elsewhere in the disclosure.

Compositions and skin care formulations according to the disclosure may include an emulsion formed by emulsifying two phases. For example, the emulsion may include an oil in water emulsion. An oil in water emulsion is an emulsion in which an aqueous phase is a continuous phase while an oil or hydrophobic phase may be a dispersed phase. In contrast, a water in oil emulsion is an emulsion in which an oil phase is a continuous phase while an aqueous phase may be a dispersed phase. Without wishing to be bound by theory, an oil in water emulsion may be perceived on skin to be smoother and less greasy than a water in oil emulsion, and may be easier to remove from the skin, for example, after a treatment period.

A composition according to disclosure may include at least one of a first phase or a second phase. In some embodiments, compositions may include both of the first phase and the second phase. One or both of the first or the second phases may be a solid, a liquid, a gel, a paste, or an emulsion, at room temperature, for example, at 25° C. One or both of the first or the second phases may be heated before or during combining with the other phase, for example, to at least partially or completely melt, liquefy, or solubilize one or more components or ingredients within the first or second phase.

In some embodiments, the first phase includes one or more of a chelating agent, a humectant, and a skin conditioning agent. A chelating agent may be a multidentate ligand, or agent capable of forming multiple bonds with metal ions. The chelating agent may include one or more of ethylenediaminetetraacetic (EDTA), or a salt of EDTA. The salt of EDTA may include one or more of calcium disodium EDTA, diammonium EDTA, dipotassium EDTA, disodium EDTA, triethanolamine EDTA (TEA-EDTA), tetrasodium EDTA, tripotassium EDTA, trisodium EDTA, hydroxyethyl ethylenediamine triacetic acid (HEDTA), or trisodium HEDTA. In some embodiments, the chelating agent consists of disodium EDTA. In some embodiments, the chelating agent may also function as a nonallergenic preservative. In some embodiments, the first phase may include a relative low amount of a salt of EDTA. For example, the first phase may include less than 0.05% (weight/volume) of an EDTA salt, for example, from 0.01% to 0.05% of an EDTA salt. The first phase may include one or more of EDTA, an EDTA salt, phytic acid (for example, 0.05-0.15%), gluconic acid (for example, 0.001-0.18%), or tartaric acid (for example, 1-3%) as chelating agents.

The humectant may be an agent having an affinity for or being capable of binding to, water. For example, the humectant may include a hygroscopic substance that may maintain a predetermined level of moistness. In some embodiments, the humectant may include a molecule including one or more groups capable of forming hydrogen bonds with water. The humectant may include several hydrophilic groups, for example, hydroxyl groups. The hydrophilic groups may include one or more of hydroxyl groups, amines, carboxyl groups, or esterified carboxyl groups. In some embodiments, the humectant may include 1,3-butylene glycol. For example, the first phase may include 4% to 6% (volume/volume) 1,3-butylene glycol. In some embodiments, the humectant may include glycerin. For example, the first phase may include 5% to 10% (volume/volume) glycerin. In some embodiments, the first phase may include one or more of 1,3-butylene glycol, glycerin, polyethylene glycol (PEG) (for example, 1.0 to 2.5%), PEG-100, sorbitol (for example, 5-50%), trehalose (for example, 0.2-0.5%), sodium pyrrolidone carboxylic acid (for example, 0.1-1%), or propylene glycol (for example, 1-7%) as a humectant.

The skin conditioning agent may be an emollient, which acts as a lubricant on the skin surface, giving the skin a soft and smooth appearance. The skin conditioning agent may include pentylene glycol. For example, the first phase may include 1.3% to 3.0% (volume/volume) pentylene glycol. In some embodiments, the skin conditioning agent may include an emollient, for example, one or more of pentylene glycol, cyclomethicone (for example, 0.1-0.5%), dicapryl carbonate (for example, 1-5%), isononyl isononanoate (for example, 0.5-2%), pentaerythrityl distearate (for example, 0.5-1%), cetyl lactate (for example, 0.5-1%), sodium hyaluronate (for example, 0.1-1%), or dimethicone (for example, 1-3%).

In some embodiments, the first phase includes 1,3-butylene glycol, glycerin, pentylene glycol, a salt of ethylenediaminetetraacetic acid (EDTA), and water. The water may be one or more of unfiltered water, filtered water, sterilized water, ozonized water, UV-treated water, distilled water, or deionized water. In some embodiments, the first phase consists of 1,3-butylene glycol, glycerin, pentylene glycol, a salt of ethylenediaminetetraacetic acid (EDTA), and water. In some embodiments, the first phase consists essentially of 1,3-butylene glycol, glycerin, pentylene glycol, a salt of ethylenediaminetetraacetic acid (EDTA), and water, except for minor components such as colorants, pigments, fragrances, aromatics, or impurities, below a predetermined threshold. The first phase may include 0.01% to 0.05% (weight/volume) salt of EDTA, 4% to 6% (volume/volume) 1,3-butylene glycol, 5% to 10% (volume/volume) glycerin, 1.3% to 3.0% (volume/volume) pentylene glycol, and 81% to 90% (volume/volume) water. The first phase may be an aqueous phase, with water forming the major component of the first phase. The first phase may be combined with the second phase, for example, by emulsifying or any other technique, including simple mixing, to form compositions.

In some embodiments, the second phase includes one or more of an emulsion stabilizer, an emulsifying agent, or a skin conditioning agent. The emulsion stabilizer may be an agent that prolongs the stability of an emulsion, for example, by preventing the disperse phase and the continuous phase of the emulsion from separating or coalescing. In some embodiments, the second phase may include cetyl alcohol as an emulsion stabilizer. For example, the second phase may include 10% to 25% (weight/volume) cetyl alcohol.

The emulsifying agent may be an agent that promotes the formation of an emulsion, for example, by promoting the uniform dispersion of the dispersed phase within the continuous phase of the emulsion. In some embodiments, the second phase includes glyceryl stearate as an emulsifying agent. For example, the second phase may include 10% to 25% (weight/volume) glyceryl stearate.

The skin conditioning agent in the second phase may include hydrogenated polydecene, in addition to, or instead of, one or more skin conditioning agents described with reference to the first phase. For example, the second phase may include 50% to 80% (volume/volume) hydrogenated polydecene.

In some embodiments, the second phase includes cetyl alcohol, glyceryl stearate, and hydrogenated polydecene. In some embodiments, the second phase consists of cetyl alcohol, glyceryl stearate, and hydrogenated polydecene. In some embodiments, the second phase consists essentially of cetyl alcohol, glyceryl stearate, and hydrogenated polydecene, except for minor components such as colorants, pigments, fragrances, aromatics, or impurities, below a predetermined threshold. In some embodiments, the second phase may include 10% to 25% cetyl alcohol (weight/volume), 10% to 25% glyceryl stearate (weight/volume), and 50% to 80% (volume/volume) hydrogenated polydecene. The second phase may be an oil or hydrophobic phase. The second phase may be combined with the first phase, for example, by emulsifying or any other technique, including simple mixing, to form compositions.

While various components of the first and the second phase have been described with reference to functionality as one or more of chelating agents, humectants, skin conditioning agents, other functions, components may have more than one functions, or may exhibit different functions at different concentrations. For example, glycerin may act as one or more of a humectant, a viscosity decreasing agent, or a skin conditioning agent. Cetyl alcohol may act as one or more of an emulsion stabilizer, an emulsifying agent, an opacifying agent, or a thickener. Glyceryl stearate may act as one or both of an emollient or an emulsifying agent. Further, one or more components may have functions in addition to, or instead of, the example functions described with reference to the first phase or the second phase.

In some embodiments, a composition includes both the first phase and the second phase, for example, in addition to other components. In some embodiments, a composition consists of the first phase and the second phase. In some embodiments, a composition consists essentially of the first and the second phase, except for minor components, for example, colorants, pigments, fragrances, aromatics, or impurities, below a predetermined threshold concentration. In some embodiments, a composition consists essentially of 1,3-butylene glycol, glycerin, pentylene glycol, a salt of ethylenediaminetetraacetic acid (EDTA), water, cetyl alcohol, glyceryl stearate, and hydrogenated polydecene. For example, the minor components may be present at a concentration of less than 1% (weight/volume), or less than 0.1% (weight/volume), or less than 0.01% (weight/volume).

In some embodiments, a composition according to the disclosure is substantially free of one or more allergenic preservatives. For example, the one or more allergenic preservatives that the example composition is free of may include one or more of benzyl alcohol, phenoxyethanol, sorbic acid, benzoic acid, chlorphenesin, dehydroacetic acid, salicylic acid, methylparaben, ethylparaben, propylparaben, isobutylparaben, butylparaben, imidazolidinyl urea, or diazolidinyl urea. The term "substantially free of" indicates that the one or more allergenic preservatives are completely absent from the compositions, or are at a concentration less than a predetermined threshold, for example, less than 1% (weight/volume), or less than 0.1% (weight/volume), or less than 0.01% (weight/volume), or less than any threshold below which the preservative will not exhibit allergenicity.

In embodiments in which compositions according to the disclosure include an emulsion, the emulsion may include an oil in water emulsion, wherein the oil in water emulsion comprises the first phase and the second phase. In some embodiments, the first phase may constitute an aqueous phase of the emulsion. Alternatively, compositions according to the disclosure including emulsions may include a water in oil emulsion, wherein the oil in water emulsion comprises the first phase and the second phase. Thus, either of the first phase or the second phase may be a continuous phase or a dispersed phase in an emulsion, according to different embodiments.

The pH of compositions may be set to any suitable pH. In some embodiments, the pH of a composition may be about 7, or close to that of water. For example, a composition may have a pH in a range from 6.8 to 7.5. The pH may be adjusted by adjusting the relative concentrations within the first phase or the second phase, or the relative concentration of the first phase to the second phase. The pH may be adjusted by adding a pH buffering agent to the composition, for example, an agent that maintains a pH within a predetermined range. Buffering agents may include one or more of alpha hydroxy acids, triethanolamine, malic acid, calcium carbonate, sodium phosphate, or any suitable buffering agent for use in cosmetics or skin care formulations.

In some embodiments, a formulation according to the disclosure may include one or more compositions according to the disclosure. For example, the formulation may be a topical skin care formulation, or a cosmetic formulation, or any other formulation suitable for application to skin. In some embodiments, the formulation may be a base formulation to which additional ingredients or components may be added.

In some embodiments, formulations or compositions according to the disclosure may be noncarcinogenic. For example, formulations or compositions according to the disclosure may not increase the incidence of average number of papillomas on the skin on exposure for a predetermined period of time to predetermined ultraviolet (UV) wavelengths. Skin that is treated with compositions or formulations according to the disclosure may exhibit the same number of papillomas as untreated skin, on exposure to UV wavelengths. For example, the UV wavelengths may include sunlight, solar simulated light, or other light spectra that may include one or more of visible and infrared wavelengths in addition to UV wavelengths. The UV wavelengths may include one or more wavelengths or wavelength bands having wavelengths less than about 400 nm.

In some embodiments, formulations or compositions according to the disclosure may include anti-wrinkling or anti-aging compounds. For example, compounds that may have one or both of an anti-wrinkling or anti-aging effect on skin may include one or more of retinoic acid, retinoic acid derivatives, kaempferol, licochalcone A, resveratrol, aspirin, eupafolin chrysin derivatives, caffeic acid, 6-C-(E-phenylethenyl)-naringenin, butein, ginsenosides, gingerol, shogaol, quercetin-3-methyl ether, esculetin, clnQ-03, ginseng and its metabolites, taxifolin, aloe-emodin, ceftriaxone, norathyriol, epigallocatechin gallate (EGCG), eriodictyol, isorhamnetin, 3-chloroacetyl-indole, 3,6,2',4',5'-pentahydroxyflavone, Isoliquiritigenin, 2'-hydroxycinnamicadelhyde (i.e. cinnamon), A4-amino-2-(butyrylamino)phenyl(2E,4E,6E,8E)-3, 7-dimethyl-9-(2,6,6-trimethyl-1-cyclohexenyl)-2,4,6,8-nonatetraenoate (a retinoic acid derivative), 7,3,4'-trihydroxyisoflavone, delphiniden, magnolol, 6,7,4'-trihydroxyisoflavone, naringenin, caffeic acid phenylethyl ester (CAPE), 3,7,4'-trihydroxyflavone, myricetin, quercetagetin, isorhamnetin, luteolin, or herbacetin. In some examples, the anti-aging or anti-wrinkling compounds may include one or more compounds chosen from 7,3,4'-trihydroxyisoflavone, delphiniden, magnolol, 6,7,4'-trihydroxyisoflavone, naringenin, CAPE, 3,7,4'-trihydroxyflavone, myricetin, quercetagetin, isorhamnetin, luteolin, or herbacetin. Any suitable concentration of one or more of these compounds may be used. For example, the concentration of one or more of these compounds may be up to about 0.1% by weight, or up to about 100,000 IU/oz. In some examples, the anti-aging or anti-wrinkling compounds may include one or more compounds chosen from 6,7,4'-trihydroxy-isoflavone, naringenin, 5-deoxy-kaempferol, isorhamnetin, or luteolin. One or more anti-aging or anti-wrinkling compounds may inhibit one or more of the nuclear factor kappa B (NF-κB) pathway, reactive oxygen species (ROS), or the secretion of inflammatory cytokines from human peripheral blood mononuclear cells (PBMCs), or may promote or increase one or more of NF-E2-related factor (Nrf2) activity, the antioxidant response element (ARE) pathway, collagen 1A activity, or elastin activity.

Skin whitening, skin lightening, and/or skin bleaching (collectively referred to as skin lightening) refer to the practice of using chemical substances in an attempt to lighten skin tone or provide an even skin complexion by reducing the local concentration of melanin. For example, specific zones of abnormally high pigmentation such as moles and birthmarks may be depigmented to match to the surrounding skin. In some embodiments, compositions and formulations according to the disclosure may include skin whitening, lightening, or bleaching agents. For example, one or more of hydroquinone (also known as benzene-1,4-diol or quinol), alpha arbutin (bearberry bush leaf extract), resveratrol (3,5,4'-trihydroxy-trans-stilbene), or sepicalm-S(SEPPIC, Inc., Air Liquide, Paris, France) may be used.

While formulations and compositions according to the disclosure may include emulsions including one or both of the first phase or the second phase, in some embodiments, formulations or compositions may include solutions, mixtures, gels, pastes, sprays, creams, lotions, or any other forms suitable for topical application. For example, one or both of the first or the second phase may be blended or combined with each other or with other components. While examples of components of the first or the second phase have been described, formulations and compositions may include alternative or additional components or ingredients, including one or more of colorants, pigments, opacifiers, fragrances, preservatives, stabilizers, emulsifiers, emollients, skin conditioners, humectants, pharmaceutically active agents, or other suitable components.

Thus, compositions and formulations according to the disclosure may be used as noncarcinogenic skin care formulations, cosmetics, pharmaceutical excipients for topical application to skin without increasing or promoting carcinogenicity.

Any suitable techniques may be used for preparing compositions and formulations according to the disclosure. A technique according to the disclosure may include agitating the first phase, and forming a composition by introducing the second phase into the first phase during the agitating. For example, one or both of the first or the second phase may be contained in a container, a reaction chamber, a vessel, a batch processor, or may flow in a continuous system, for example, via pipes, conveyors, inline mixers, and may be agitated. In some embodiments, the agitating may include one or more of shaking, vibrating, centrifuging, or stirring. In some embodiments, the agitating includes causing one or both of the first or second phases to flow across or along an object or an obstacle, for example, a baffle. In other examples, the agitating includes moving an object, for example, an impeller, stirrer, or mixer, within a bulk of one or both of the first or second phases. The agitating may include continuous or intermittent agitation. In some embodiments, the agitating includes stirring one or both of the first phase or the second phase by a rotation of 1500 to 2000 rotations per minute (rpm). The agitating may be continued as the second phase is introduced into the first phase.

Techniques according to the disclosure may further include increasing the agitation, for example, by increasing the rotation to 3000 to 3500 rpm. In some embodiments, after increasing the agitation, the agitation may be reduced, for example, back to 1500 to 2000 rpm. Thus, in some embodiments, the technique may include reducing the agitation to 1500 to 2000 rpm.

The temperature of one or more of the first phase, the second phase, or a composition formed by combining the first and second phases may be maintained within a predetermined temperature range or substantially at a predetermined temperature. For example, a temperature range may be selected to promote the formation of an emulsion, or to promote the stability of the emulsion. In some embodiments, instead of a constant temperature, the temperature may be changed according to a predetermined program. For example, ingredients or components of the first or the second phase may be heated to a first temperature, to promote melting, fusing, liquefaction, or blending of one or more ingredients. The first or the second phase may be maintained at a second temperature during the agitating. After the agitating, the composition formed from combining the first and second phase may be maintained at a third temperature, before cooling to room temperature or a storage temperature.

Techniques according to the disclosure may include maintaining one or more of the first phase, the second phase, or the composition at about 70° C. for a predetermined period of time. The temperature may be measured using any suitable physical, electronic, infrared, or other thermometer or temperature sensor. In some embodiments, the technique further includes cooling the composition formed by combining the first and the second phase, or allowing the composition to cool, to a temperature of about 45° C. during the agitating. The temperature may be maintained using active heating or cooling apparatus, or by passively allowing the temperature to match ambient temperatures. In some embodiments, the technique further includes cooling the composition or allowing the composition to cool to a temperature of about 30° C. during the agitating.

One or more optional components may be added to the composition. In some embodiments, the technique further includes comprising adding one or more optional components to the composition during the agitating. In some embodiments, the technique further includes comprising adding one or more optional components to the composition before or after the agitating.

In some embodiments, the agitating may result in emulsifying of the first and the second phase. For example, forming the composition may include emulsifying the second phase into the first phase to form an oil in water emulsion.

After the composition is formed by combining, for example, by emulsifying, the first and the second phases, the composition may be packaged for bulk or retail packaging. In some embodiments, formulations or compositions according to the disclosure may be packaged into tubes, sprays, tubs, bags, applicators, kits, or any other suitable containers.

While techniques have been described above, any suitable techniques may be used to prepare formulations and compositions according to the disclosure. Thus, techniques according to the disclosure may be used to prepare compositions and formulations for use as noncarcinogenic skin care formulations, cosmetics, pharmaceutical excipients for topical application to skin without increasing or promoting carcinogenicity.

Examples of PRPK inhibitors, and compositions including one or more of PRPK inhibitors, anti-solar ultraviolet (anti-sUV) combinations, and a first or a second phase, and techniques including applying or administering such compositions are described in the disclosure.

The present disclosure will be illustrated by the following non-limiting examples.

EXAMPLES

Example 1—Knocking Out TOPK Expression Blocks sUV-Induced Skin Cancer

Figure 3A:
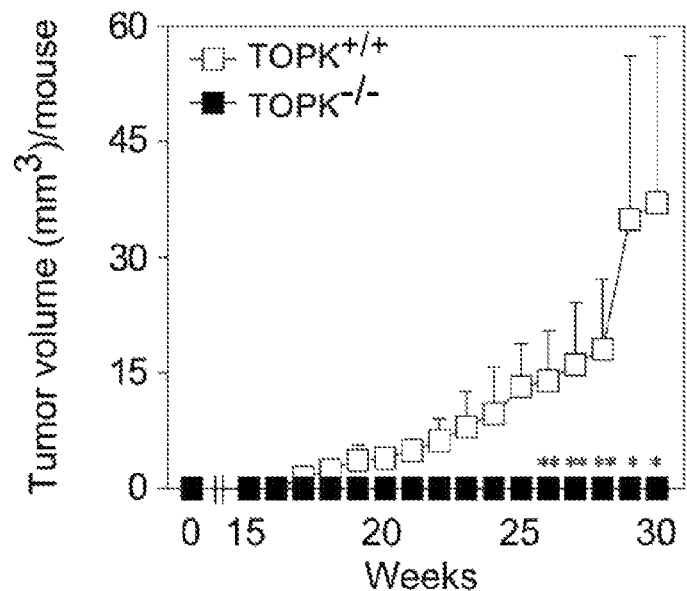
FIG. 3A is a chart comparing average tumor volume over time in TOPK knockout mice and wildtype mice.

The effect of TOPK expression on sUV-induced skin cancer development in a squamous cell carcinoma (SCC) SKH-1 (hairless) mouse model was evaluated. The average number of tumors and average tumor volume was monitored in wildtype (TOPK$^{+/+}$) mice and TOPK knockout (TOPK$^{-/-}$) mice exposed to sUV. FIG. 3A is a chart comparing average tumor volume over time in TOPK knockout mice and wildtype mice.

Figure 3B:
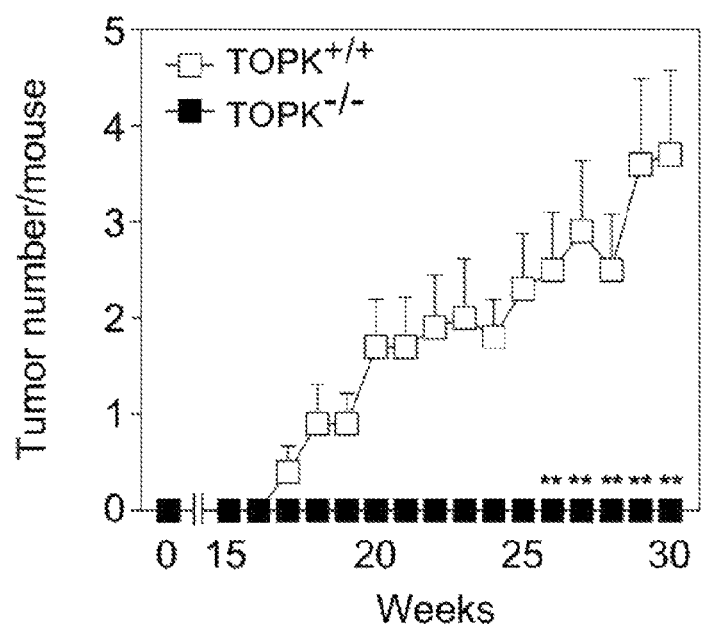
FIG. 3B is a chart comparing average tumor number over time in TOPK knockout mice and wildtype mice.

FIG. 3B is a chart comparing average tumor number over time in TOPK knockout mice and wildtype mice. As seen in FIGS. 3A and 3B, the average volume (size) and number of tumors in wildtype mice exposed to sUV increased over a period of 30 weeks. In contrast, TOPK knockout mice exhibited substantially no tumors over the same period of time. Thus, knocking out TOPK expression completely blocked sUV-induced skin cancer development in the SCC mouse model.

Figure 4A:
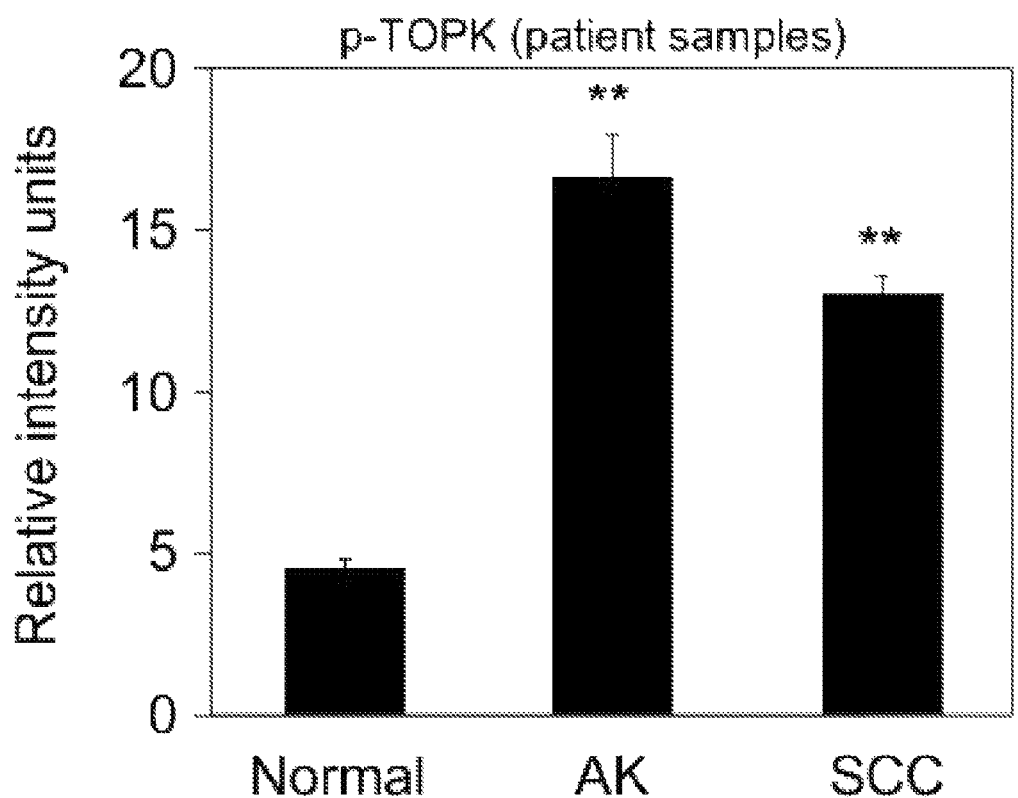
FIG. 4A is a chart comparing the expression of phosphorylated TOPK in actinic keratosis, squamous cell carcinoma, and normal skin in patient skin samples.
Figure 4B:
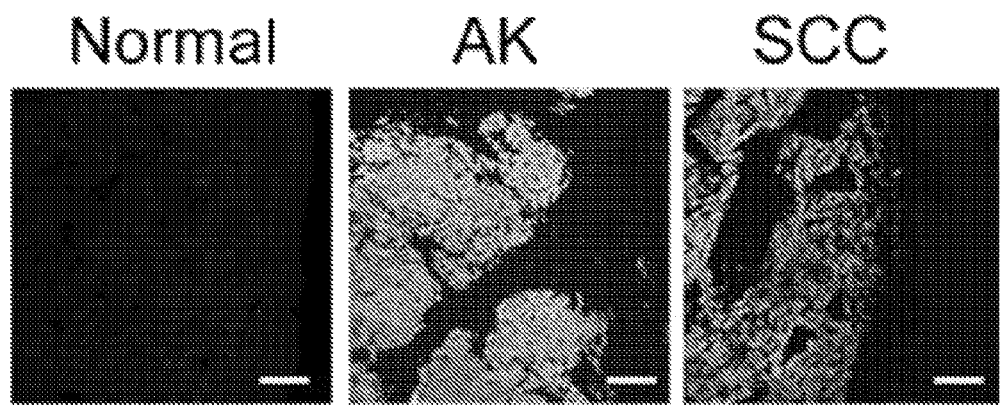
FIG. 4B is a photograph comparing the immunohistochemistry of the samples of FIG. 4A.
Figure 4C:
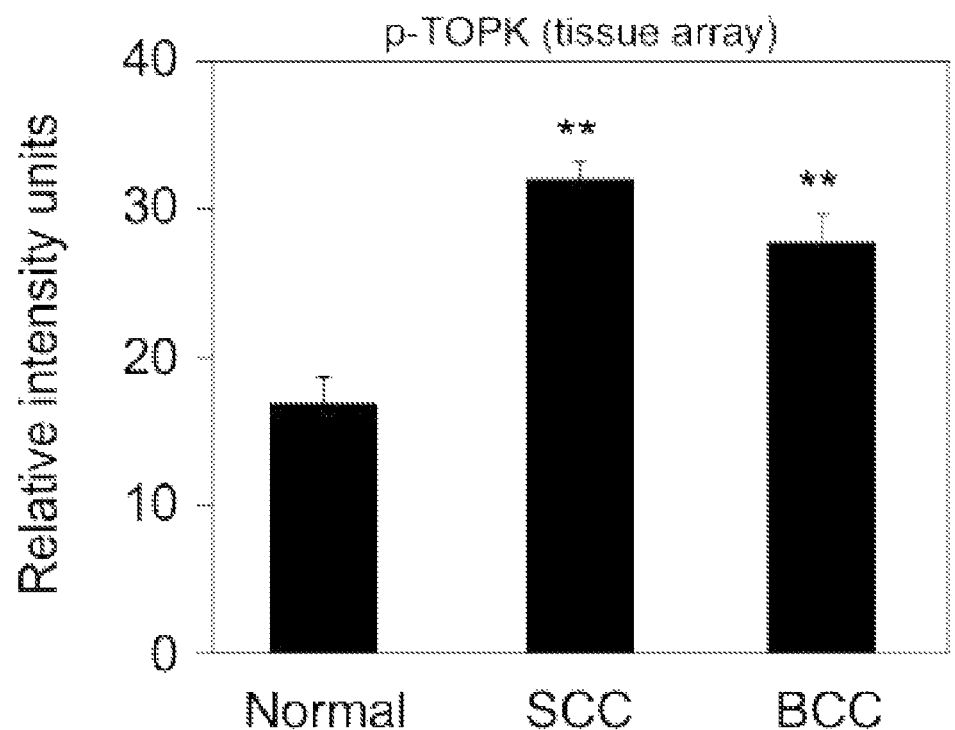
FIG. 4C is a chart comparing the expression of phosphorylated TOPK in squamous cell carcinoma, basal cell carcinoma, and normal skin in human skin cancer tissue array samples.
Figure 4D:
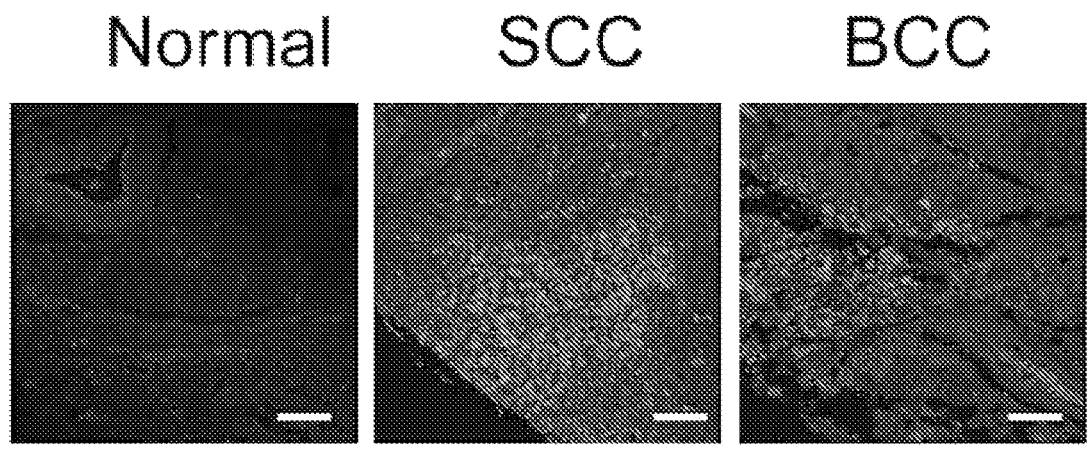
FIG. 4D is a photograph comparing the immunohistochemistry of the samples of FIG. 4C.
Figure 4E:
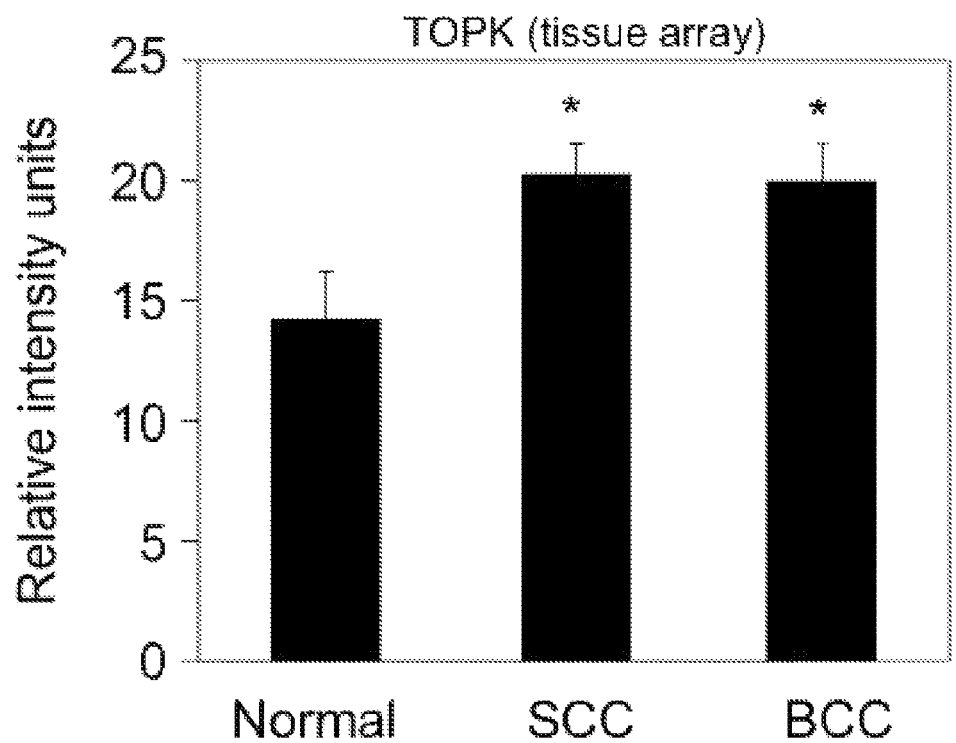
FIG. 4E is a chart comparing the expression of total TOPK in squamous cell carcinoma, basal cell carcinoma, and normal skin in human skin cancer tissue array samples.
Figure 4F:
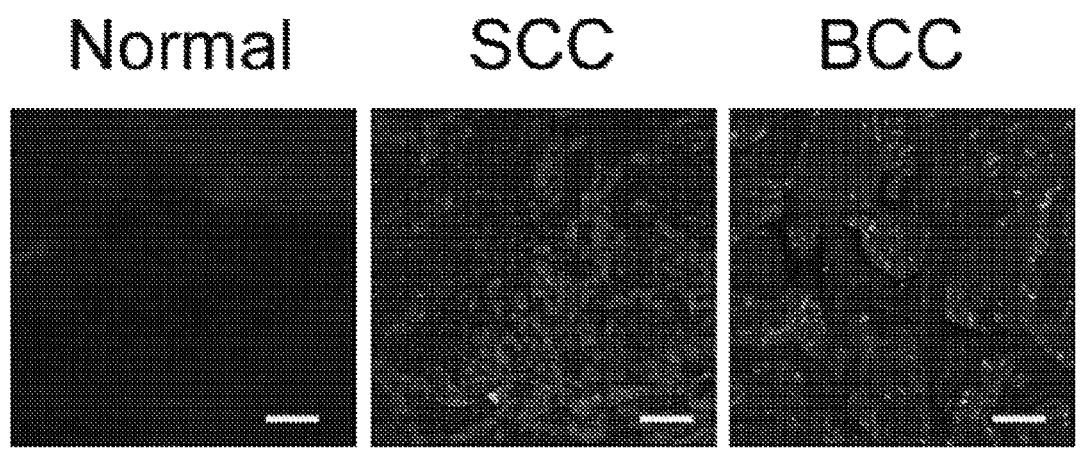
FIG. 4F is a photograph comparing the immunohistochemistry of the samples of FIG. 4E.

Example 2—AK and SCC Cells Exhibit Higher Total and Phosphorylated TOPK Expression The expression of total and phosphorylated TOPK in different cell types was evaluated. FIG. 4A is a chart comparing the expression of phosphorylated TOPK (p-TOPK) in actinic keratosis (AK), squamous cell carcinoma (SCC), and normal skin in patient skin samples. FIG. 4B is a photograph comparing the immunohistochemistry of the samples of FIG. 4A. FIG. 4C is a chart comparing the expression of phosphorylated TOPK in squamous cell carcinoma, basal cell carcinoma (BCC), and normal skin in human skin cancer tissue array samples. FIG. 4D is a photograph comparing the immunohistochemistry of the samples of FIG. 4C. FIG. 4E is a chart comparing the expression of total TOPK in squamous cell carcinoma, basal cell carcinoma, and normal skin in human skin cancer tissue array samples. FIG. 4F is a photograph comparing the immunohistochemistry of the samples of FIG. 4E.

As seen in FIGS. 4A and 4B, p-TOPK is highly expressed in AKs and SCCs in patient samples, compared to normal skin cells from patient samples. As seen in FIGS. 4C and 4D, p-TOPK is highly expressed in a tissue array of human SCC and BCC compared to normal tissue. As seen in FIGS. 4E and 4F, total TOPK is also highly expressed in a tissue array of human SCC and BCC compared to normal tissue. Thus, TOPK is relatively highly expressed in AK and SCC cells.

Example 3—TOPK Binds to PRPK and Phosphorylates PRPK

Figure 5A:
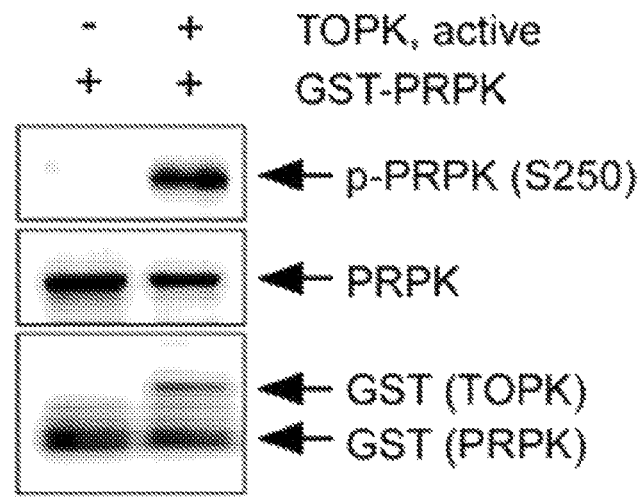
FIG. 5A is a photograph illustrating a chromatographic plate comparing PRPK phosphorylation at site Ser250 in the presence and absence of TOPK.
Figure 5B:
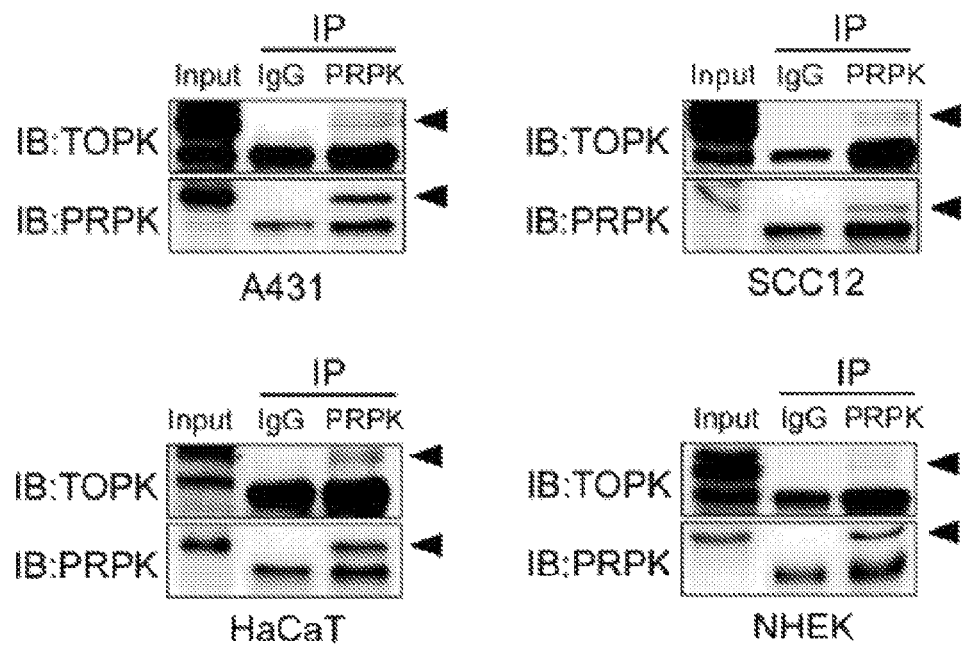
FIG. 5B is a photograph illustrating a chromatographic plate showing pull down assay results indicative of endogenous binding activity between TOPK and PRPK in A431, SCC12, HaCaT and NHEK cells, respectively.

The interaction of TOPK with potential downstream targets that could be implicated in inhibition of carcinogenicity was evaluated. One of the targets evaluated was p53-related protein kinase (PRPK). FIG. 5A is a photograph illustrating a chromatographic plate comparing PRPK phosphorylation at site Ser250 in the presence and absence of TOPK. As seen in FIG. 5A, TOPK directly binds to and strongly phosphorylates PRPK. The Ser250 site of PRPK is known to be indicative of PRPK activity. FIG. 5B is a photograph illustrating a chromatographic plate showing pull down assay results indicative of endogenous binding activity between TOPK and PRPK in A431, SCC12, HaCaT and NHEK cells, respectively. The pull down assay results in FIG. 5B further confirm that TOPK and PRPK directly interact, thereby demonstrating that PRPK is a novel protein-binding partner with TOPK.

Example 4—TOPK Wildtype Mice Exhibit Higher Total and Phosphorylated PRPK Expression The expression of phosphorylated PRPK (p-PRPK) was compared in TOPK wildtype (+/+) and knockout (−/−) mice.

Figure 6:
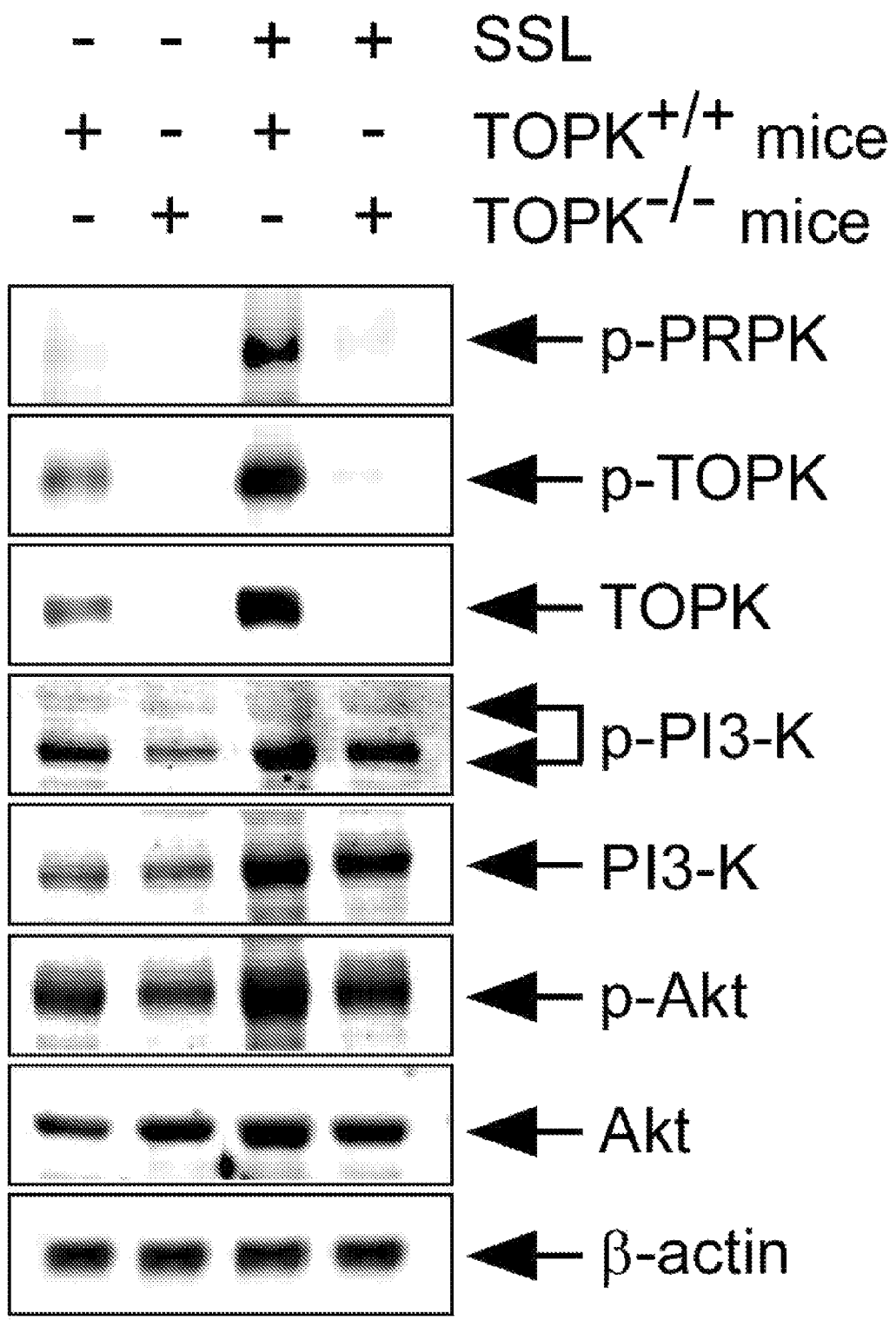
FIG. 6 is a photograph illustrating a chromatographic plate comparing the total levels and phosphorylation levels of PRPK, TOPK, PI3-K and AKT in TOPK wildtype (+/+) and knockout (−/−) mice exposed or not exposed to solar simulated ultraviolet light.

FIG. 6 is a photograph illustrating a chromatographic plate comparing the total levels and phosphorylation levels of PRPK, TOPK, PI3-K and AKT in TOPK wildtype (+/+) and knockout (−/−) mice exposed or not exposed to solar simulated ultraviolet light. Beta actin serves as a loading control. As seen in FIG. 6, phosphorylated PRPK is absent in TOPK knockout (TOPK$^{-/-}$) mice exposed to chronic solar simulated light (SSL) compared with wild-type (TOPK$^{+/+}$) mice.

Figure 7A:
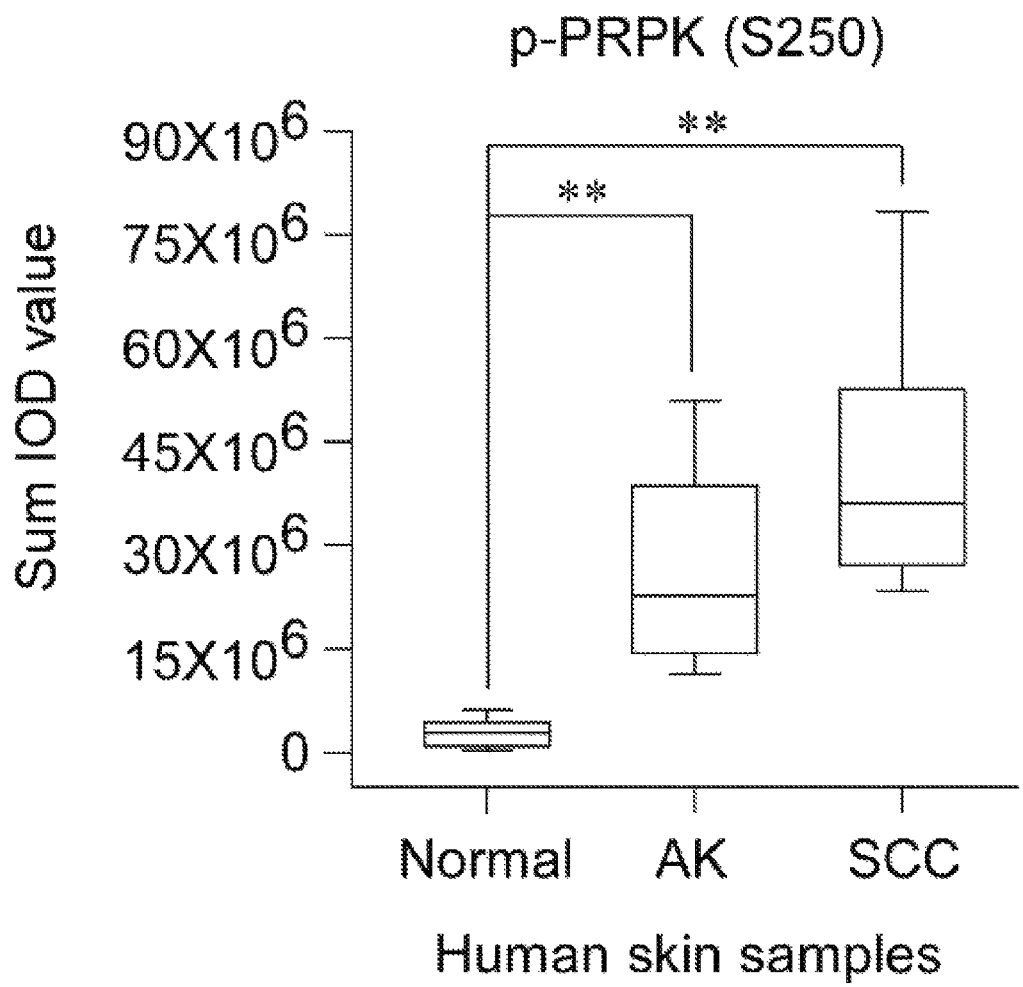
FIG. 7A is a chart comparing the phosphorylation of PRPK in actinic keratosis, squamous cell carcinoma, and normal skin.
Figure 7B:
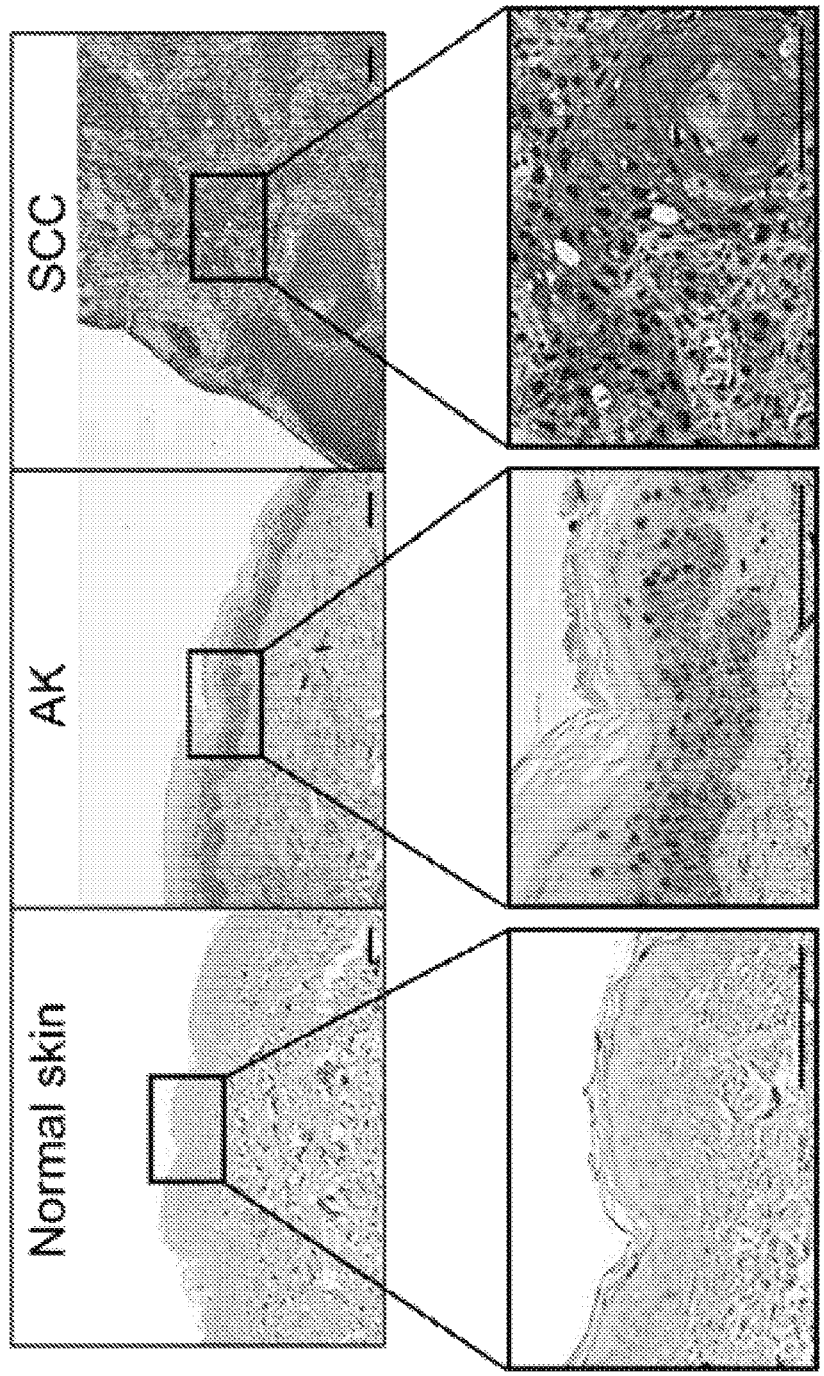
FIG. 7B is a photograph comparing the immunohistochemistry of the samples of FIG. 7A.

Example 5—AK and SCC Cells Exhibit Higher Total and Phosphorylated TOPK Expression FIG. 7A is a chart comparing the phosphorylation of PRPK in actinic keratosis, squamous cell carcinoma, and normal skin. FIG. 7B is a photograph comparing the immunohistochemistry of the samples of FIG. 7A. As seen in FIGS. 7A, and 7B, PRPK is highly phosphorylated in AKs and SCCs compared to normal human skin.

Example 6—sUV Exposure Increases TOPK and PRPK Expression

Figure 8:
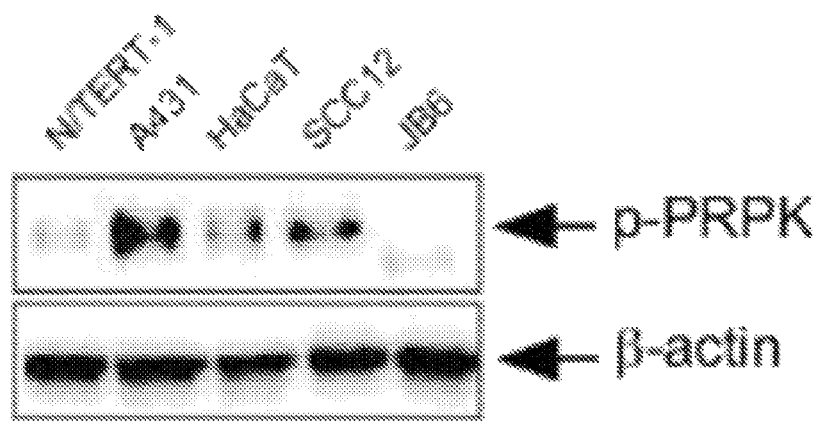
FIG. 8 is a photograph illustrating a chromatographic plate comparing the expression of phosphorylated PRPK in normal (N/TERT-1, HaCaT, JB6) and squamous cell carcinoma-related (A431 and SCC12) cell lines.
Figure 9A:
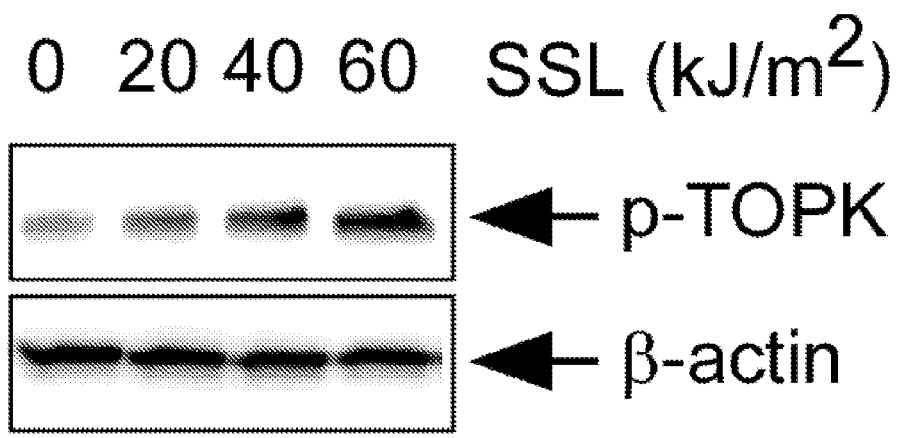
FIG. 9A is a photograph illustrating a chromatographic plate comparing the expression of phosphorylated TOPK in HaCaT cells with an increase in the magnitude of dose of SSL exposure.
Figure 9B:
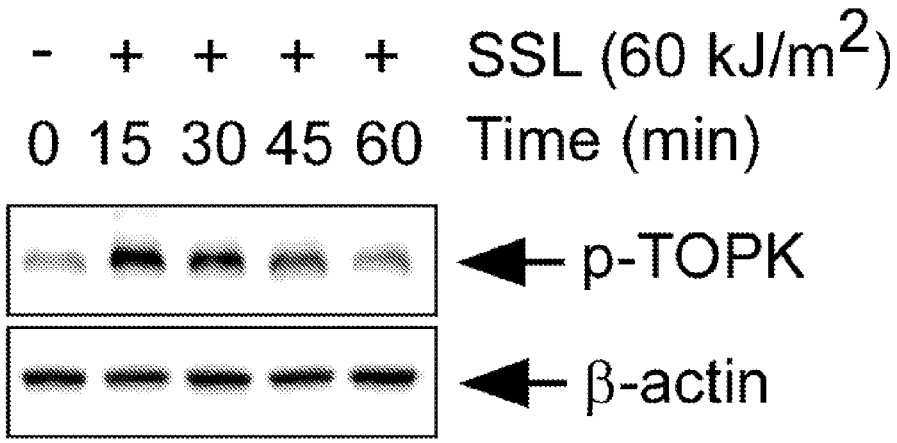
FIG. 9B is a photograph illustrating a chromatographic plate comparing the expression of phosphorylated TOPK in HaCaT cell lines at various times after exposure to a dose of 60 kJ/m$^2$ of solar simulated ultraviolet light (SSL that mimics natural sUV) exposure.
Figure 10A:
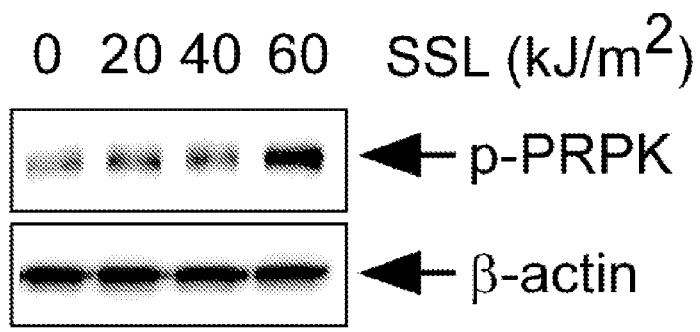
FIG. 10A is a photograph illustrating a chromatographic plate comparing the expression of phosphorylated PRPK in HaCaT cells with an increase in the magnitude of dose of SSL exposure.
Figure 10B:
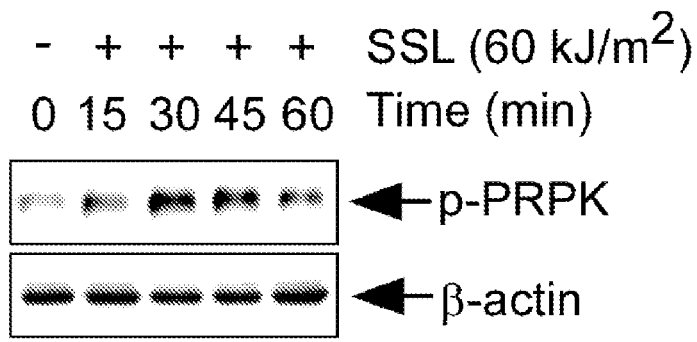
FIG. 10B is a photograph illustrating a chromatographic plate comparing the expression of phosphorylated PRPK in HaCaT cells at various times after exposure to a dose of 60 kJ/m$^2$ of SSL exposure.

A solar simulated light (SSL) system was used to evaluate the effect of sUV exposure on TOPK and PRPK expression. The SSL system mimics sUV exposure and was used to obtain these data. FIG. 8 is a photograph illustrating a chromatographic plate comparing the expression of phosphorylated PRPK in normal (N/TERT-1, HaCaT, JB6) and squamous cell carcinoma-related (A431 and SCC12) cell lines. Phosphorylated PRPK (p-PRPK) is overexpressed in SCC-related cell lines, including A431 and SCC12 cells, as seen in FIG. 8. FIG. 9A is a photograph illustrating a chromatographic plate comparing the expression of phosphorylated TOPK in HaCaT cells with an increase in the magnitude of dose of SSL exposure. FIG. 9B is a photograph illustrating a chromatographic plate comparing the expression of phosphorylated TOPK in HaCaT cell lines at various times after exposure to a dose of 60 kJ/m$^2$ of solar simulated ultraviolet light (SSL that mimics natural sUV) exposure. FIG. 10A is a photograph illustrating a chromatographic plate comparing the expression of phosphorylated PRPK in HaCaT cells with an increase in the magnitude of dose of SSL exposure. FIG. 10B is a photograph illustrating a chromatographic plate comparing the expression of phosphorylated PRPK in HaCaT cells at various times after exposure to a dose of 60 kJ/m$^2$ of SSL exposure. TOPK (FIGS. 9A and 9B) and PRPK (FIGS. 10A and 10B) phosphorylation in HaCaT cells increased by SSL irradiation.

Figure 11:
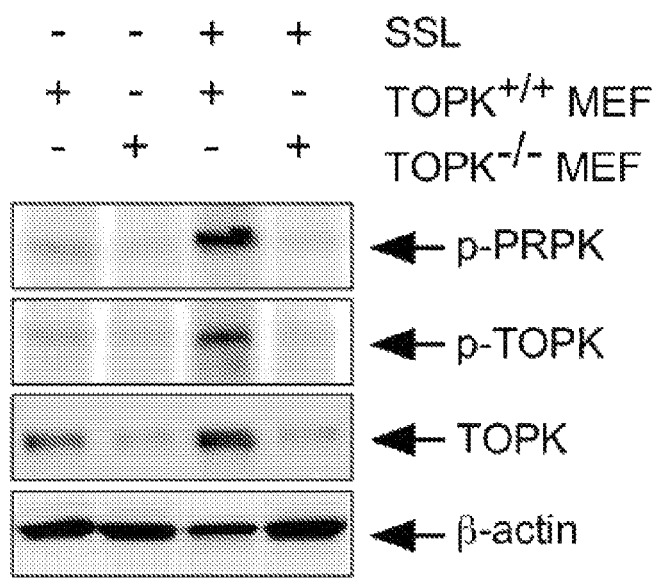
FIG. 11 is a photograph illustrating a chromatographic plate comparing the expression of phosphorylated TOPK and total TOPK in wildtype and TOPK knockout murine embryonic fibroblasts exposed or not exposed to SSL.

FIG. 11 is a photograph illustrating a chromatographic plate comparing the expression of phosphorylated TOPK and total TOPK in wildtype and TOPK knockout murine embryonic fibroblasts exposed or not exposed to SSL. Knockout of TOPK expression in murine embryonic fibroblasts (MEFs) was associated with disappearance of SSL-induced PRPK phosphorylation, as seen in FIG. 11.

Figure 12A:
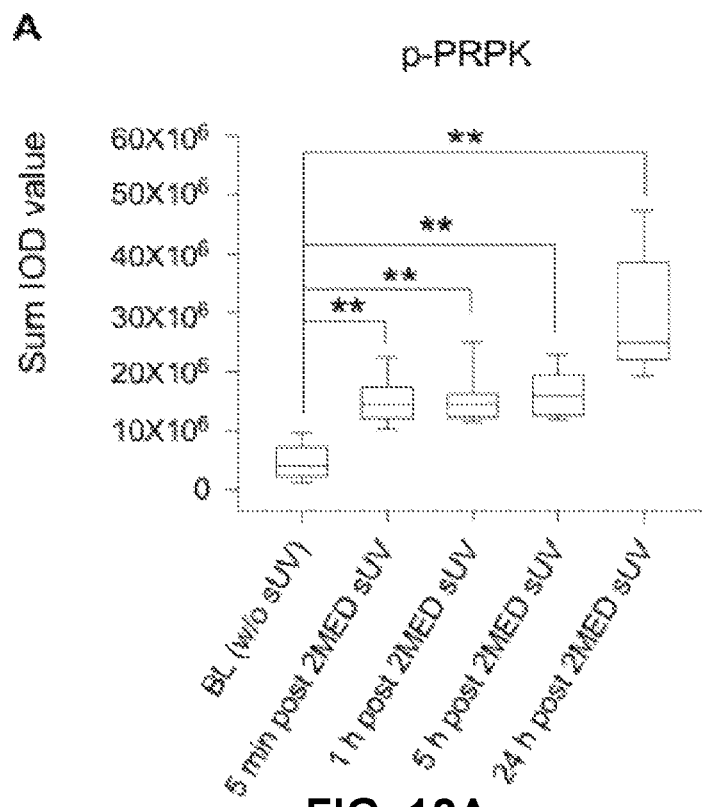
FIG. 12A is a chart comparing the expression of phosphorylated PRPK in human skin harvested at various times after exposure to solar UV at a dose of 2 MED.
Figure 12B:
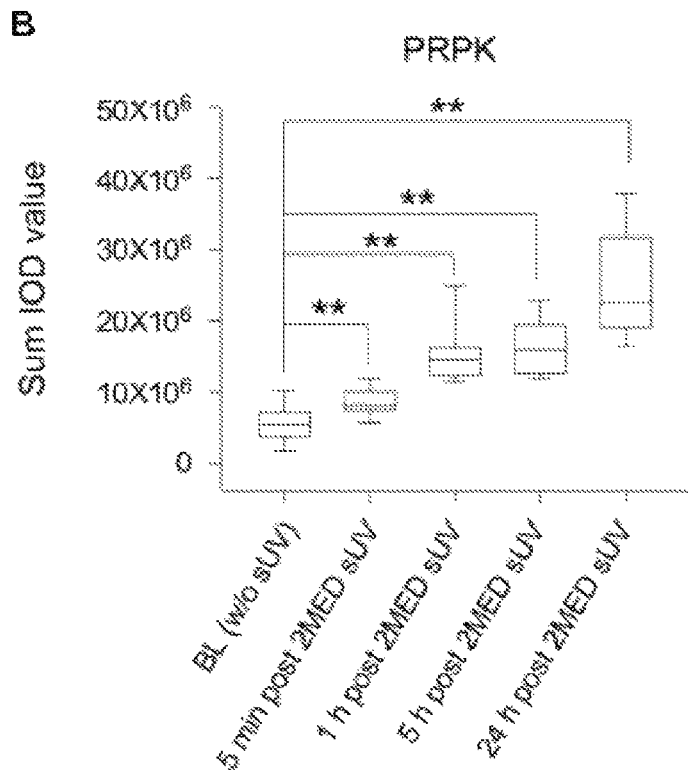
FIG. 12B is a chart comparing the expression of total PRPK in human skin harvested at various times after exposure to solar UV at a dose of 2 MED.
Figure 12C:
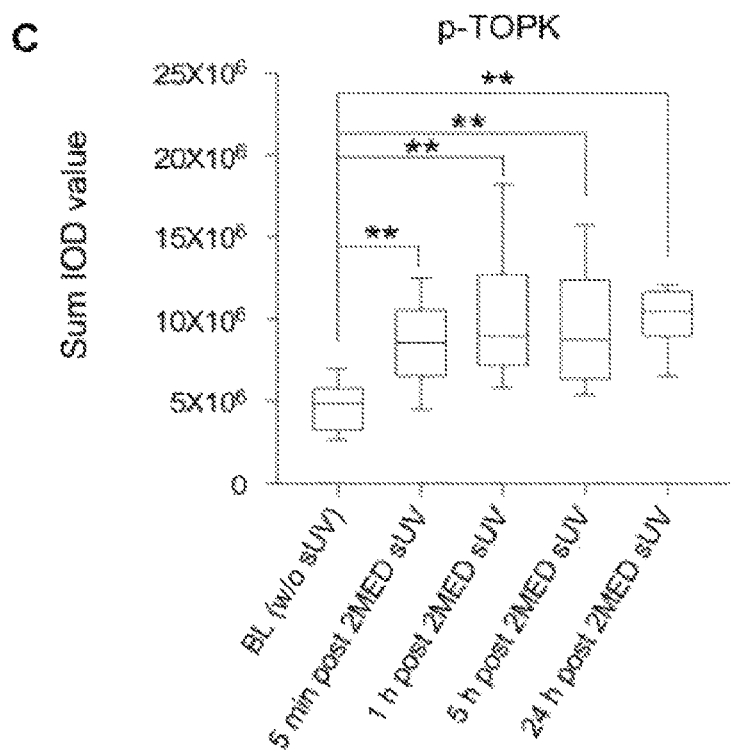
FIG. 12C is a chart comparing the expression of phosphorylated TOPK in human skin harvested at various times after exposure to solar UV at a dose of 2 MED.
Figure 12D:
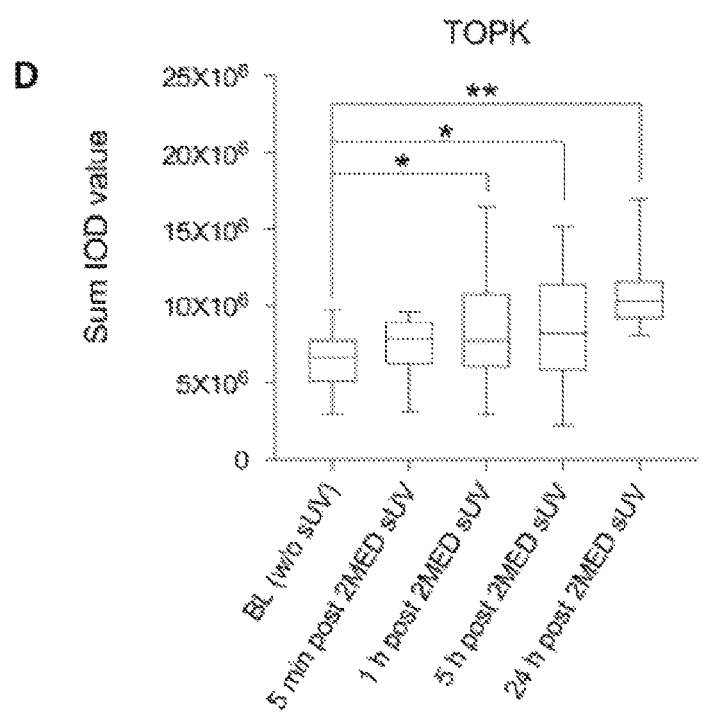
FIG. 12D is a chart comparing the expression of total TOPK in human skin harvested at various times after exposure to solar UV at a dose of 2 MED.

FIG. 12A is a chart comparing the expression of phosphorylated PRPK in human skin harvested at various times after exposure to solar UV at a dose of 2 MED. FIG. 12B is a chart comparing the expression of total PRPK in human skin harvested at various times after exposure to solar UV at a dose of 2 MED. FIG. 12C is a chart comparing the expression of phosphorylated TOPK in human skin harvested at various times after exposure to solar UV at a dose of 2 MED. FIG. 12D is a chart comparing the expression of total TOPK in human skin harvested at various times after exposure to solar UV at a dose of 2 MED. SSL exposure increased the expression of phosphorylated and total PRPK (FIGS. 12A and 12B) and TOPK (FIGS. 12C and 12D) in a time-dependent manner in human skin.

Example 7—Rocuronium Bromide Binds to PRPK and Inhibits PRPK Phosphorylation

Figure 13A:
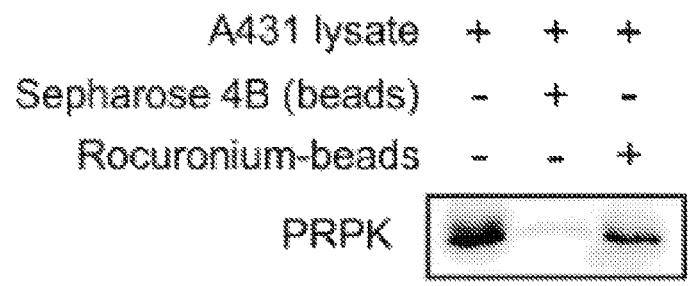
FIG. 13A is a photograph illustrating a chromatographic plate showing the interaction and binding of PRPK with rocuronium bromide in A431 cells.
Figure 13B:
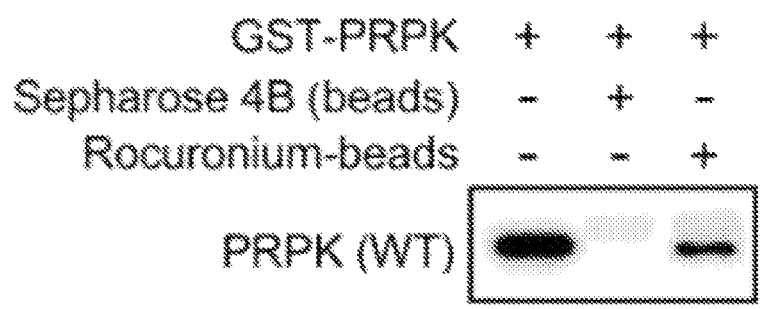
FIG. 13B is a photograph illustrating a chromatographic plate showing the interaction and binding of rocuronium bromide with wildtype PRPK recombinant GST protein.

The interaction between rocuronium bromide and PRPK, and the inhibition of PRPK phosphorylation by rocuronium bromide was evaluated. In vitro and ex vivo binding assays were conducted using GST-PRPK or A431 cell lysates and rocuronium bromide-conjugated Sepharose 4B beads. FIG. 13A is a photograph illustrating a chromatographic plate showing the interaction and binding of PRPK with rocuronium bromide in A431 cells. FIG. 13B is a photograph illustrating a chromatographic plate showing the interaction and binding of rocuronium bromide with wildtype PRPK recombinant GST protein. As seen in FIGS. 13A and 13B, rocuronium bromide binds to both GST-PRPK and PRPK in A431 lysates.

Figure 13C:
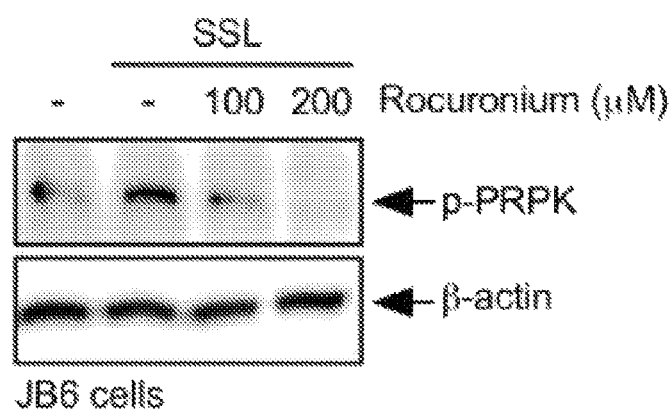
FIG. 13C is a photograph illustrating a chromatographic plate showing the reduction in SSL-induced phosphorylation of PRPK in JB6 cells with an increasing concentration of rocuronium bromide.

The effect of the binding of rocuronium bromide to PRPK on SSL-induced phosphorylation of PRPK was evaluated. FIG. 13C is a photograph illustrating a chromatographic plate showing the reduction in SSL-induced phosphorylation of PRPK in JB6 cells with increasing concentrations of rocuronium bromide, added into the medium. Thus, rocuronium bromide inhibited sUVL-induced phosphorylation of PRPK.

Figure 14A:
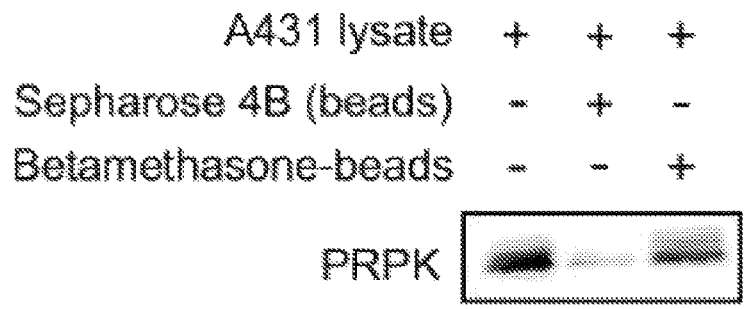
FIG. 14A is a photograph illustrating a chromatographic plate showing the interaction and binding of PRPK with betamethasone 17-valerate in A431 cells.
Figure 14B:
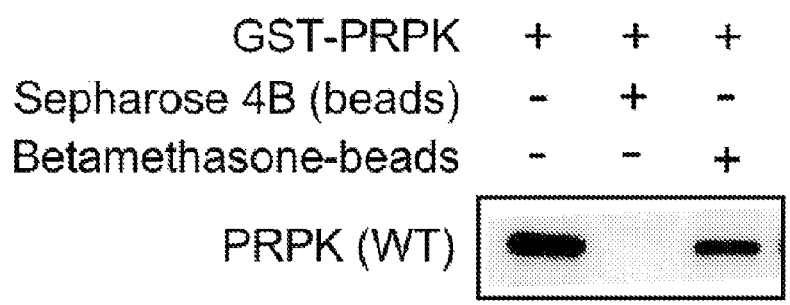
FIG. 14B is a photograph illustrating a chromatographic plate showing the interaction and binding of betamethasone 17-valerate with wildtype PRPK recombinant GST protein.

Example 8—Betamethasone 17-Valerate Binds to PRPK and Inhibits PRPK Phosphorylation The interaction between betamethasone 17-valerate and PRPK, and the inhibition of PRPK phosphorylation by betamethasone 17-valerate was evaluated. In vitro and ex vivo binding assays were conducted using recombinant GST-PRPK or A431 cell lysates and betamethasone 17-valerate-conjugated Sepharose 4B beads. FIG. 14A is a photograph illustrating a chromatographic plate showing the interaction and binding of PRPK with betamethasone 17-valerate in A431 cells. FIG. 14B is a photograph illustrating a chromatographic plate showing the interaction and binding of betamethasone 17-valerate with wildtype PRPK recombinant GST protein. As seen in FIGS. 14A and 14B, betamethasone 17-valerate binds to both recombinant GST-PRPK and PRPK in A431 lysates.

Figure 14C:
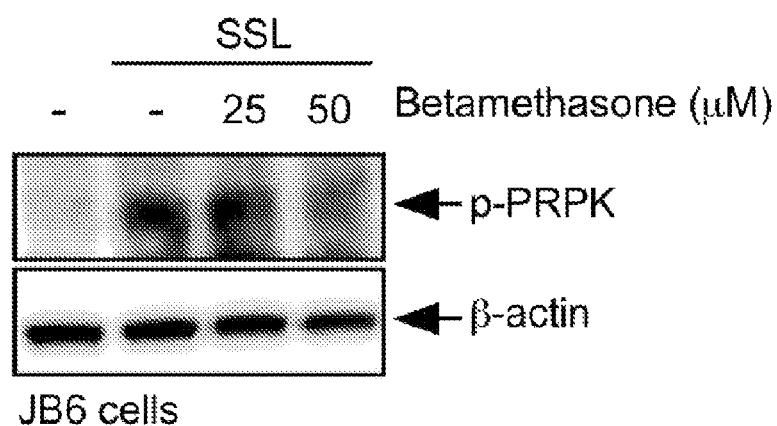
FIG. 14C is a photograph illustrating a chromatographic plate showing the reduction in SSL-induced phosphorylation of PRPK in JB6 cells with an increasing concentration of betamethasone 17-valerate.

The effect of the binding of betamethasone 17-valerate to PRPK on SSL-induced phosphorylation of PRPK was evaluated. FIG. 14C is a photograph illustrating a chromatographic plate showing the reduction in SSL-induced phosphorylation of PRPK in JB6 cells with an increasing concentration of betamethasone 17-valerate, added to the medium. Thus, betamethasone 17-valerate inhibited SSL-induced phosphorylation of PRPK.

Figure 15:
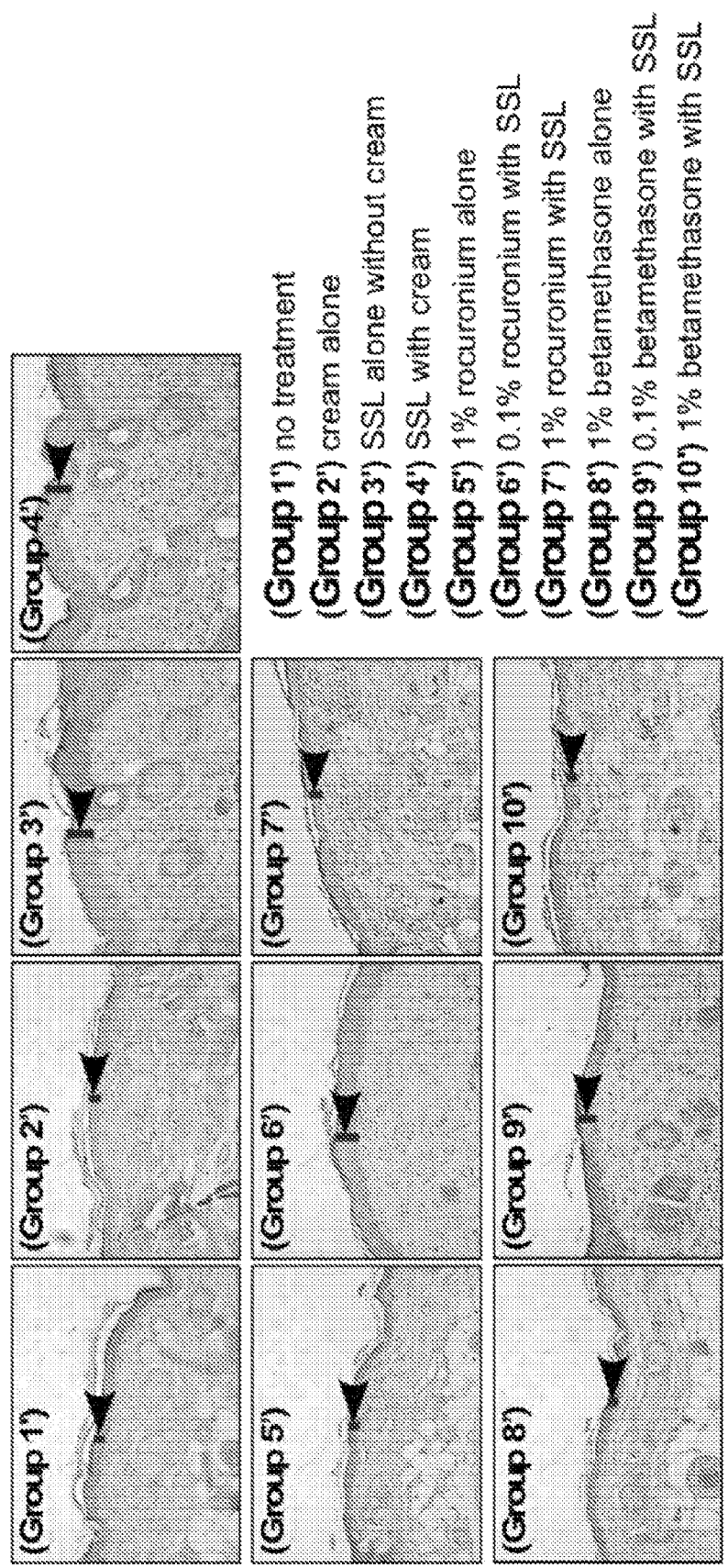
FIG. 15 is a photographic array comparing epidermal thickness in mouse skin samples exposed to one or more of SSL, rocuronium bromide, and betamethasone 17-valerate.
Figure 16:
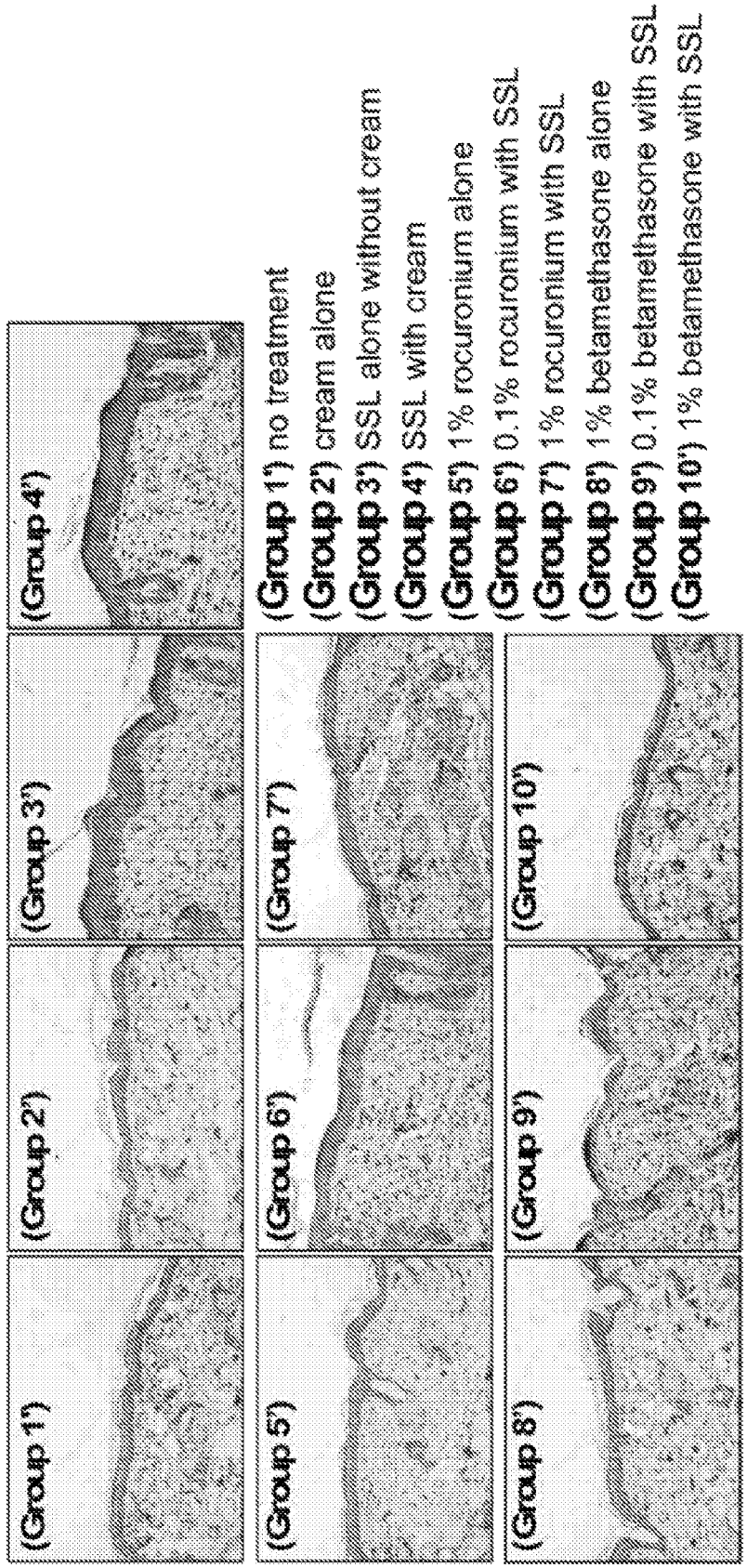
FIG. 16 is a photographic array comparing expression of phosphorylated PRPK in immunologically stained mouse skin samples exposed to one or more of SSL, rocuronium bromide, and betamethasone 14-valerate.

Example 9—Topical Treatment with Rocuronium Bromide or Betamethasone 17-Valerate Attenuates sUV-Induced Increases in Epidermal Thickness and PRPK Expression PRPK phosphorylation induced by sUV is a potent stimulator of skin inflammation. Inflammation contributes to tumor development and progression and metastasis often arises in acute and chronic inflammatory skin conditions and increased epidermal thickness is a sign of sUV-induced inflammatory responses. To examine the effect of rocuronium bromide on SSL-induced acute skin inflammation, H&E (haemotoxylin and eosin) staining on SSL-exposed skin tissues of SKH-1 hairless mouse skin was performed. FIG. 15 is a photographic array comparing epidermal thickness in mouse skin samples exposed to one or more of SSL, rocuronium bromide, and betamethasone 17-valerate. FIG. 16 is a photographic array comparing expression of phosphorylated PRPK in immunologically stained mouse skin samples exposed to one or more of SSL, rocuronium bromide, and betamethasone 14-valerate. A cream carrier was used to apply the rocuronium bromide or betamethasone 17-valerate. At 24 h after sUV (SSL) irradiation, SKH-1 hairless mouse skin exhibited increased epidermal thickness (FIG. 15) and increased PRPK expression (FIG. 16). In contrast, application of rocuronium bromide or betamethasone-17-valerate attenuated sUV-induced increases in epidermal thickness and PRPK expression compared to the untreated sUV-exposed group (FIGS. 15 and 16).

Figure 17:
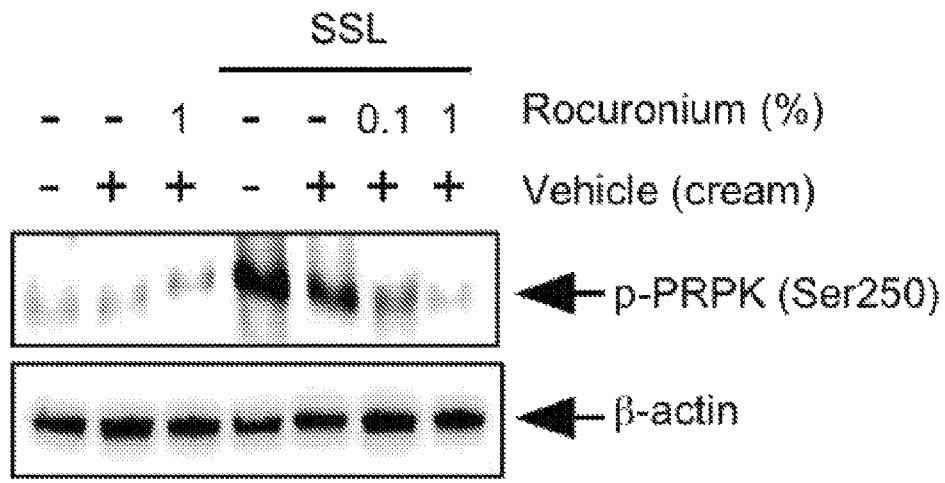
FIG. 17 is a photograph illustrating a chromatographic plate comparing the phosphorylation of PRPK in mouse skin tissue samples treated or not treated with rocuronium bromide and exposed or not exposed to SSL.
Figure 18:
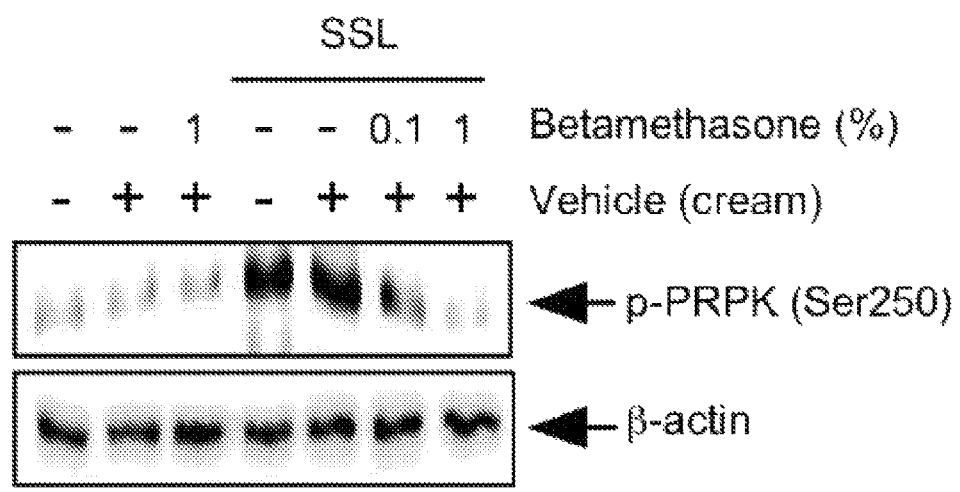
FIG. 18 is a photograph illustrating a chromatographic plate comparing the phosphorylation of PRPK in mouse skin tissue samples treated or not treated with betamethasone 17-valerate and exposed or not exposed to SSL.

FIG. 17 is a photograph illustrating a chromatographic plate comparing the phosphorylation of PRPK in mouse skin tissue samples treated or not treated with rocuronium bromide and exposed or not exposed to SSL. FIG. 18 is a photograph illustrating a chromatographic plate comparing the phosphorylation of PRPK in mouse skin tissue samples treated or not treated with betamethasone 17-valerate and exposed or not exposed to SSL. Topical treatment with rocuronium bromide (FIG. 17) or betamethasone-17-valerate (FIG. 18) decreased phosphorylation of PRPK in sUV-treated mouse skin. Increasing the concentration of rocuronium bromide or betamethasone-17-valerate further reduced sUV-induced phosphorylation phosphorylation (FIGS. 17 and 18).

Figure 19A:
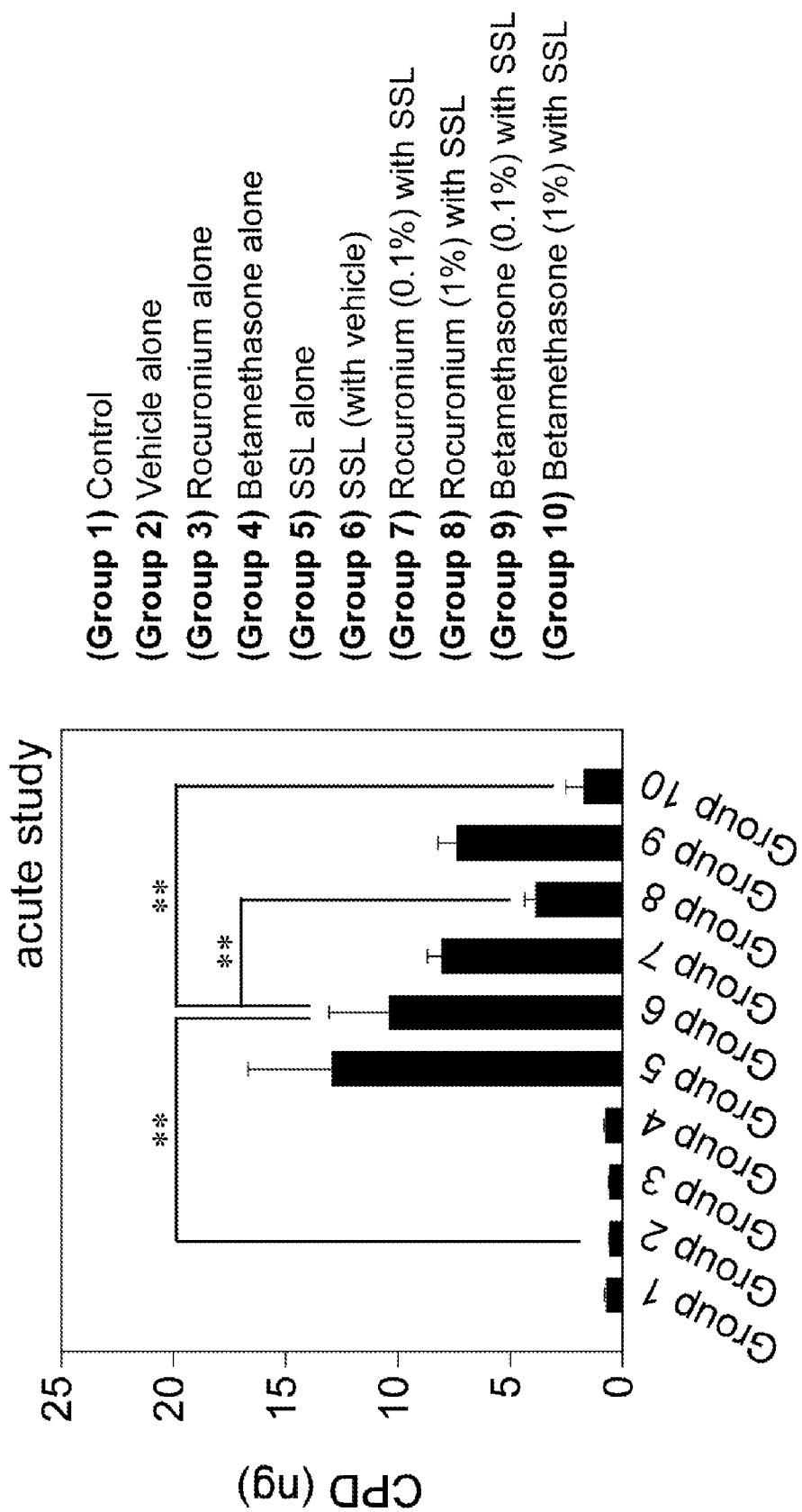
FIG. 19A is a chart comparing effect of rocuronium bromide treatment and betamethasone 17-valerate treatment on the formation of cyclobutene pyrimidine dimers (CPD) in skin tissues from SKH1 hairless mice exposed to acute SSL.
Figure 19B:
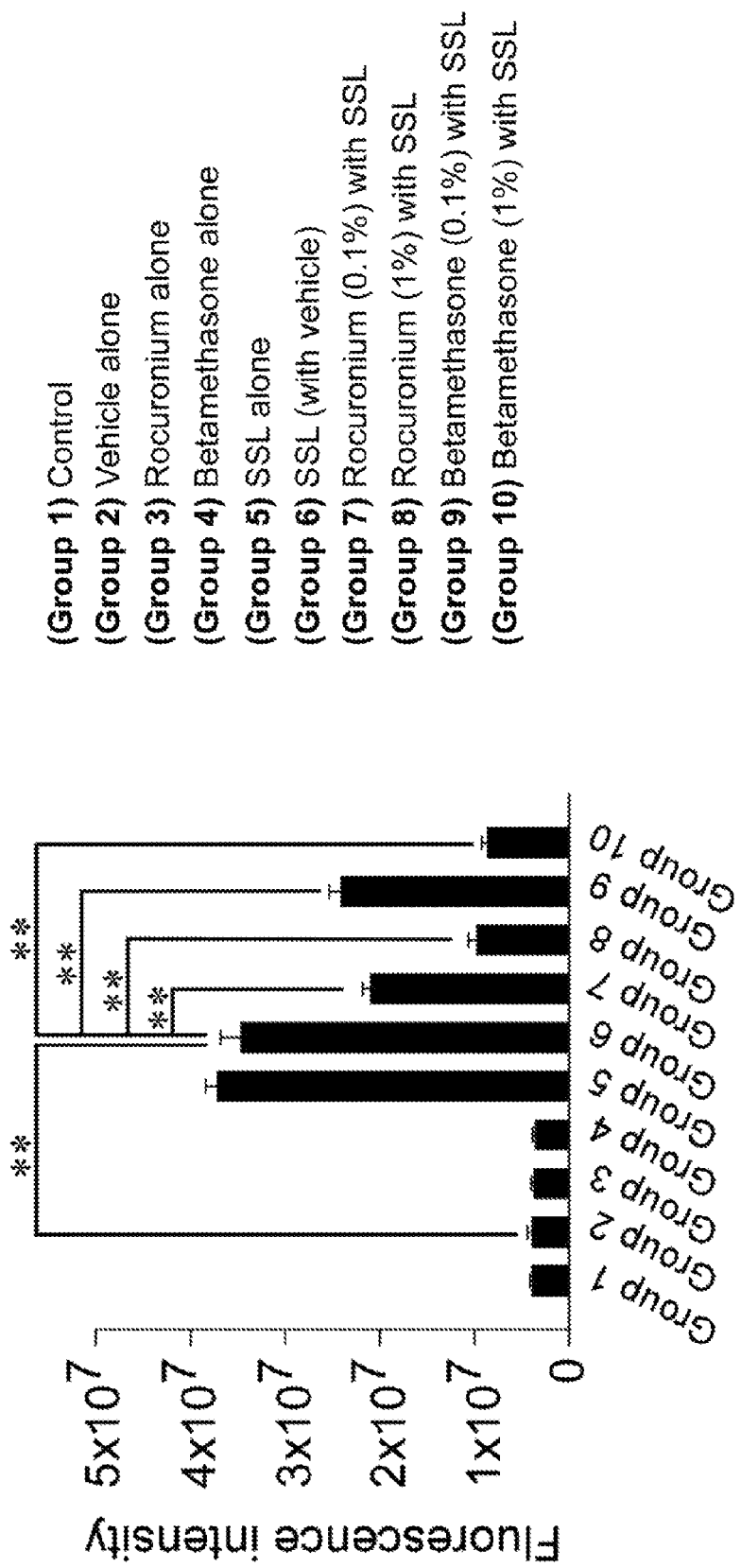
FIG. 19B is a chart comparing effect of rocuronium bromide treatment and betamethasone 17-valerate treatment on fluorescence intensity in skin tissues from SKH1 hairless mice exposed to acute SSL.
Figure 19D:
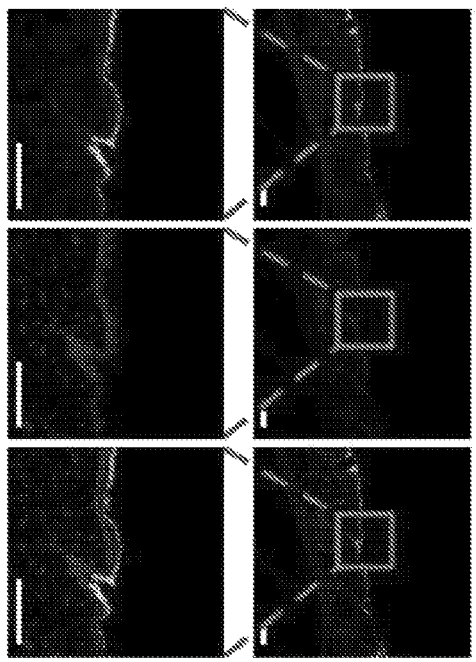
FIG. 19D is a photographic array comparing amount of CPD in immunologically stained mouse skin samples exposed only to a vehicle.
Figure 19C:
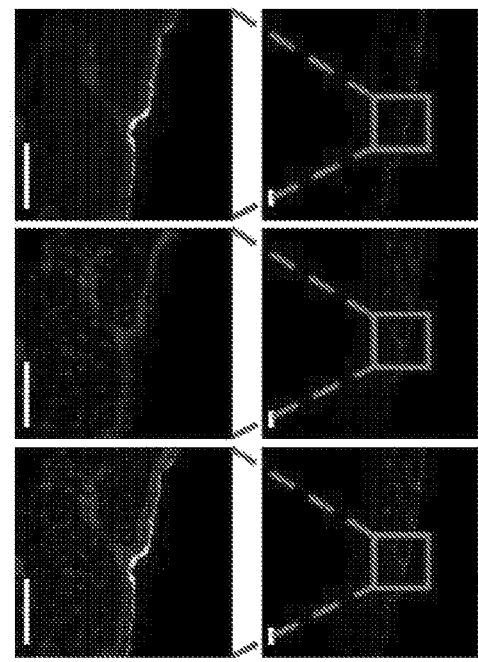
FIG. 19C is a photographic array comparing amount of CPD in immunologically stained control mouse skin samples.
Figure 19F:
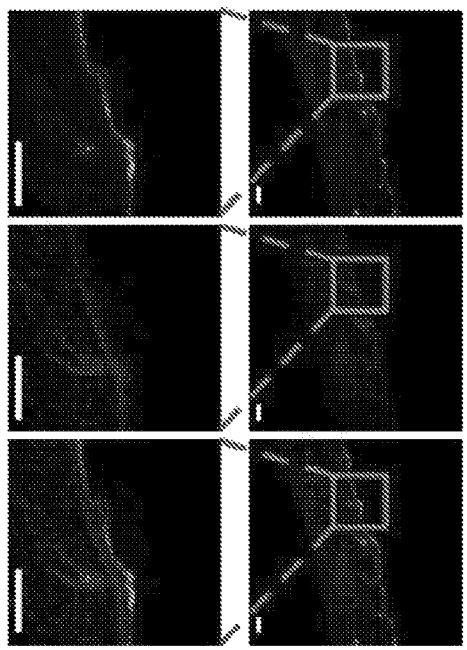
FIG. 19F is a photographic array comparing amount of CPD in immunologically stained mouse skin samples exposed to betamethasone 17-valerate alone.
Figure 19E:
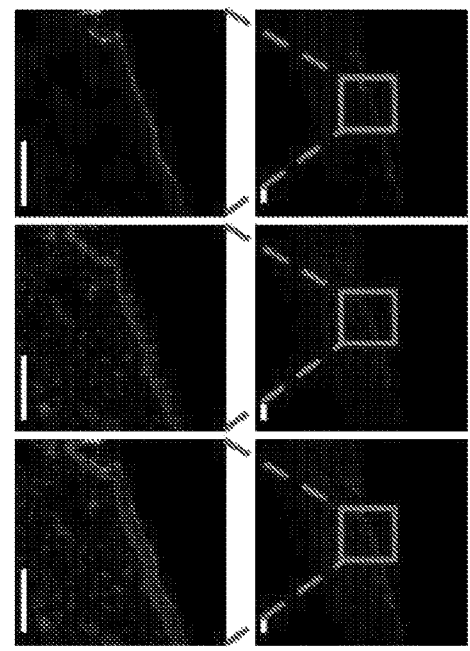
FIG. 19E is a photographic array comparing amount of CPD in immunologically stained mouse skin samples exposed to rocuronium bromide alone.
Figure 19G:
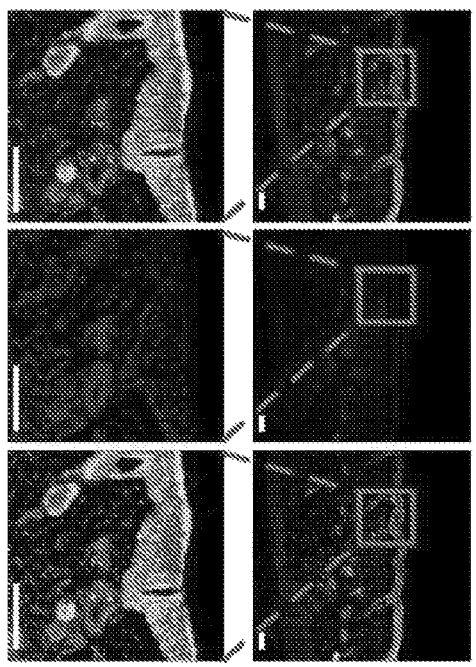
FIG. 19G is a photographic array comparing amount of CPD in immunologically stained mouse skin samples exposed to SSL alone.
Figure 19H:
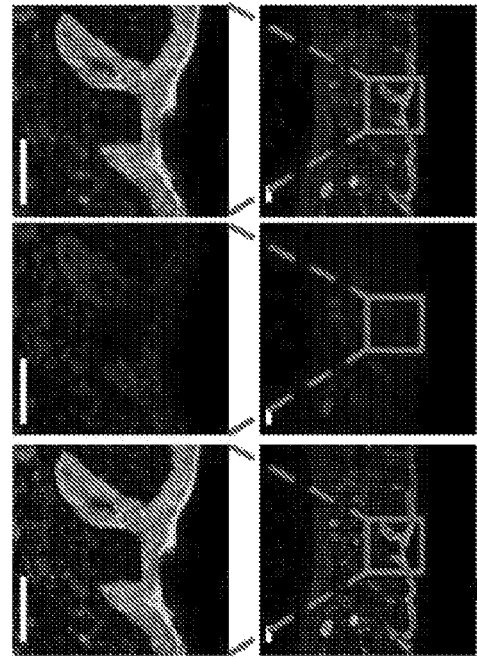
FIG. 19H is a photographic array comparing amount of CPD in immunologically stained mouse skin samples exposed to SSL with the vehicle.
Figure 19J:
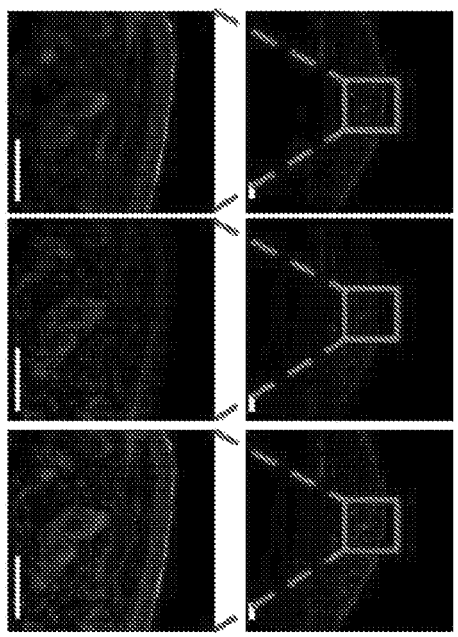
FIG. 19J is a photographic array comparing amount of CPD in immunologically stained mouse skin samples exposed to 1% rocuronium bromide with SSL
Figure 19I:
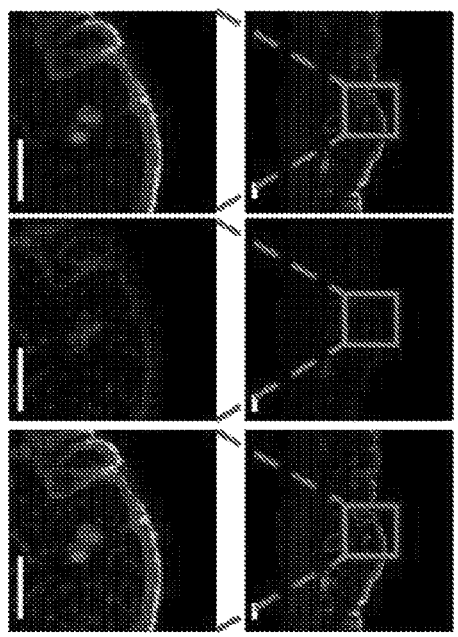
FIG. 19I is a photographic array comparing amount of CPD in immunologically stained mouse skin samples exposed to 0.1% rocuronium bromide with SSL.
Figure 19L:
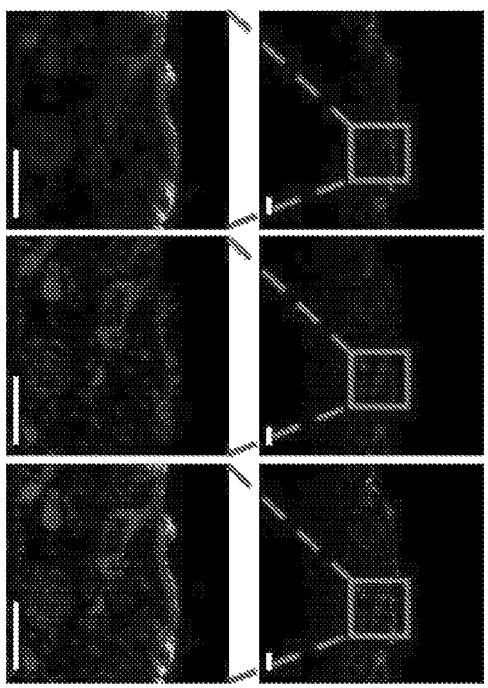
FIG. 19L is a photographic array comparing amount of CPD in immunologically stained mouse skin samples exposed to 1% betamethasone 17-valerate with SSL.
Figure 19K:
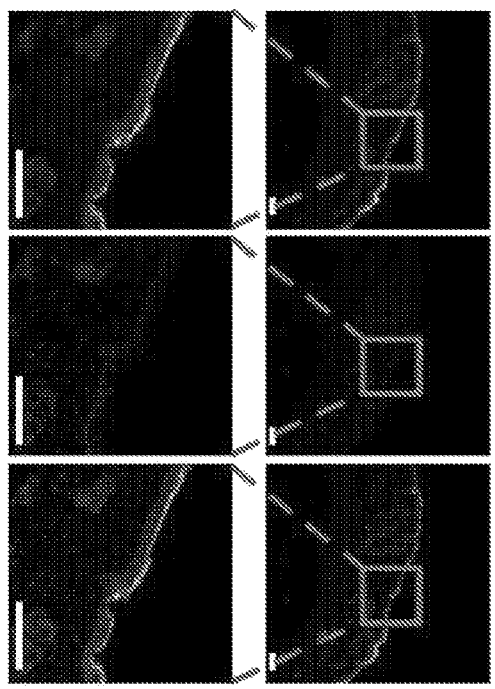
FIG. 19K is a photographic array comparing amount of CPD in immunologically stained mouse skin samples exposed to 0.1% betamethasone 17-valerate with SSL.

Example 10—Topical Treatment with Rocuronium Bromide or Betamethasone 17-Valerate Reduces sUV-Induced CPD Production The effect of rocuronium bromide treatment and betamethasone 17-valerate treatment on the formation of cyclobutene pyrimidine dimers was evaluated. sUV-induced DNA damage, predominantly observed as the formation of cyclobutane pyrimidine dimers (CPD), is recognized as an important molecular trigger for the initiation of sUV-induced immunosuppression and carcinogenesis in the skin. FIG. 19A is a chart comparing effect of rocuronium bromide treatment and betamethasone 17-valerate treatment on the formation of cyclobutene pyrimidine dimers in skin tissues from SKH1 hairless mice exposed to acute SSL. FIG. 19C is a photographic array comparing amount of CPD in immunologically stained control mouse skin samples. FIG. 19D is a photographic array comparing amount of CPD in immunologically stained mouse skin samples exposed only to a vehicle. FIG. 19E is a photographic array comparing amount of CPD in immunologically stained mouse skin samples exposed to rocuronium bromide alone. FIG. 19F is a photographic array comparing amount of CPD in immunologically stained mouse skin samples exposed to betamethasone 17-valerate alone. FIG. 19G is a photographic array comparing amount of CPD in immunologically stained mouse skin samples exposed to SSL alone. FIG. 19H is a photographic array comparing amount of CPD in immunologically stained mouse skin samples exposed to SSL with the vehicle. FIG. 19I is a photographic array comparing amount of CPD in immunologically stained mouse skin samples exposed to 0.1% rocuronium bromide with SSL. FIG. 19J is a photographic array comparing amount of CPD in immunologically stained mouse skin samples exposed to 1% rocuronium bromide with SSL. FIG. 19K is a photographic array comparing amount of CPD in immunologically stained mouse skin samples exposed to 0.1% betamethasone 17-valerate with SSL. FIG. 19L is a photographic array comparing amount of CPD in immunologically stained mouse skin samples exposed to 1% betamethasone 17-valerate with SSL.

As seen in FIGS. 19A to 19L, rocuronium bromide treatment and betamethasone 17-valerate treatment reduced sUV-induced CPD production in mice.

Example 11—Topical Treatment with Rocuronium Bromide or Betamethasone 17-Valerate Reduced SSL-Induced Skin Carcinogenesis in Mouse Models The effectiveness of rocuronium bromide (EXAMPLES 11 and 12) and betamethasone 17-valerate (EXAMPLE 13) in mouse models of chronic sUV-induced skin carcinogenesis was evaluated. Female SKH-1 hairless mice (5 weeks old, Charles River, Burlington, MA) were used. Skin carcinogenesis was induced by SSL-irradiation source lamps. At week 1, the SSL dose was 37 $kJ/m^2$ UVA and 1.8 $kJ/m^2$ UVB applied 3 times per week. The dose of SSL was gradually increased at a rate of 10% per week. At week 6, the dose was 60 $kJ/m^2$ UVA and 2.9 $kJ/m^2$ UVB and this dose was maintained until week 15. For topical treatment to the dorsal mouse skin, cream (oil-in-water emulsions) containing 0.1% or 1% (0.1 or 1 mg in 100 µl) of rocuronium bromide or betamethasone 17-valerate were prepared. The models included early-stage prevention models (EXAMPLE 11) and a late-stage prevention models (EXAMPLES 12 and 13). In the early-stage model, cream alone or cream containing rocuronium bromide or betamethasone 17-valerate was applied for 29 weeks (3×Wk) to the dorsal area of the SKH-1 hairless mouse skin, posterior to the base of the neck and anterior to the base of the tail before exposure to the dose of SSL irradiation on same day. SSL treatment was for 15 weeks and the drug cream was continued for 29 weeks. In the late-stage model, mice received SSL for 15 weeks at which time they began receiving topical application with rocuronium bromide or betamethasone 17-valerate. For the early stage model, SKH-1 hairless mice were divided into groups as follows: Groups 1 and 2 were negative control groups, untreated and treated with only cream vehicle with no SSL exposure; Group 3=1% rocuronium bromide; Group 4=SSL alone without cream; Group 5=SSL with cream only; Group 6=0.1% rocuronium bromidein cream with SSL; Group 7=1% rocuronium bromide in cream with SSL. For the late stage models, groups were as follows: Groups 8 and 9 were negative control groups, untreated and treated with only cream vehicle with no SSL exposure; Group 10=1% rocuronium bromide only; Group 11=1% betamethasone 17-valerate only; Group 12=SSL alone with cream; Group 13=SSL with 0.1% rocuronium bromide; Group 14=1% rocuronium bromide in cream with SSL; Group 15=0.1% betamethasone 17-valerate in cream with SSL; and Group 16=1% rocuronium bromide or betamethasone 17-valerate in cream with SSL. An antibiotic ointment was applied to the eyes of each mouse prior to SSL exposure and body weight and tumor volume were measured each week.

Figure 20A:
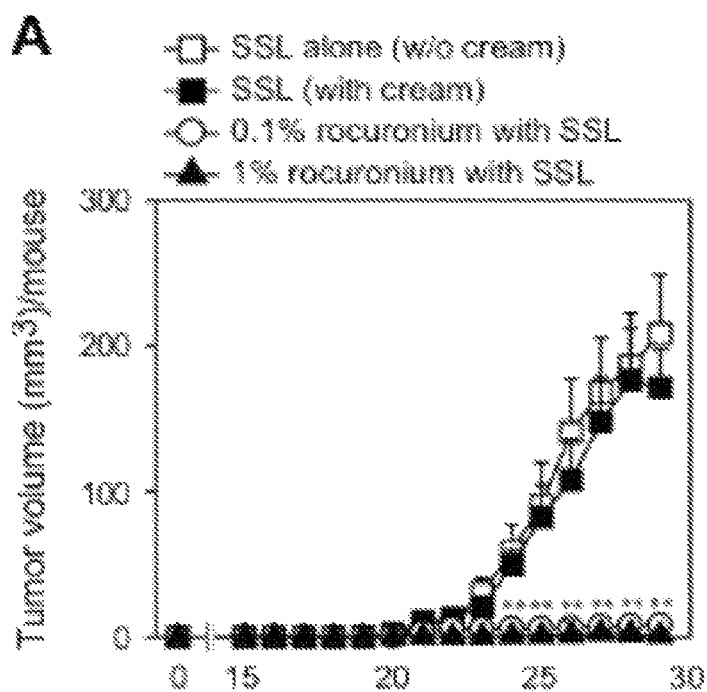
FIG. 20A is a chart comparing average tumor volume over time in an early-stage SSL-induced mouse model for mice topically treated or not treated with rocuronium bromide.
Figure 20B:
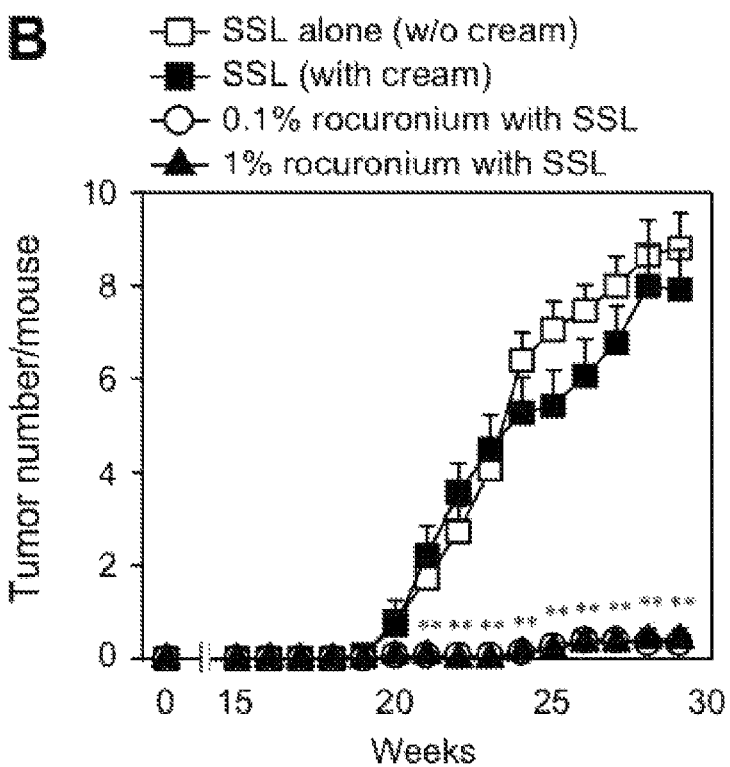
FIG. 20B is a chart comparing average tumor number over time in an early-stage SSL-induced mouse model for mice topically treated or not treated with rocuronium bromide.
Figure 20C:
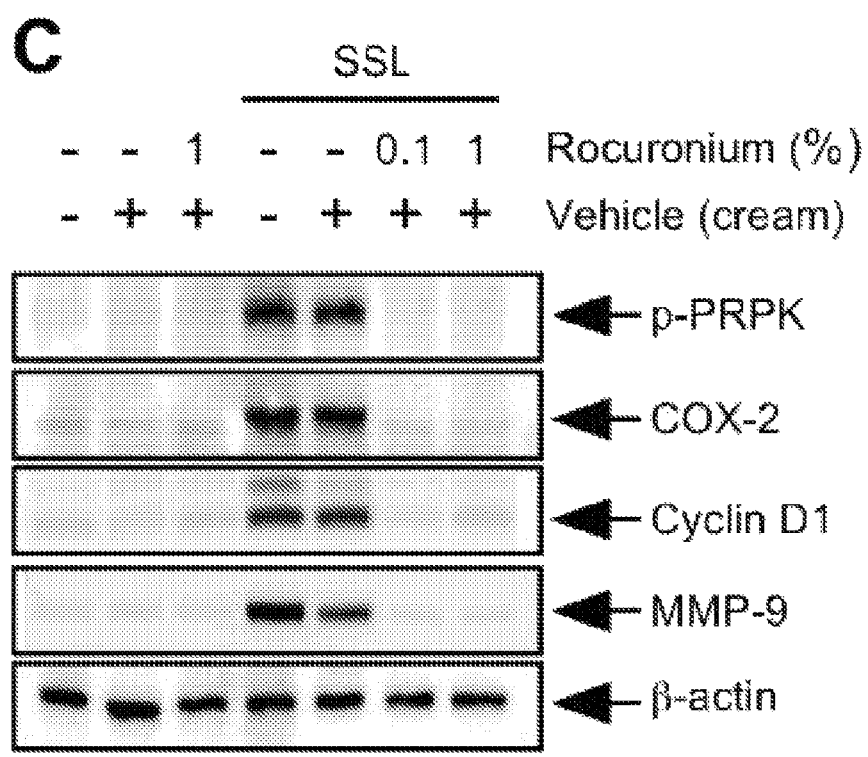
FIG. 20C is a photograph illustrating a chromatographic plate showing the effect of topical rocuronium bromide treatment on the expression of phosphorylated PRPK in early-stage SSL-induced SKH-1 hairless mouse skin tissue samples.

FIG. 20A is a chart comparing average tumor volume over time in an early-stage SSL-induced mouse model for mice topically treated or not treated with rocuronium bromide. FIG. 20B is a chart comparing average tumor number over time in an early-stage SSL-induced mouse model for mice topically treated or not treated with rocuronium bromide. FIG. 20C is a photograph illustrating a chromatographic plate showing the effect of topical rocuronium bromide treatment on the expression of phosphorylated PRPK in early-stage SSL-induced SKH-1 hairless mouse skin tissue samples. As seen in FIGS. 20A, 20B, and 20C, topical treatment with rocuronium bromide reduced SSL-induced skin carcinogenesis in early-stage mouse models.

Figure 21A:
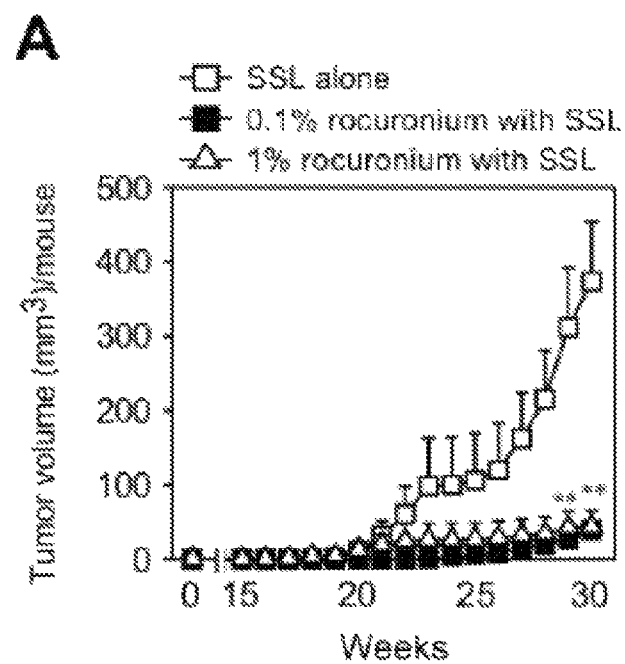
FIG. 21A is a chart comparing average tumor volume over time in a late-stage SSL-induced mouse model for mice topically treated or not treated with rocuronium bromide.
Figure 21B:
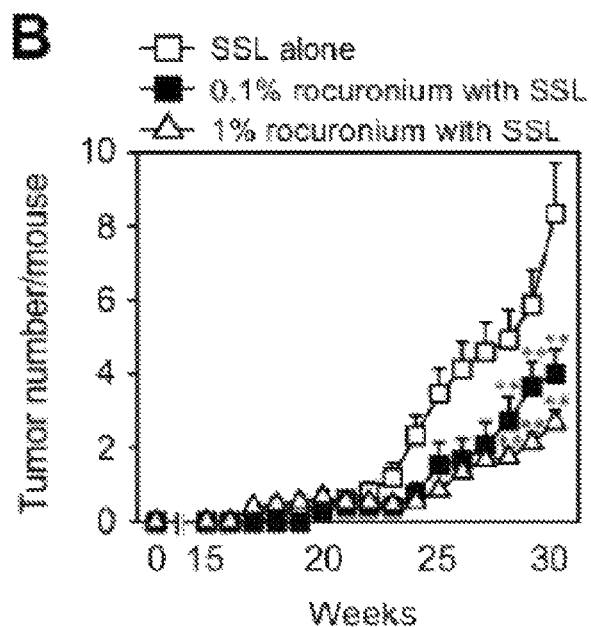
FIG. 21B is a chart comparing average tumor number over time in a late-stage SSL-induced mouse model for mice topically treated or not treated with rocuronium bromide.
Figure 21C:
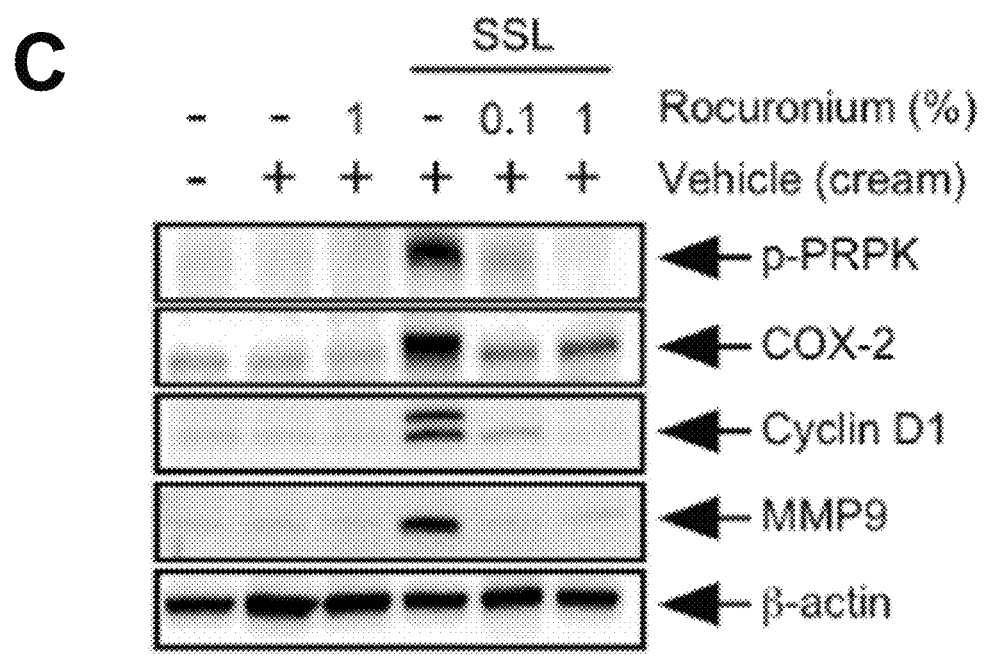
FIG. 21C is a photograph illustrating a chromatographic plate showing the effect of topical rocuronium bromide treatment on the expression of COX-2, cyclin D1, MMP9 and phosphorylated PRPK in late-stage SSL-induced SKH-1 hairless mouse skin tissue samples.

FIG. 21A is a chart comparing average tumor volume over time in a late-stage SSL-induced mouse model for mice topically treated or not treated with rocuronium bromide. FIG. 21B is a chart comparing average tumor number over time in a late-stage SSL-induced mouse model for mice topically treated or not treated with rocuronium bromide. FIG. 21C is a photograph illustrating a chromatographic plate showing the effect of topical rocuronium bromide treatment on the expression of COX-2, cyclin D1, MMP9 and phosphorylated PRPK in late-stage SSL-induced SKH-1 hairless mouse skin tissue samples. As seen in FIGS. 21A, 21B, and 21C, topical treatment with rocuronium bromide reduced SSL-induced skin carcinogenesis in late-stage mouse models. Thus, topical treatment with rocuronium bromide decreased SSL-induced skin carcinogenesis in both the early-stage and late-stage prevention models. Both tumor volume (FIGS. 20A and 21A) and tumor number (FIGS. 20B and 21B) were decreased by rocuronium bromide treatment. Rocuronium bromide also suppressed levels of COX-2, cyclin D1, MMP-9 and phosphorylated PRPK in SKH-1 hairless mouse skin (FIGS. 20C, 21C).

Figure 22A:
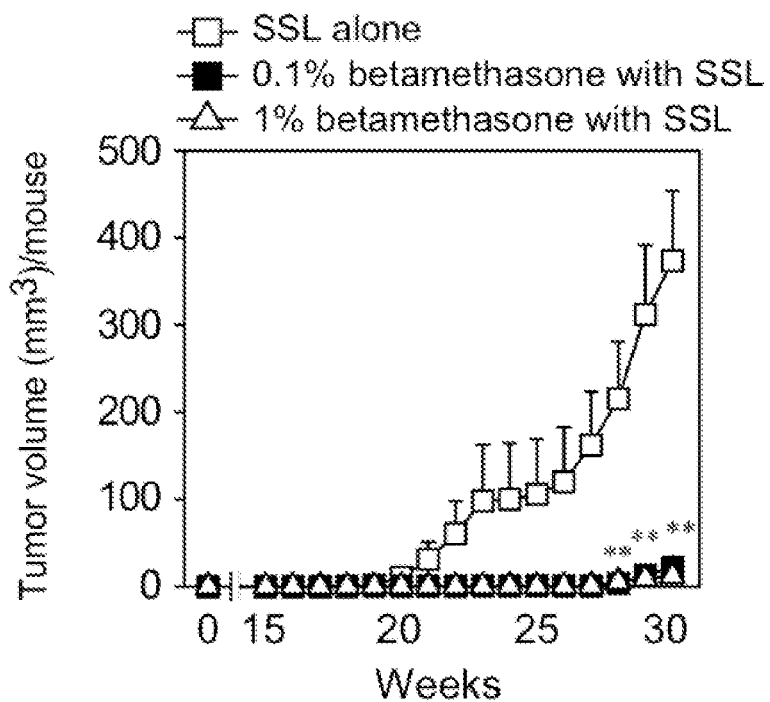
FIG. 22A is a chart comparing average tumor volume over time in a late-stage SSL-induced mouse model for mice topically treated or not treated with betamethasone 17-valerate.
Figure 22B:
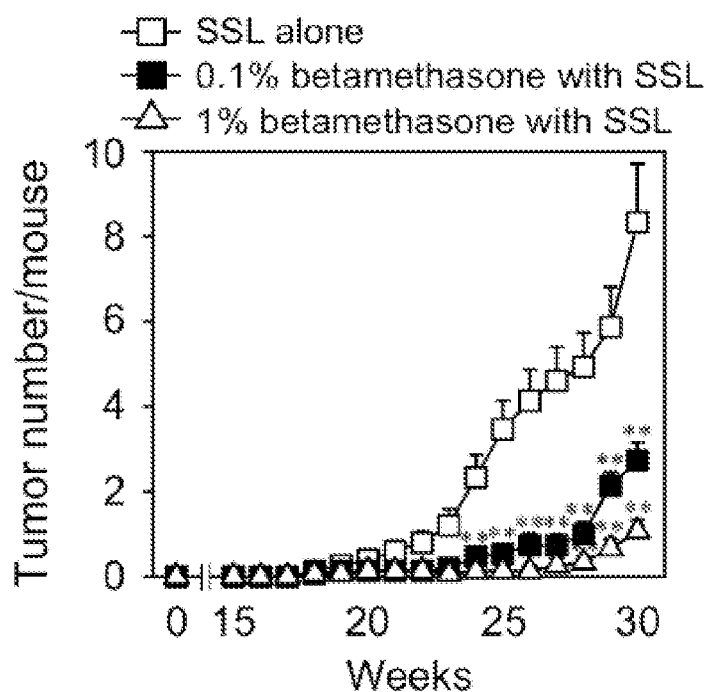
FIG. 22B is a chart comparing average tumor number over time in a late-stage SSL-induced mouse model for mice topically treated or not treated with betamethasone 17-valerate.
Figure 22C:
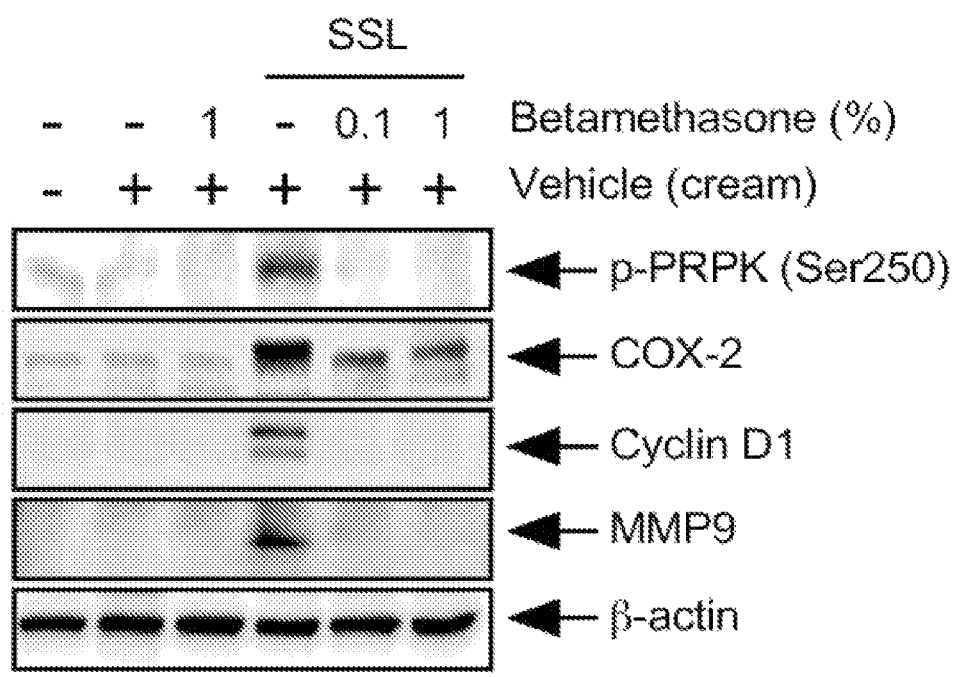
FIG. 22C is a photograph illustrating a chromatographic plate showing the effect of topical betamethasone 17-valerate treatment on the expression of COX-2, cyclin D1, MMP0 and phosphorylated PRPK in late-stage SSL-induced SKH-1 hairless mouse skin cells.

FIG. 22A is a chart comparing average tumor volume over time in a late-stage SSL-induced mouse model for mice topically treated or not treated with betamethasone 17-valerate. FIG. 22B is a chart comparing average tumor number over time in a late-stage SSL-induced mouse model for mice topically treated or not treated with betamethasone 17-valerate. FIG. 22C is a photograph illustrating a chromatographic plate showing the effect of topical betamethasone 17-valerate treatment on the expression of COX-2, cyclin D1, MMP0 and phosphorylated PRPK in late-stage SSL-induced SKH-1 hairless mouse skin cells. As seen in FIGS. 22A, 22B, and 22C, topical treatment with betamethasone 17-valerate reduced SSL-induced skin carcinogenesis in late-stage mouse models.

Figure 23:
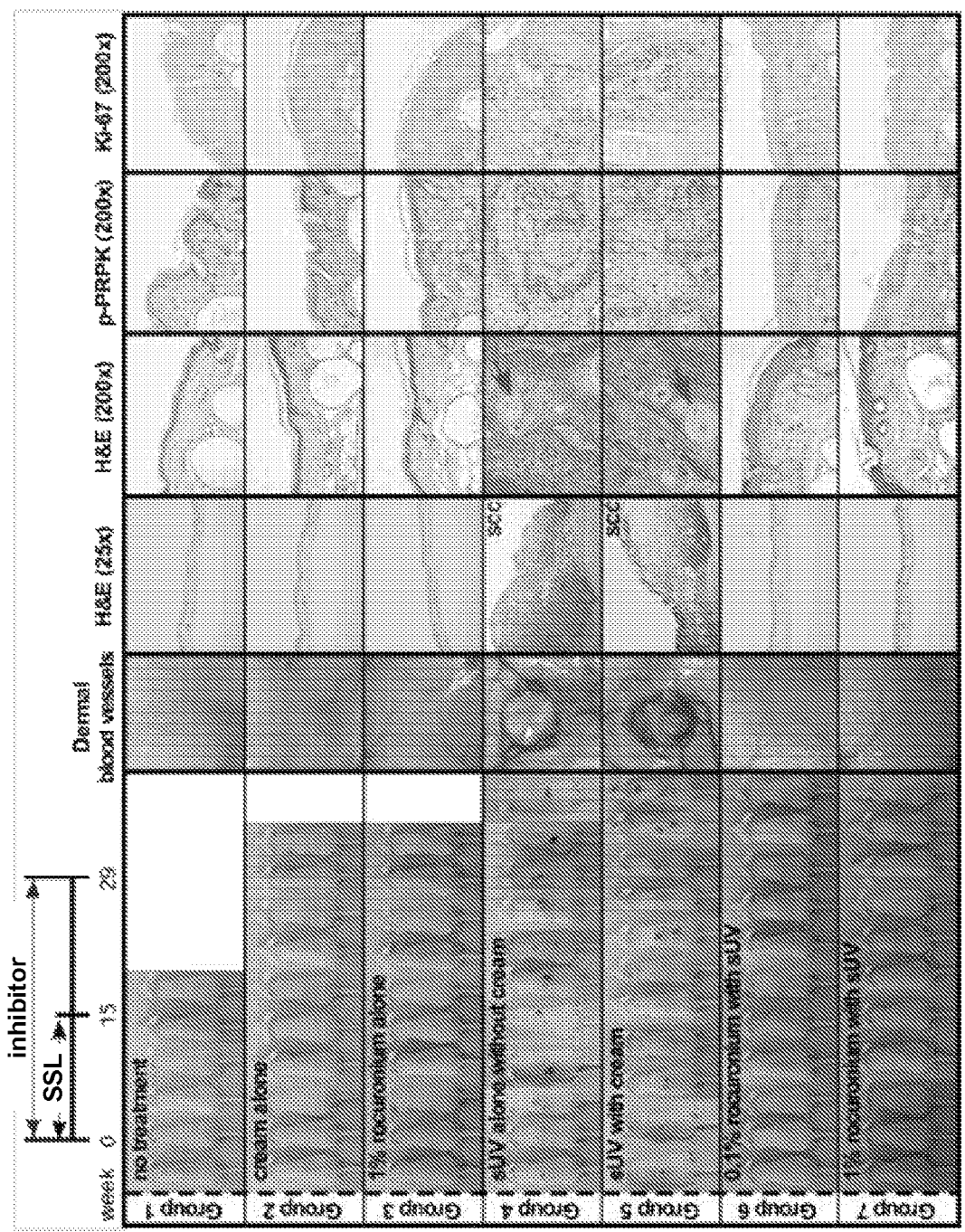
FIG. 23 is a photographic array showing the effectiveness of topical rocuronium bromide treatment in preventing cancer in an early-stage SSL-induced prevention model.
Figure 24A:
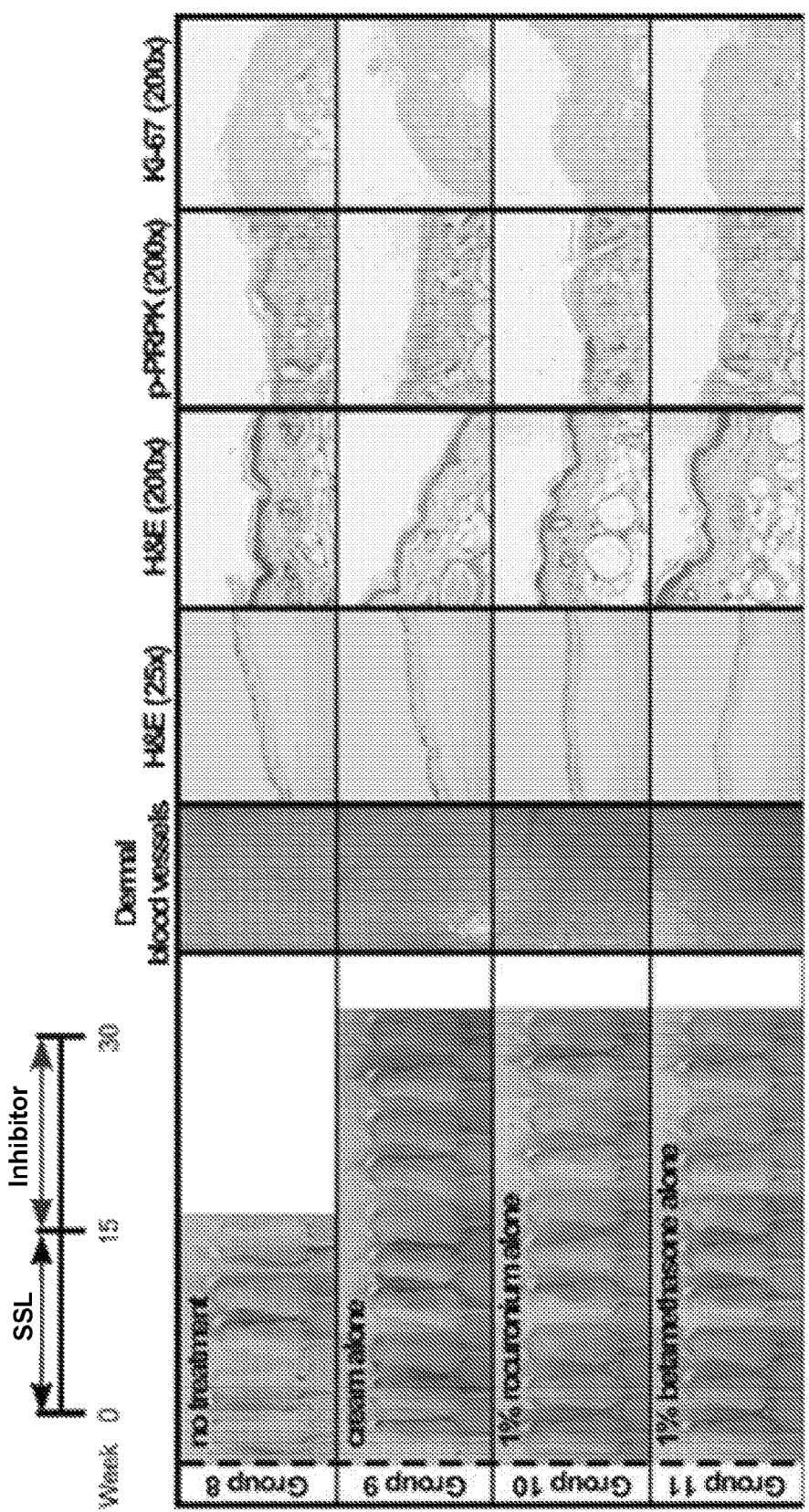
FIGS. 24A and 24B are photographic arrays showing the effectiveness of topical rocuronium bromide treatment or betamethasone 17-valerate treatment in preventing cancer in a late-stage SSL-induced prevention model.
Figure 24B:
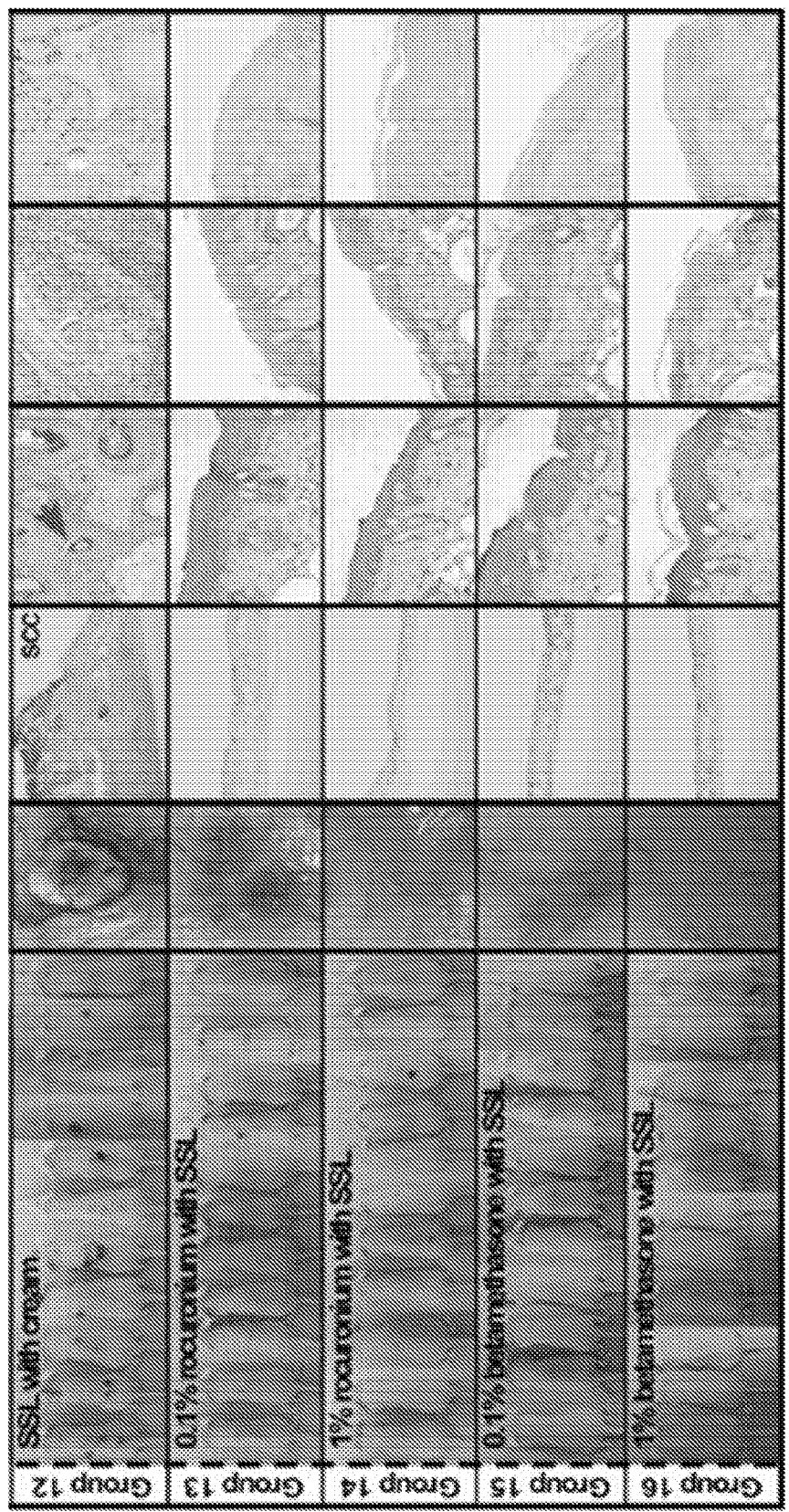

Both mouse models showed an increased number of large tortuous blood vessels in the dermis of the SSL treated group compared with untreated group. FIG. 23 is a photographic array showing the effectiveness of topical rocuronium bromide treatment in preventing cancer in an early-stage SSL-induced prevention model. FIGS. 24A and 24B are photographic arrays showing the effectiveness of topical rocuronium bromide treatment or betamethasone 17-valerate treatment in preventing cancer in a late-stage SSL-induced prevention model. As seen in FIGS. 23, 24A, and 24B, topical treatment with rocuronium bromide or betamethasone 17-valerate inhibited SSL-induced neovascularization in tumor areas. Chronic SSL irradiation induced both papilloma formation and invasive cSCC and chronic solar UV exposure caused large epidermal changes and dermal invasion and the formation of abundant keratin pearls was also observed in the SSL-treated groups. Rocuronium bromide and betamethasone 17-valerate inhibited PRPK phosphorylation and Ki-67 expression (FIGS. 23, 24A, and 24B).

Example 12—Topical Treatment with Rocuronium Bromide or Betamethasone 17-Valerate Rescues SSL-Increased Immunosuppression by Up-Regulating IFN-γ and IL-12 and Down-Regulating PGE2

Exposure to UV radiation suppresses the immune response and UV-induced immune suppression is a major risk factor for skin cancer. In particular, UV exposure induces the production of Th2-associated cytokines and interferes with antigen presentation to Th1 cells producing IFN-γ. To determine whether rocuronium bromide or betamethasone 17-valerate affects the immune system response, the level of immune system markers, including interferon-γ (IFN-γ), interleukin-12 (IL-12) and prostaglandin E2 (PGE2), in mouse serum and the T-cell markers, CD3 and CD4, were examined. CD3 is associated with the T-cell receptor (TCR) and is essential in signal transduction in T cells following TCR activation. Tumor microenvironment-mediated down-regulation of TCR-associated signaling leads to the inhibition of T cell function and antitumor immunity in the tumor-bearing host. Very few T cells are observed in the epidermis and dermis of solar UV-induced SCCs. Treatment with rocuronium bromide or betamethasone 17-valerate revealed dense T cell infiltrates in mouse skin, and rocuronium bromide and betamethasone 17-valerate was potentially associated with activation of T cell function in dermis and epidermis of skin.

Figure 25A:
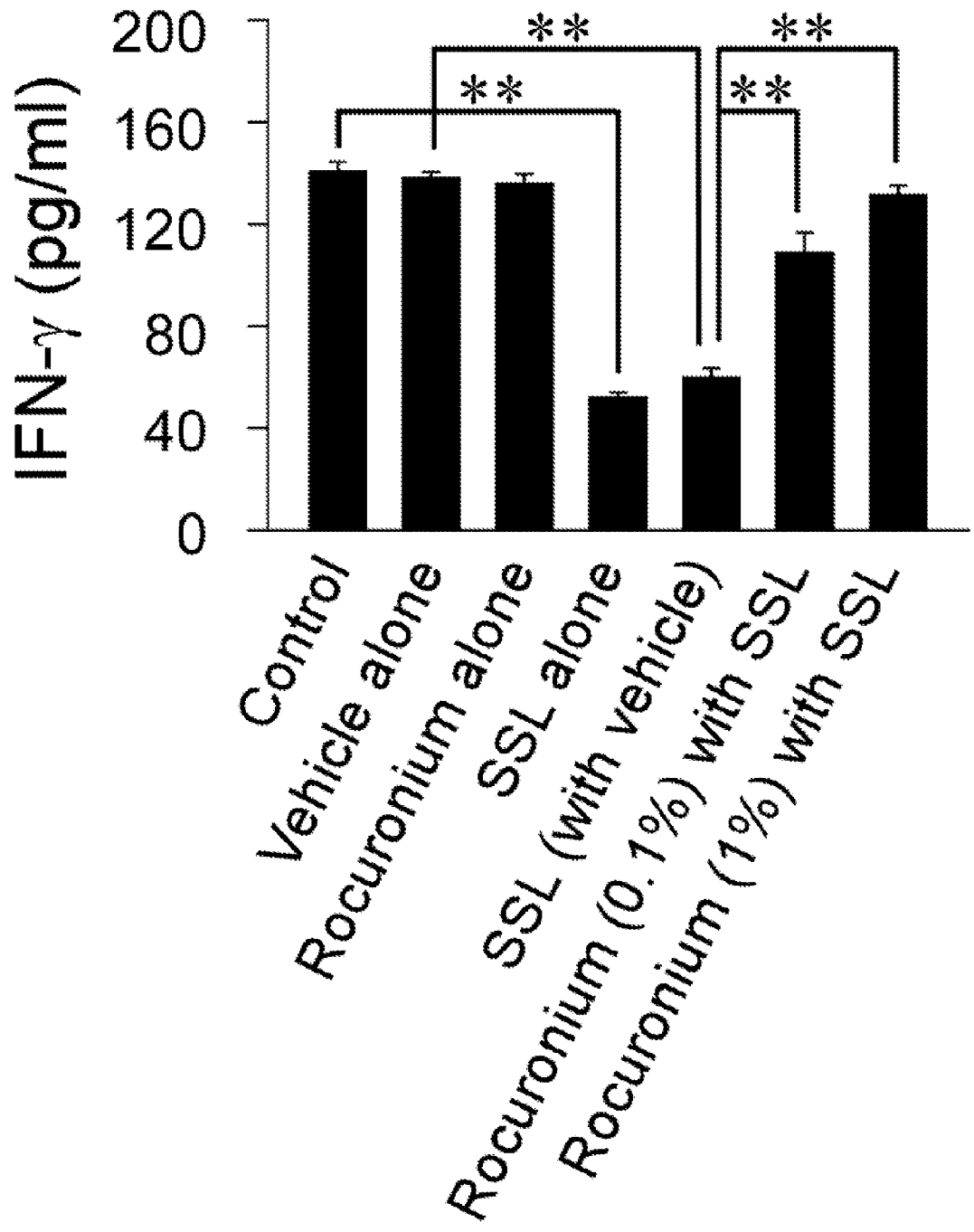
FIG. 25A is a chart comparing the effect of rocuronium bromide treatment on enhancement of IFN-γ production by immune cells in an early-stage SSL-induced prevention model.

SSL-induced immunosuppressive responses are associated with production of Th2-related cytokines (IL-10) and disturbance of antigen presentation to Th1 cells producing IFN-γ. Therefore, SSL-induced immunosuppression could be prevented by the Th1 cytokine, IFN-γ. An enzyme-linked immunosorbent assay (ELISA) was performed to examine IFN-γ levels in mouse serum. FIG. 25A is a chart comparing the effect of rocuronium bromide treatment on enhancement of IFN-γ production by immune cells in an early-stage SSL-induced prevention model. IL-12 is an immunoregulatory cytokine to reverse UV-induced DNA damage and immunosuppression, and also regulates the function and development of Th1 type cells by stimulating IFN-γ production. Furthermore, treatment with recombinant IL-12 reversed the UV-induced immunosuppression. Additionally, PGE2 plays a key role as an activator of UV-induced immunosuppression through its down-regulation of the levels of IL-12. Thus, the effects of PRPK inhibitors on SSL-induced changes on the immunoregulatory cytokines, IL-12 and PGE2, were investigated.

Figure 25B:
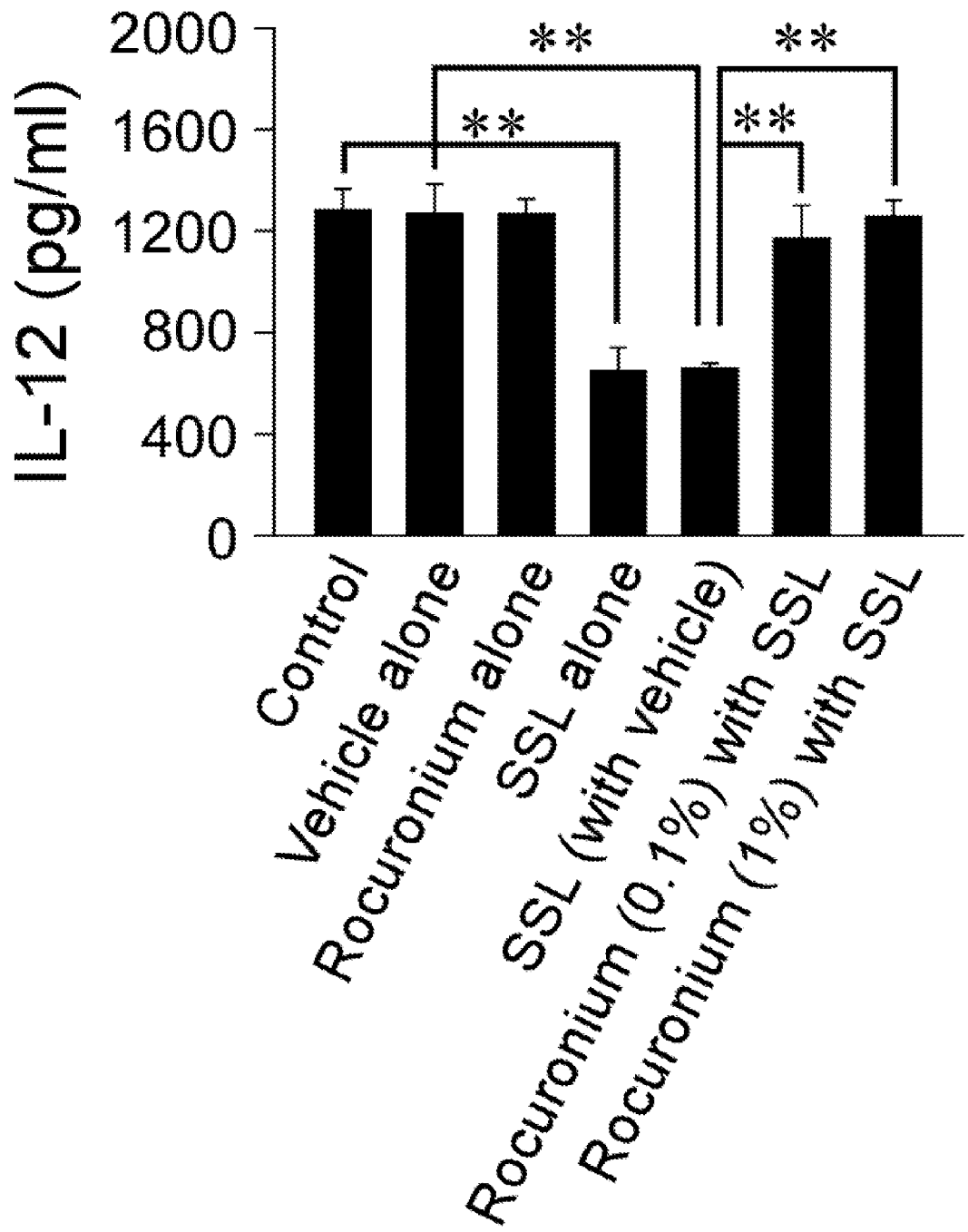
FIG. 25B is a chart comparing the effect of rocuronium bromide treatment on enhancement of IL-12 production in mouse serum in an early-stage SSL-induced prevention model.
Figure 25C:
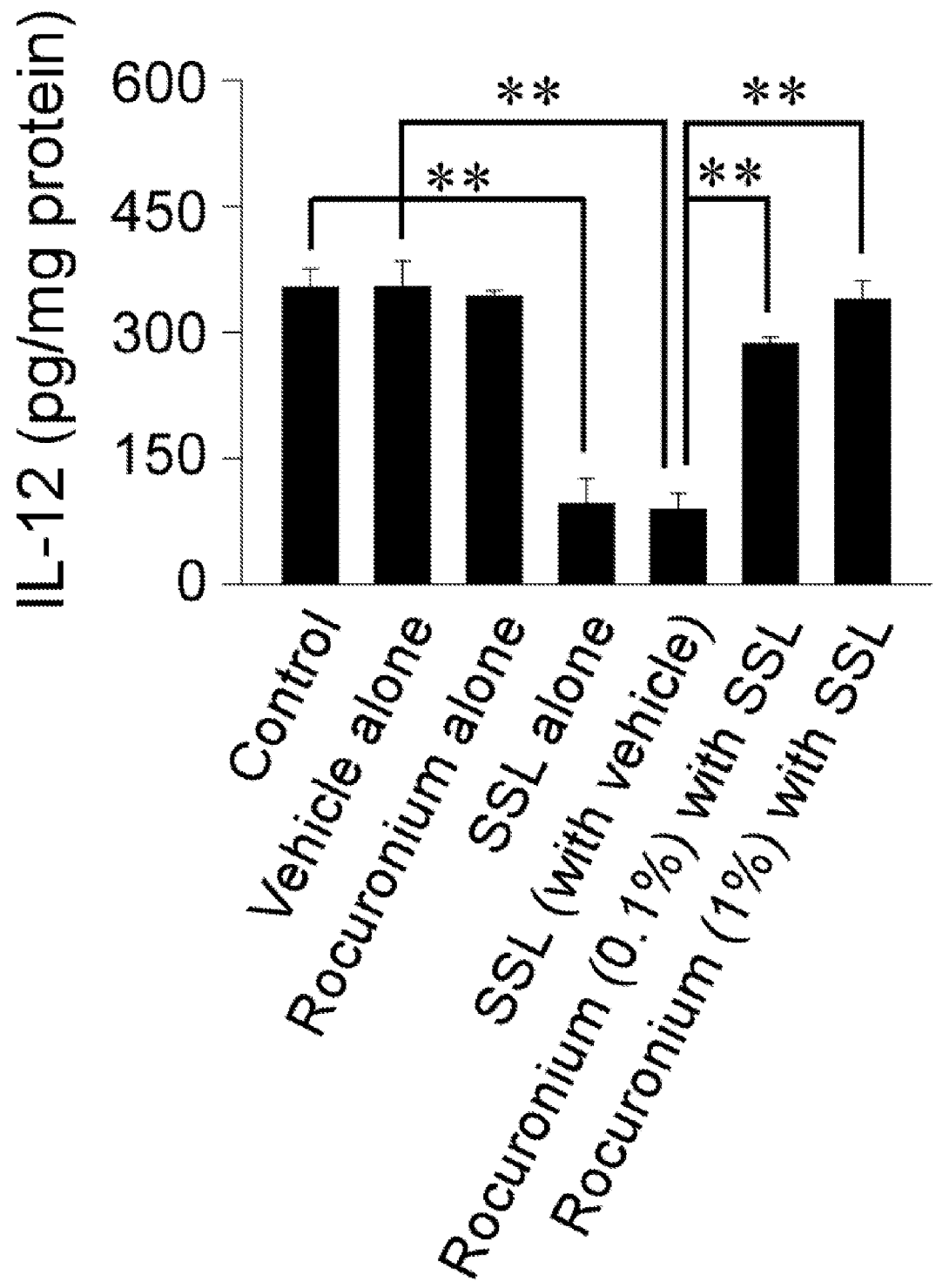
FIG. 25C is a chart comparing the effect of rocuronium bromide treatment on enhancement of IL-12 production in the skin tissues in an early-stage SSL-induced prevention model.
Figure 25D:
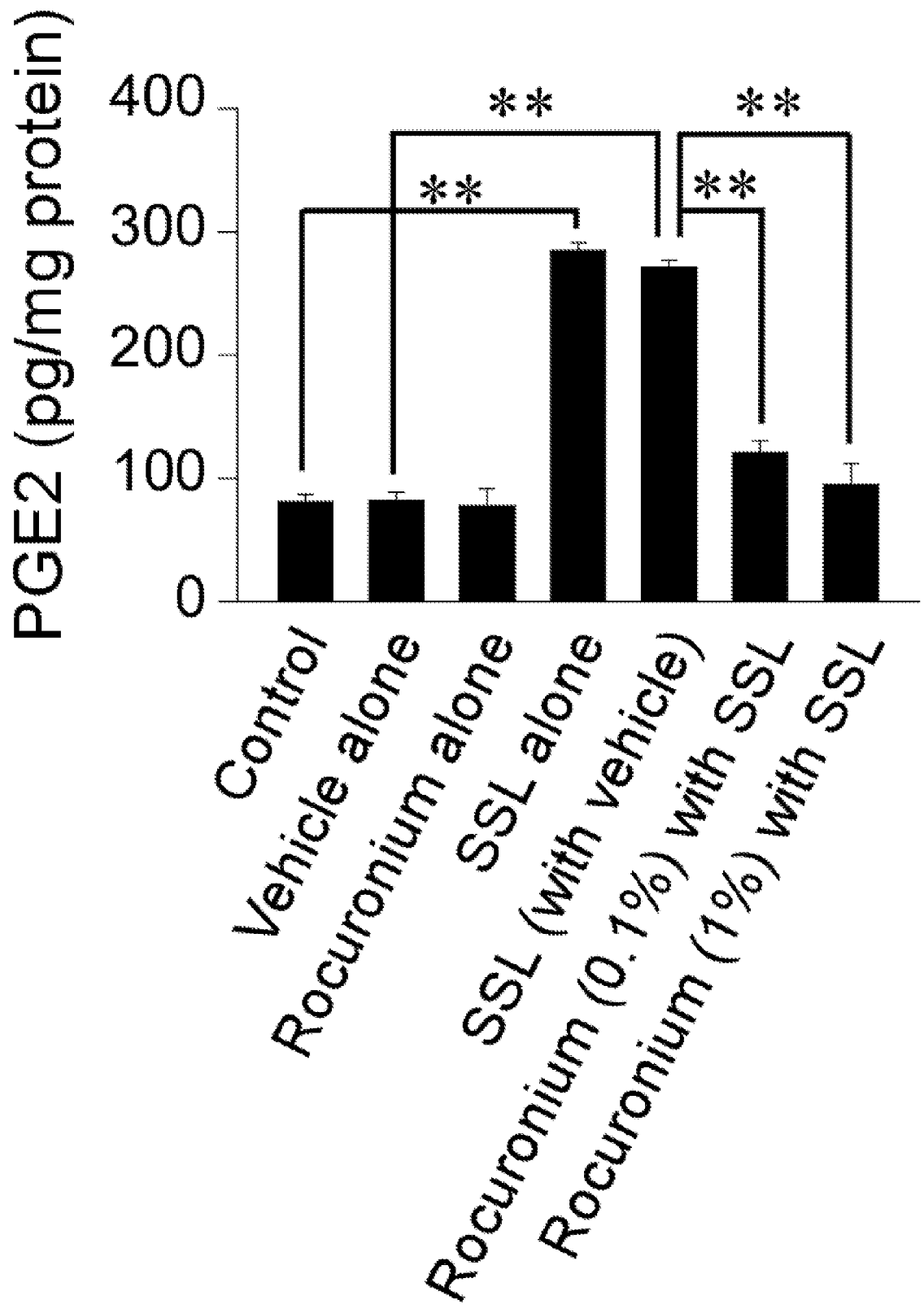
FIG. 25D is a chart comparing the effect of rocuronium bromide treatment on enhancement of PGE2 production in the skin tissues in an early-stage SSL-induced prevention model.

FIG. 25B is a chart comparing the effect of rocuronium bromide treatment on enhancement of IL-12 production in mouse serum in an early-stage SSL-induced prevention model. FIG. 25C is a chart comparing the effect of rocuronium bromide treatment on enhancement of IL-12 production in the skin tissues in an early-stage SSL-induced prevention model. FIG. 25D is a chart comparing the effect of rocuronium bromide treatment on enhancement of PGE2 production in the skin tissues in an early-stage SSL-induced prevention model.

Figure 26A:
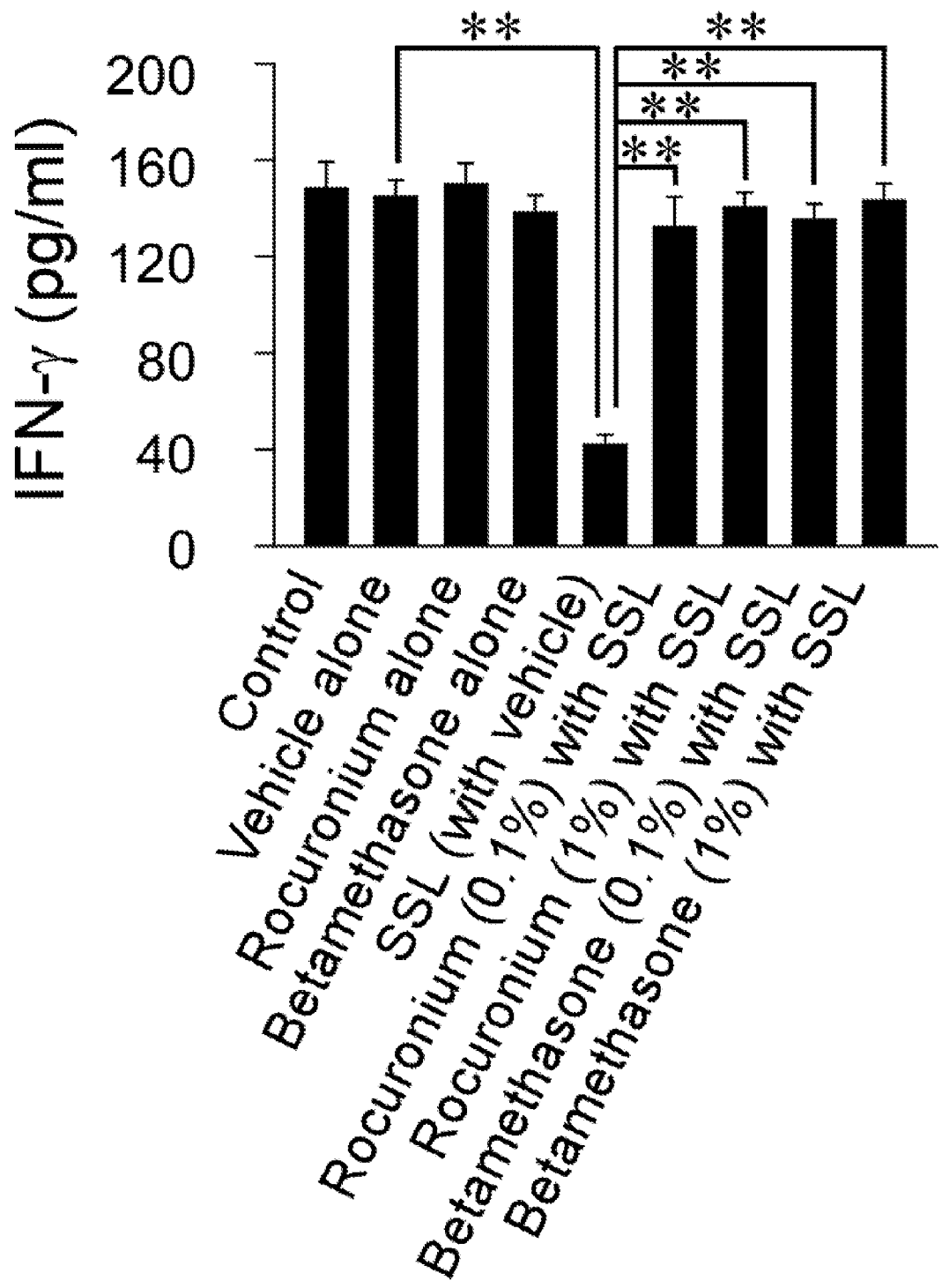
FIG. 26A is a chart comparing the effect of rocuronium bromide treatment and betamethasone 17-valerate treatment on enhancement of IFN-γ production by immune cells in a late-stage SSL-induced prevention model.
Figure 26B:
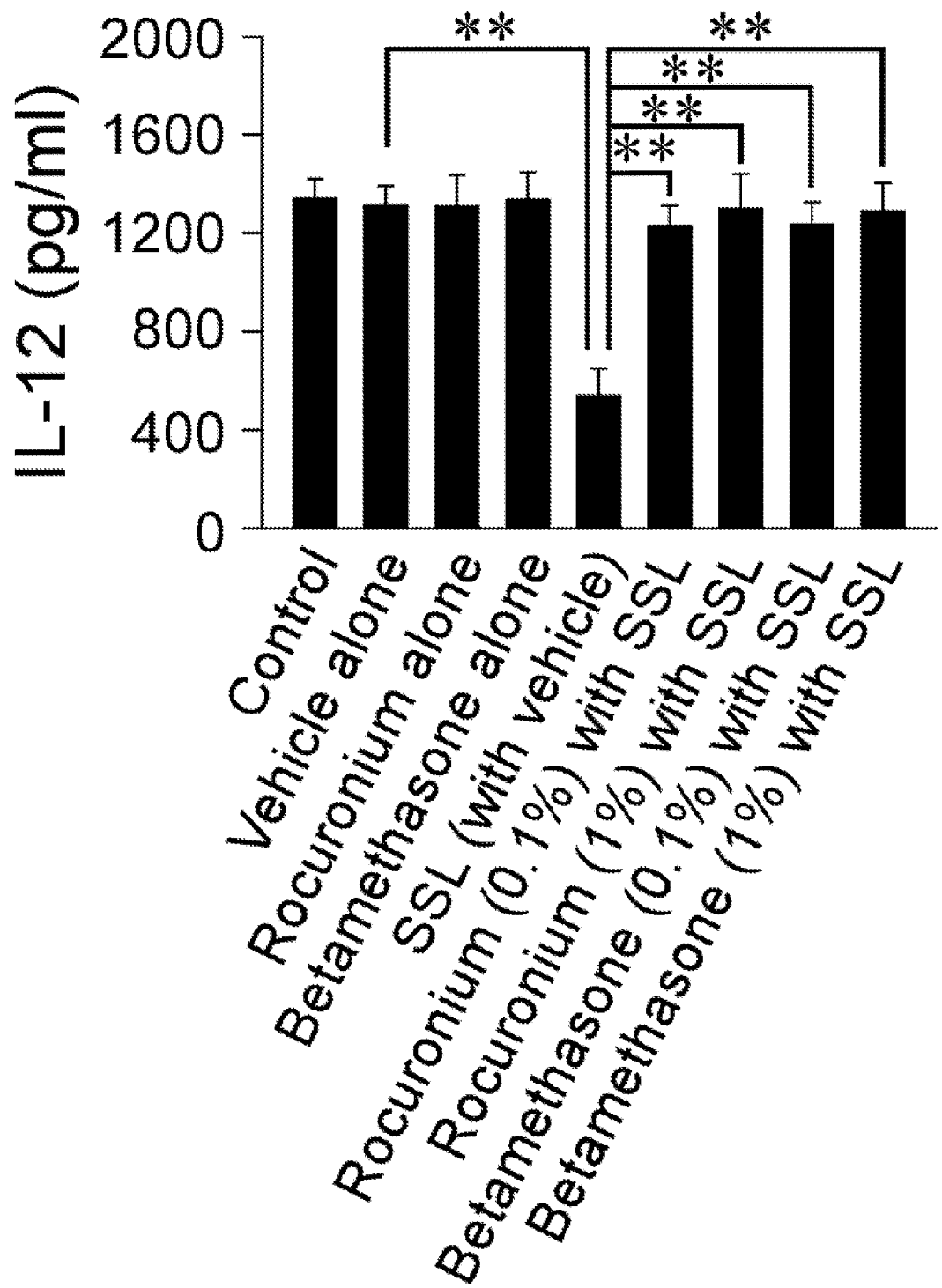
FIG. 26B is a chart comparing the effect of rocuronium bromide treatment and betamethasone 17-valerate treatment on enhancement of IL-12 production in the mouse serum in a late-stage SSL-induced prevention model.
Figure 26C:
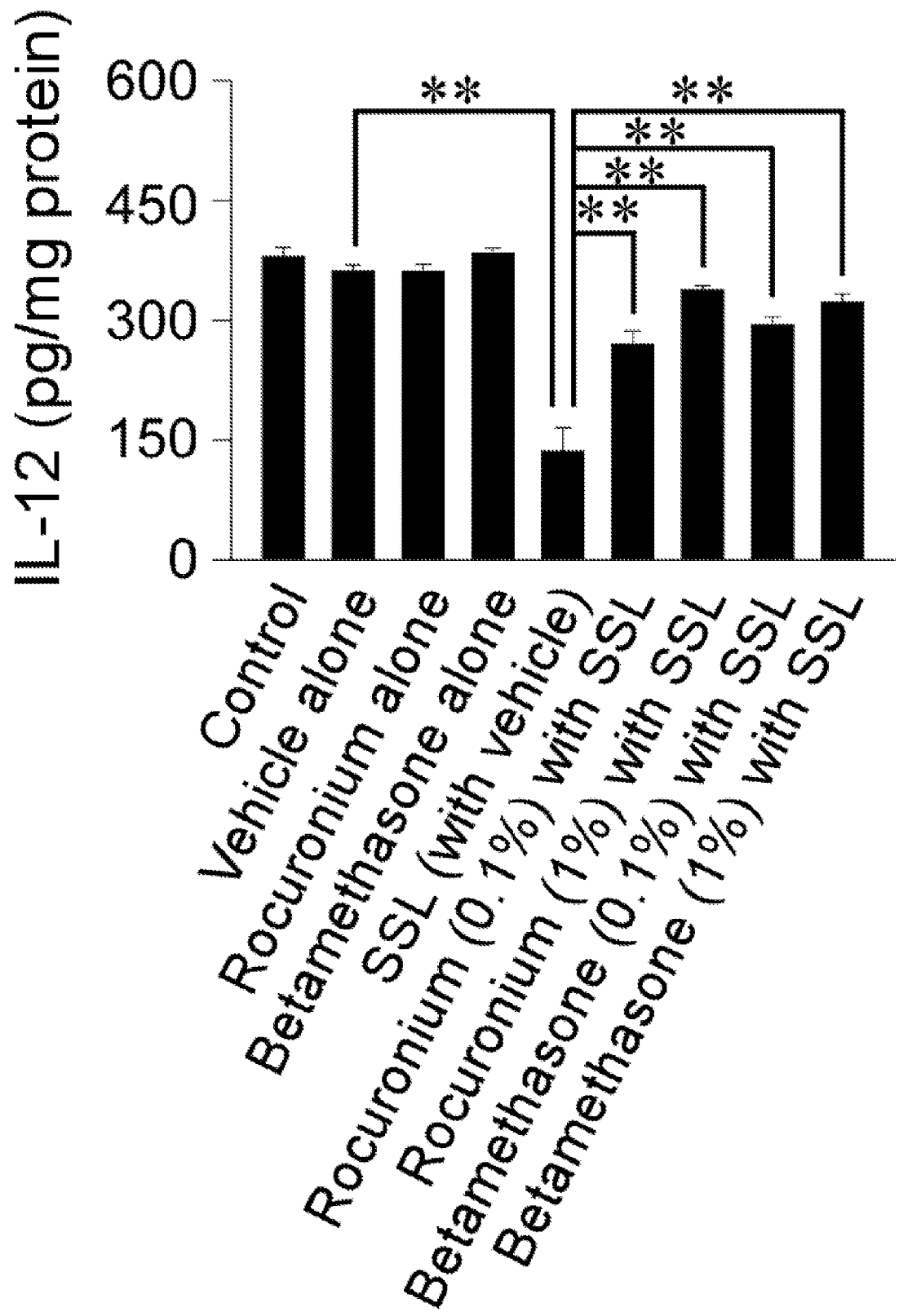
FIG. 26C is a chart comparing the effect of rocuronium bromide treatment and betamethasone 17-valerate treatment on enhancement of IL-12 production in the skin tissues in a late-stage SSL-induced prevention model.
Figure 26D:
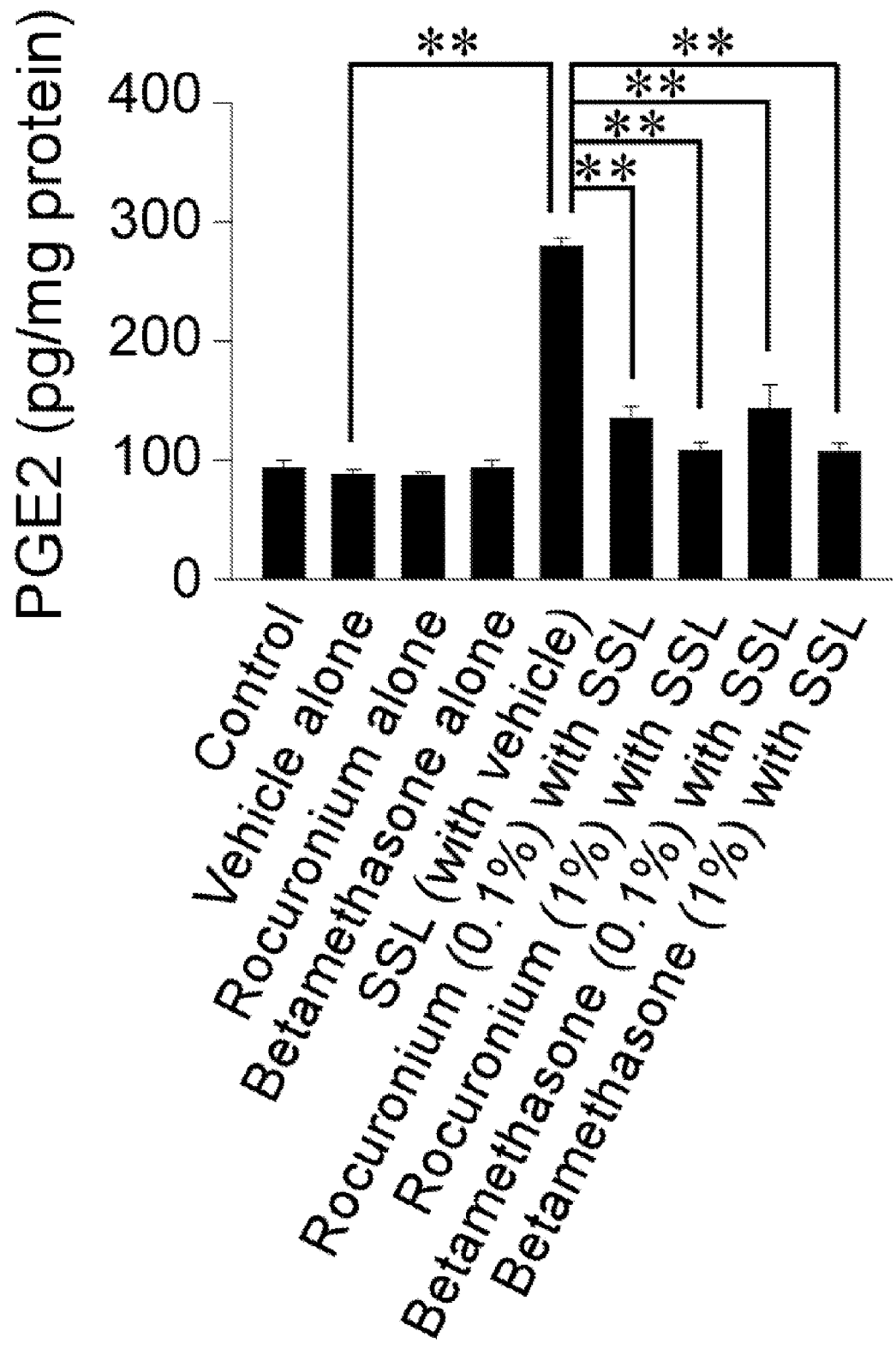
FIG. 26D is a chart comparing the effect of rocuronium bromide treatment and betamethasone 17-valerate treatment on enhancement of PGE2 production in the skin tissues in a late-stage SSL-induced prevention model.

FIG. 26A is a chart comparing the effect of rocuronium bromide treatment and betamethasone 17-valerate treatment on enhancement of IFN-γ production by immune cells in an late-stage SSL-induced prevention model. FIG. 26B is a chart comparing the effect of rocuronium bromide treatment and betamethasone 17-valerate treatment on enhancement of IL-12 production in the mouse serum in a late-stage SSL-induced prevention model. FIG. 26C is a chart comparing the effect of rocuronium bromide treatment and betamethasone 17-valerate treatment on enhancement of IL-12 production in the skin tissues in a late-stage SSL-induced prevention model. FIG. 26D is a chart comparing the effect of rocuronium bromide treatment and betamethasone 17-valerate treatment on enhancement of PGE2 production in the skin tissues in a late-stage SSL-induced prevention model. PRPK inhibitors, rocuronium bromide treatment and betamethasone 17-valerate, increased the production of IFN-γ in mouse serum and IL-12 in mouse serum/and mouse skin, and decreased PGE2 levels in the skin. Rocuronium bromide treatment and betamethasone 17-valerate attenuated the levels of PGE2 production in SSL-exposed skin, which may play a role in the up-regulation of IL-12 production. Thus, the stimulation of IFN-γ and IL-12 by PRPK inhibitors, rocuronium bromide treatment and betamethasone 17-valerate, could have a role in prevention of sUV-induced immunosuppression by up-regulating IFN-γ and IL-12 and down-regulating PGE2.

Example 13—Rocuronium Bromide or Betamethasone 17-Valerate do not Substantially Absorb or Block sUV Wavelengths To assess whether the effectiveness of rocuronium bromide or betamethasone 17-valerate was related to absorption or attenuation of sUV wavelengths, instead of or in addition to inhibition of PRPK phosphorylation, absorption of sUV wavelengths by rocuronium bromide or betamethasone 17-valerate was evaluated. Neither of rocuronium bromide or betamethasone 17-valerate was found to substantially absorb in either the UVB or UVA range (280 to 400 nm). The maximum absorption wavelength for rocuronium bromide was 227 nm, and that for betamethasone-17-valerate was 240 nm.

Example 14—p53 Mutations are not Detected in TOPK Knockout Mice or Mice Treated with PRPK Inhibitors cSCC lesions are often characterized by UV-induced mutations in the p53 gene. In human skin cancers, p53 mutations are mainly C-T substitutions located on dipyrimidine sites that are specific UV targets. To determine whether TOPK knockout or PRPK inhibitors could affect SSL-induced p53 mutations, we performed a sequencing analysis of the p53 gene. Mutations of the p53 gene were detected in SCCs from human, SSL-exposed TOPK$^{+/+}$ mice and SSL-induced SCCs from SKH-1 hairless mice (TABLES 1, 2, 3A and 3B). One hundred percent of the mutations in codon 267 were C to T substitutions. We also observed a high frequency of mutations in codons 270, 277 and 284 of the p53 gene in both human and mouse cSCC. Importantly, mutations of the p53 gene were not detected in SSL-treated skin from TOPK$^{-/-}$ mice or from mice treated with PRPK inhibitors. Notably, these mice did not develop SCCs. TABLE 1 shows a summary of all the p53 mutations that were detected in human samples of SCC. TABLE 2 shows a summary of all the p53 mutations that were detected in solar UV-exposed TOPK wildtype (+/+) mice. Finally, TABLE 3A (in exon 7) and 3B (in exon 8) shows a summary of all the p53 mutations detected in sUV-induced SCC from SKH-1 hairless mouse skin.

TABLE 1

| | | Wild type | cSCC in human | | | | % of c→t |
|---|---|---|---|---|---|---|---|
| Exon | Codon | p53 | case 1 | case 2 | case 3 | case 4 | substitution |
| 7 | 225 | acc (T) → | aat (N) | aaa (K) | acg (T) | ata (I) | 50 |
| 7 | 226 | atc (I) → | | aca (T) | aca (T) | aga (R) | 0 |
| 7 | 227 | cac (H) → | | | tac (Y) | aag (K) | 50 |
| 7 | 228 | tac (Y) → | | tgt (C) | cac (H) | tat (Y) | 67 |
| 7 | 230 | tac (Y) → | cac (H) | aac (N) | | gac (D) | 0 |
| 7 | 234 | agc (S) → | | agg (R) | acc (T) | acc (T) | 0 |
| 7 | 235 | tcc (S) → | ttg (L) | ttt (F) | ttc (F) | ttc (F) | 100 |
| 7 | 236 | tgc (C) → | tgg (W) | | | tgt (C) | 50 |
| 7 | 239 | ggc (G) → | ggg (G) | | | ggg (G) | 0 |
| 7 | 241 | aac (N) → | aag (K) | aaa (K) | | | 0 |
| 7 | 242 | cgc (R) → | cga (R) | cgt (R) | | | 50 |
| 7 | 243 | cga (R) → | cgg (R) | tct (S) | cat (H) | ctg (L) | 50 |
| 7 | 244 | cct (P) → | caa (Q) | gcc (A) | ctt (L) | | 33 |
| 7 | 245 | atc (I) → | ata (I) | atg (M) | | att (I) | 33 |
| 7 | 246 | ctt (L) → | ttt (F) | ttt (F) | | cct (P) | 67 |
| 7 | 247 | acc (T) → | atc (I) | aca (T) | | tcc (S) | 33 |
| 7 | 248 | atc (I) → | gtc (V) | ttc (F) | | tct (S) | 33 |
| 7 | 249 | atc (I) → | agt (S) | gcg (A) | | ata (I) | 33 |
| 7 | 250 | aca (T) → | gca (A) | ata (I) | | gct (A) | 33 |
| 7 | 251 | ctg (L) → | cgg (R) | ctt (L) | cta (L) | | 0 |
| 7 | 253 | gac (D) → | gag (E) | gat (D) | tac (S) | | 33 |
| 7 | 254 | tcc (S) → | ttt (F) | | | acc (T) | 50 |
| 8 | 264 | ttt (F) → | | tct (S) | tct (S) | tct (S) | 0 |
| 8 | 265 | gag (E) → | | ttg (L) | | | 0 |
| 8 | 267 | cgt (R) → | tgg (W) | tgt (C) | tgt (C) | tgt (C) | 100 |
| 8 | 270 | gcc (A) → | gtt (V) | gtc (V) | gtc (V) | | 100 |
| 8 | 272 | cct (P) → | cct (L) | gca (A) | tct (S) | ctt (L) | 50 |
| 8 | 276 | cgc (R) → | | ccc (P) | | | 0 |
| 8 | 277 | cgt (R) → | ttt (F) | ctt (L) | | | 50 |
| 8 | 279 | gaa (E) → | cca (P) | | | | 0 |
| 8 | 280 | gaa (E) → | | | | | 0 |
| 8 | 284 | cgc (R) → | | | cgt (R) | cgt (R) | 100 |
| 8 | 285 | aaa (K) → | | | | | 0 |
| 8 | 288 | gtc (V) → | | atc (I) | | | 0 |
| 8 | 289 | ctt (L) → | | | | ttt (F) | 100 |
| 8 | 292 | gaa (E) → | gag (E) | gta (V) | | | 0 |
| 8 | 294 | ccc (P) → | cgc (R) | tcc (S) | | | 50 |
| 8 | 295 | cca (P) → | | ctt (L) | | | 100 |

TABLE 2

| Exon | Codon | Wild type p53 | TOPK+/+ mice (sUV-exposed) mouse 1 | mouse 2 | mouse 3 | % of c→t substitution |
|---|---|---|---|---|---|---|
| 7 | 225 | acc (T) → | aaa (K) | act (T) | atc (I) | 67 |
| 7 | 226 | atc (I) → | ata (I) | aga (R) | agg (R) | 0 |
| 7 | 227 | cac (H) → | cat (H) | cag (Q) | caa (Q) | 33 |
| 7 | 228 | tac (Y) → | tat (Y) | tat (Y) | gac (D) | 67 |
| 7 | 230 | tac (Y) → | aac (N) | | gac (D) | 0 |
| 7 | 234 | agc (S) → | aga (R) | agt (S) | agg (R) | 33 |
| 7 | 235 | tcc (S) → | tca (S) | ttc (F) | ttg (L) | 67 |
| 7 | 236 | tgc (C) → | | | tgg (W) | 0 |
| 7 | 239 | ggc (G) → | ggt (G) | gac (D) | ggt (G) | 67 |
| 7 | 241 | aac (N) → | | aag (K) | aaa (K) | 0 |
| 7 | 242 | cgc (R) → | cgt (R) | cgt (R) | cgg (R) | 67 |
| 7 | 243 | cga (R) → | caa (Q) | cgg (R) | cgg (R) | 0 |
| 7 | 244 | cct (P) → | ctt (L) | | gtt (L) | 100 |
| 7 | 245 | atc (I) → | | gtc (V) | ctc (L) | 0 |
| 7 | 246 | ctt (L) → | | | ttt (F) | 100 |
| 7 | 247 | acc (T) → | atc (I) | | atc (I) | 100 |
| 7 | 248 | atc (I) → | att (I) | att (I) | ttc (F) | 67 |
| 7 | 249 | atc (I) → | ctc (L) | ctc (L) | gaa (E) | 0 |
| 7 | 250 | aca (T) → | | gca (A) | ata (I) | 50 |
| 7 | 251 | ctg (L) → | gtg (V) | ttg (L) | ttg (L) | 67 |
| 7 | 253 | gac (D) → | | cac (H) | cac (H) | 0 |
| 7 | 254 | tcc (S) → | acc (T) | ttt (F) | ccc (P) | 33 |
| 8 | 264 | ttt (F) → | | | | 0 |
| 8 | 265 | gag (E) → | | | tat (Y) | 0 |
| 8 | 267 | cgt (R) → | | tgt (C) | | 100 |
| 8 | 270 | gcc (A) → | gtc (V) | | ggt (G) | 100 |
| 8 | 272 | cct (P) → | | gct (A) | | 0 |
| 8 | 276 | cgc (R) → | | | | 0 |
| 8 | 277 | cgt (R) → | tgt (C) | | | 100 |
| 8 | 279 | gaa (E) → | | | | 0 |
| 8 | 280 | gaa (E) → | | | aaa (K) | 0 |
| 8 | 284 | cgc (R) → | cgt (R) | cgt (R) | cgt (R) | 100 |
| 8 | 285 | aaa (K) → | | | tca (S) | 0 |
| 8 | 288 | gtc (V) → | | | ctc (L) | 0 |
| 8 | 289 | ctt (L) → | | | | 0 |
| 8 | 292 | gaa (E) → | gtt (V) | | gta (V) | 0 |
| 8 | 294 | ccc (P) → | | | | 0 |
| 8 | 295 | cca (P) → | | | | 0 |

TABLE 3A

SSL-induced cSCC development in mouse

| Exon | Codon | Wild type p53 | In early-stage prevention model (Groups 4 and 5) | | | | | | | In late-stage prevention model (Group 12) | | | | % of c→t substitution |
|---|---|---|---|---|---|---|---|---|---|---|---|---|---|---|
| 7 | 225 | acc (T) → | acg (T) | aca (T) | att (I) | atc (I) | aca (T) | aat (N) | aag (K) | acg (T) | agg (R) | aac (N) | acg (T) | atg (M) | 33 |
| 7 | 226 | atc (I) → | acc (T) | att (I) | act (T) | caa (Q) | acc (T) | act (T) | | | acg (T) | agc (S) | aca (T) | ata (I) | 30 |
| 7 | 227 | cac (H) → | aag (K) | | cat (H) | cat (H) | cag (Q) | cat (H) | | cat (H) | cat (H) | cat (H) | ctt (L) | aca (T) | 73 |
| 7 | 228 | tac (Y) → | tat (Y) | gtc (V) | gac (D) | tat (Y) | gac (D) | tat (Y) | tat (Y) | tct (S) | cac (H) | tat (Y) | tat (Y) | cac (H) | tat (Y) | 62 |
| 7 | 230 | tac (Y) → | cac (H) | | gac (D) | aac (N) | | aac (N) | aac (N) | aac (N) | cac (H) | cac (H) | gac (D) | | gac (D) | 0 |
| 7 | 234 | agc (S) → | agg (R) | agt (S) | agt (S) | agt (S) | | agt (S) | agt (S) | agg (R) | agt (S) | | aga (R) | agg (R) | 60 |
| 7 | 235 | tcc (S) → | ttt (F) | tat (Y) | ttt (F) | | ttt (F) | tta (L) | ttc (F) | ttt (F) | tgt (C) | tta (L) | ttt (F) | tca (S) | 92 |
| 7 | 236 | tgc (C) → | tgt (C) | agg (R) | | tgg (W) | | tct (S) | tcc (S) | tgg (W) | | | tgt (C) | tgg (W) | 38 |
| 7 | 239 | ggc (G) → | gga (G) | gga (G) | ggt (G) | gga (G) | ggt (G) | ggt (G) | | ggg (G) | | | gac (D) | ggg (G) | gga (G) | 30 |
| 7 | 241 | aac (N) → | aag (K) | aag (K) | aag (K) | aat (N) | aat (N) | aat (N) | aaa (K) | | aaa (K) | | aag (K) | aat (N) | aat (N) | 45 |
| 7 | 242 | cgc (R) → | cga (R) | cga (R) | cgg (R) | | ttt (F) | | | cac (H) | cga (R) | cgt (R) | ggc (G) | ttt (F) | cgt (R) | 40 |
| 7 | 243 | cga (R) → | | cgg (R) | cgt (R) | caa (Q) | cgg (R) | cgt (R) | cgg (R) | cgt (R) | cgg (R) | | cgg (R) | cgg (R) | caa (Q) | 0 |
| 7 | 244 | cct (P) → | | cca (P) | ccc (P) | ctt (L) | ccc (P) | ctg (L) | cac (H) | act (T) | gct (A) | cca (P) | cgt (R) | act (T) | 18 |
| 7 | 245 | atc (I) → | att (I) | acc (T) | | aac (N) | | atg (M) | | att (I) | atg (M) | atg (M) | | atg (M) | | 29 |
| 7 | 246 | ctt (L) → | cat (H) | ccg (P) | att (I) | | ttt (F) | ttc (F) | ttt (F) | cct (P) | att (I) | ttt (F) | ttt (F) | ttg (L) | 55 |
| 7 | 247 | acc (T) → | aca (T) | atc (I) | atc (I) | | atc (I) | atc (I) | atc (I) | | atc (I) | atc (I) | atc (I) | 90 |
| 7 | 248 | atc (I) → | | ttc (F) | ctc (L) | att (I) | ttc (F) | ttc (F) | | ttc (F) | ttc (F) | att (I) | aac (N) | ttc (F) | 20 |
| 7 | 249 | atc (I) → | acc (T) | cgc (R) | | | cta (L) | acc (T) | tcc (S) | att (I) | aag (K) | ggc (G) | tct (S) | | 22 |
| 7 | 250 | aca (T) → | | tca (S) | ata (I) | gca (A) | act (T) | tca (S) | gca (A) | tca (S) | ata (I) | gca (A) | gca (A) | ata (I) | 27 |
| 7 | 251 | ctg (L) → | ttg (L) | ctc (L) | ttg (L) | ctt (L) | ctt (L) | ctc (L) | | ttg (L) | cta (L) | gtg (V) | gtg (V) | ttg (L) | 36 |
| 7 | 253 | gac (D) → | | gat (D) | gat (D) | aac (N) | cac (H) | gat (D) | | aac (N) | gat (D) | gat (D) | gat (D) | tac (S) | 64 |
| 7 | 254 | tcc (S) → | aac (N) | ttt (F) | tct (S) | | ttt (F) | tct (S) | | | tct (S) | ttt (F) | ttt (F) | tct (S) | 90 |

TABLE 3B

SSL-induced cSCC development in mouse

| Exon | Codon | Wild type p53 | In early-stage prevention model (Groups 4 and 5) | In late-stage prevention model (Group 12) | % of c→t substitution |
|---|---|---|---|---|---|
| 8 | 264 | ttt (F) → | tct (S) | tct (S) | cct (P) | tct (S) | 0 |
| 8 | 265 | gag (E) → | tcg (S) tcg (S) | | ttg (L) | tgg (W) | 0 |
| 8 | 267 | cgt (R) → | tgc (C) tgt (C) tgt (C) | tgt (C) tct (S) | | tgt (C) | 100 |
| 8 | 270 | gcc (A) → | gtc (V) gtt (V) gtc (V) gtc (V) | gtc (V) | gtc (V) | ggc (G) | 86 |
| 8 | 272 | cct (P) → | gtt (V) tct (S) | tct (S) | tct (S) | ctt (L) | 100 |
| 8 | 276 | cgc (R) → | ccc (P) | ccc (P) | ccc (P) | | 0 |
| 8 | 277 | cgt (R) → | tgt (C) | | ctt (L) | tgt (C) tgt (C) | 75 |
| 8 | 279 | gaa (E) → | caa (Q) caa (Q) | | caa (Q) | | 0 |
| 8 | 280 | gaa (E) → | | | tta (L) | | 0 |
| 8 | 284 | cgc (R) → | cat (H) cgc (R) ctc (L) | cgt (R) ctg (L) | cga (R) | | 33 |
| 8 | 285 | aaa (K) → | gaa (E) | | tta (L) | | 0 |
| 8 | 288 | gtc (V) → | | | ggc (G) | | 0 |
| 8 | 289 | ctt (L) → | ttt (F) | ttt (F) | ttt (F) tgt (C) | tgt (C) | 100 |
| 8 | 292 | gaa (E) → | gta (V) gga (G) | gta (V) | gca (A) | | 0 |
| 8 | 294 | ccc (P) → | tcc (S) | tcc (S) | ttc (F) | tcc (S) | 100 |
| 8 | 295 | cca (P) → | ccg (P) | caa (Q) | cga (R) | | 0 |

Example 15

To assess pharmacokinetics, RB cream (1.0 mg RB in 100 μl cream) was topically applied to the dorsum of SKH1-Hrhr hairless mice (Charles River), and plasma sample were taken at 0, 0.25, 0.5, 1, 2, 6, 24 and 48 hours post-dose (3 mice/time point).

Figure 27:
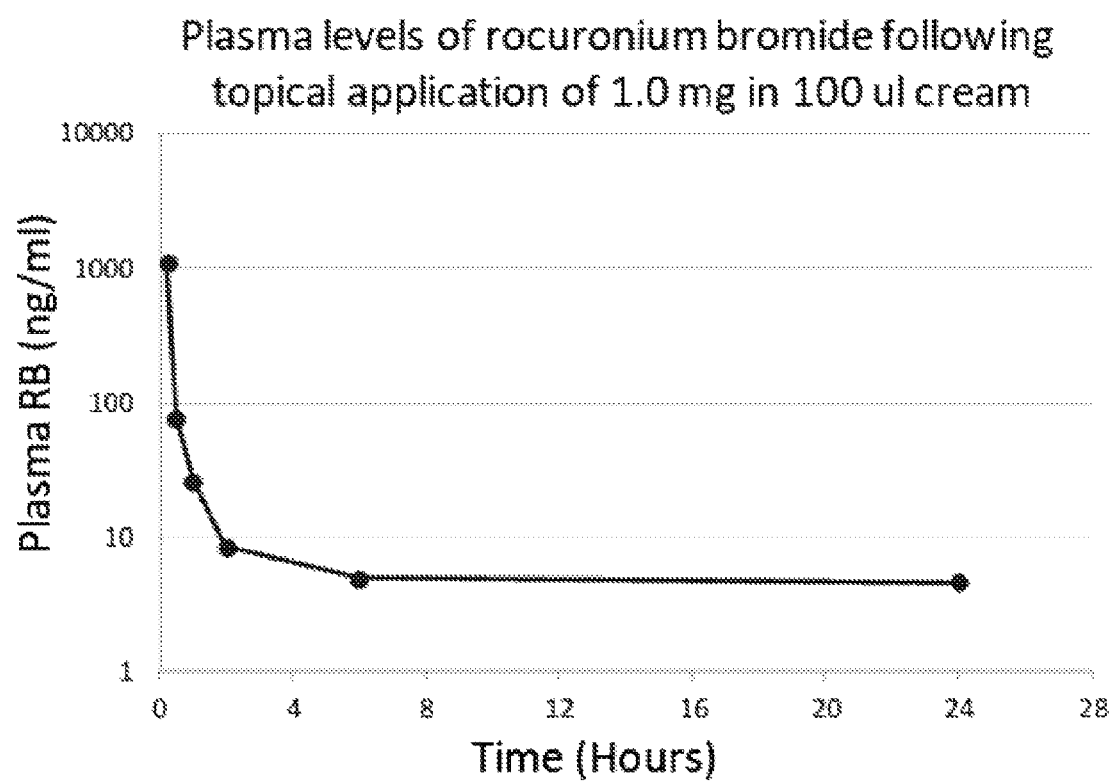
FIG. 27 is a chart showing plasma levels of rocuronium bromide following topical application.

FIG. 27 is a chart showing plasma levels of rocuronium bromide following topical application. The RB exhibited a rapid systemic absorption with peak plasma levels occurring at ≤15 minutes post application, as seen in FIG. 27 and TABLE 4.

TABLE 4

| Mouse # | TIME (h) | ng/ml RB | MEAN | SE |
|---|---|---|---|---|
| 91 | 0.25 | 3058 | | |
| 95 | 0.25 | 18 | | |
| 96 | 0.25 | 210 | 1095.3 | 984.1 |
| 97 | 0.5 | 36 | | |
| 99 | 0.5 | 73 | | |
| 109 | 0.5 | 123 | 77.3 | 25.2 |
| 111 | 1 | 7 | | |
| 114 | 1 | 25 | | |
| 117 | 1 | 48 | 26.7 | 11.9 |
| 105 | 2 | 11 | | |
| 110 | 2 | BDL | | |
| 123 | 2 | 15 | 8.7 | 1.6 |
| 119 | 6 | BDL | | |
| 120 | 6 | 7 | | |
| 124 | 6 | 8 | 5 | 0.4 |
| 102 | 24 | BDL | | |
| 106 | 24 | BDL | | |
| 113 | 24 | 14 | 4.7 | ND |
| 104 | 48 | BDL | | |
| 116 | 48 | BDL | | |
| 121 | 48 | BDL | ND | ND |

BDL = below detection limit (~2 ng/ml)
ND = Not determined

The variability in plasma levels was not outside expected bounds for topical application of a drug, where the rate and extent of systemic uptake is much less predictable than with oral or intravenous administration. Peak levels occurred at the earliest time point (15 minutes). There was a relatively rapid subsequent clearance of RB from the plasma, with RB in plasma approaching baseline levels for the assay by approximately 6 hours post-dose.

Example 16

Maximum tolerated dosage was evaluated. A formulation of RB cream at 20 mg RB in 200 μl cream applied to the dorsum of hairless mice caused death of the mice within 10-15 minutes post application. This observed time to death correlates well with the peak plasma levels of RB noted above following topical application. This formulation was also not stable and separated over time. A formulation of 10 mg RB in 200 μl cream was both stable and well tolerated following topical application.

Example 17

The effectiveness of different candidate compounds in preventing sUV-induced cancer was evaluated. SKH-1 hairless mice (Charles River, Burlington, Massachusetts) were treated with formulations including one or more candidate compounds and exposed to SSL (solar simulated light). Female mice aged 5-6 weeks at the beginning of the study were used. The mice were exposed to SSL three times a week for 15 weeks from the beginning of the study. At week 1, the SSL dose included 37 kJ/m² UVA and 1.8 kJ/m² UVB three times per week. The dose of SSL was gradually increased at a rate of 10% per week. At week 6, the dose included 60 kJ/m² UVA and 2.9 kJ/m² UVB and this dose was maintained until week 15 at which time SSL exposure was stopped. Each mouse received a topical application (on the dorsal skin surface posterior to the base of the neck and anterior to the base of the tail) of one or more candidate compounds in a base cream one hour before SSL exposure. 15 weeks onwards, the mice were no longer exposed to SSL but the topical application of cream with sunscreen compounds was continued until 30 weeks. Control mice received topical application of cream with sunscreen compounds but no SSL. Eight compounds were tested alone or in combination to confirm their effectiveness in preventing skin cancer. The compounds and concentrations used are presented in TABLE 5. The results are summarized in TABLE 6, and illustrated in FIGS. 28A to 41.

Figure 28A:
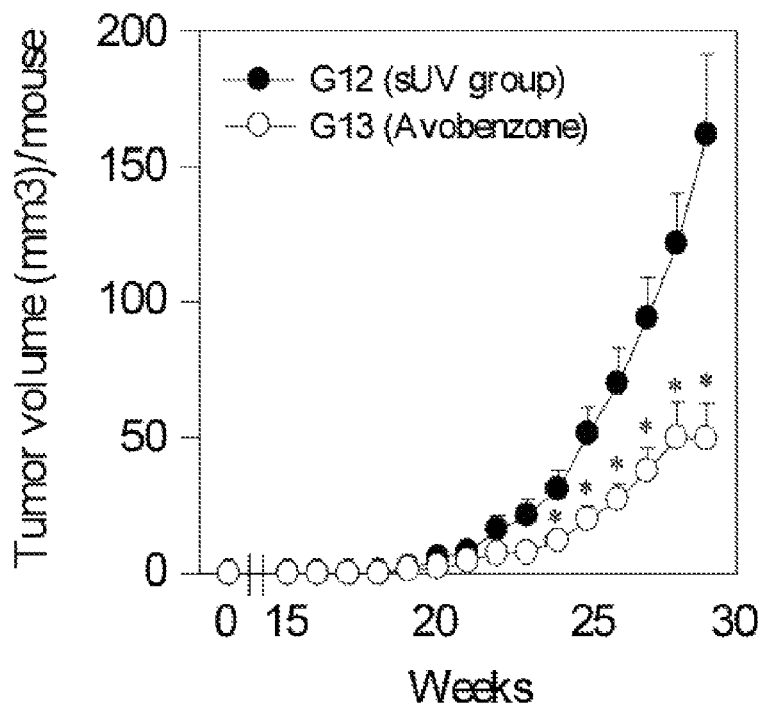
FIG. 28A is a chart illustrating average tumor volume in response to solar ultraviolet exposure in a group of mice treated with avobenzone compared to a group of untreated mice.
Figure 28B:
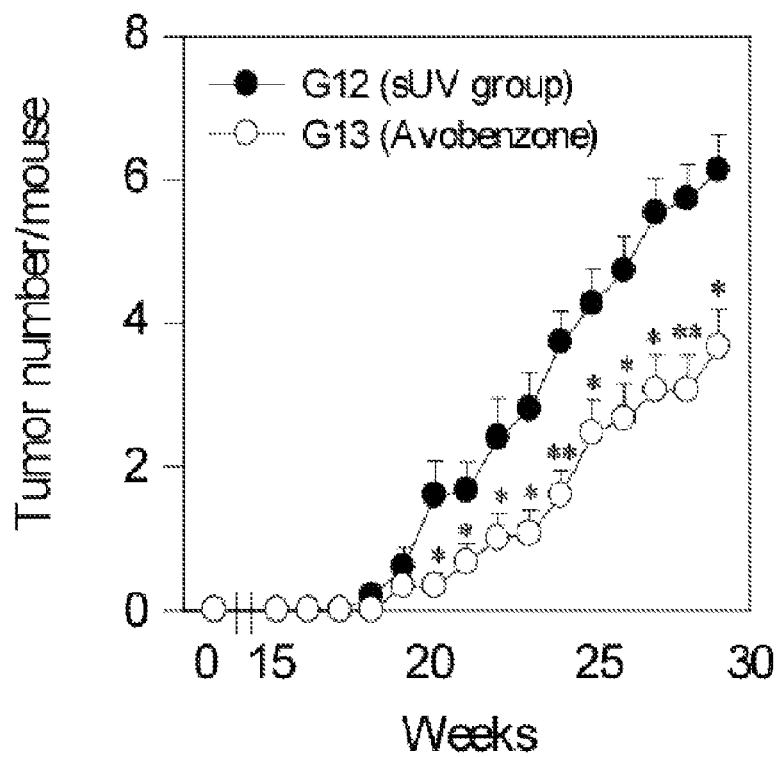
FIG. 28B is a chart illustrating average tumor number in response to solar ultraviolet exposure in a group of mice treated with avobenzone compared to a group of untreated mice.
Figure 29A:
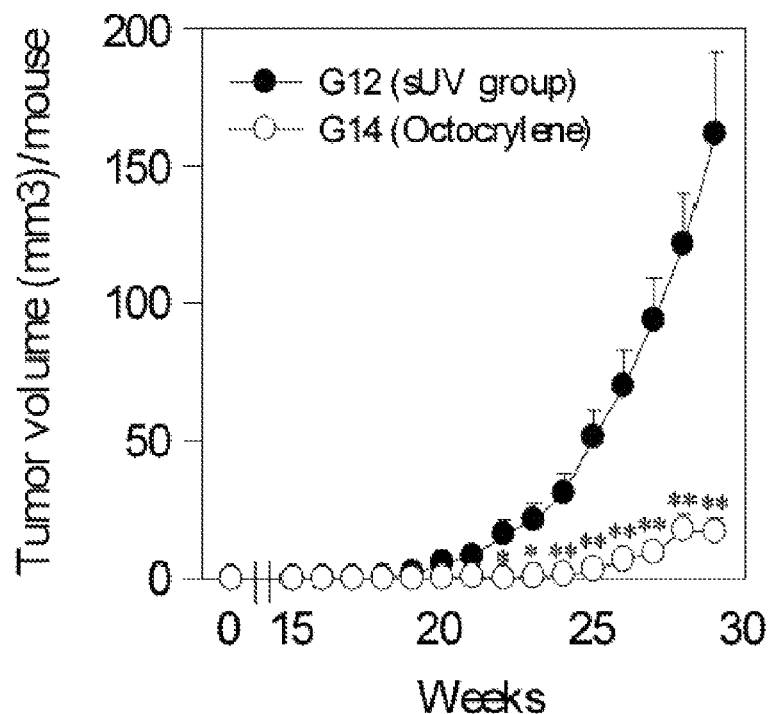
FIG. 29A is a chart illustrating average tumor volume in response to solar ultraviolet exposure in a group of mice treated with octocrylene compared to a group of untreated mice.
Figure 29B:
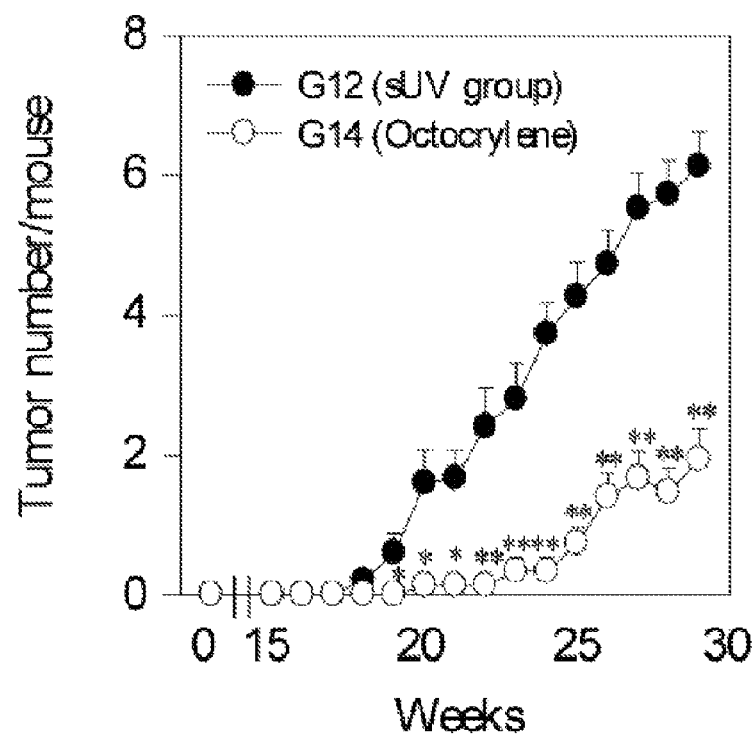
FIG. 29B is a chart illustrating average tumor number in response to solar ultraviolet exposure in a group of mice treated with octocrylene compared to a group of untreated mice.
Figure 30A:
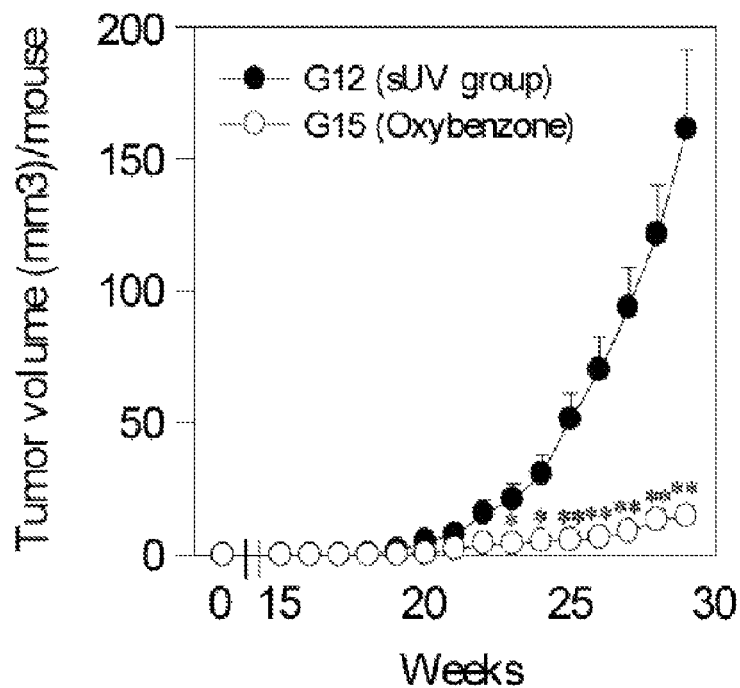
FIG. 30A is a chart illustrating average tumor volume in response to solar ultraviolet exposure in a group of mice treated with oxybenzone compared to a group of untreated mice.
Figure 30B:
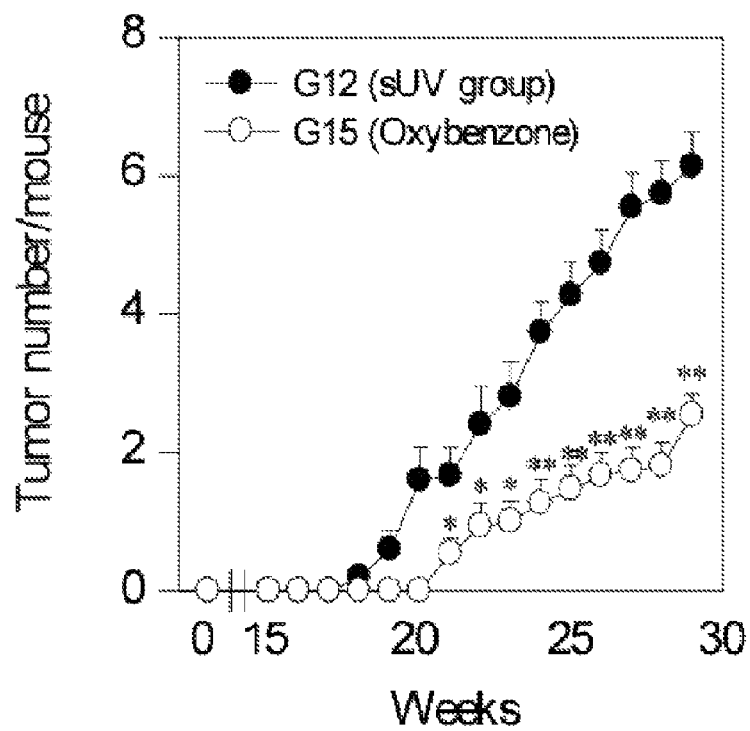
FIG. 30B is a chart illustrating average tumor number in response to solar ultraviolet exposure in a group of mice treated with oxybenzone compared to a group of untreated mice.
Figure 31A:
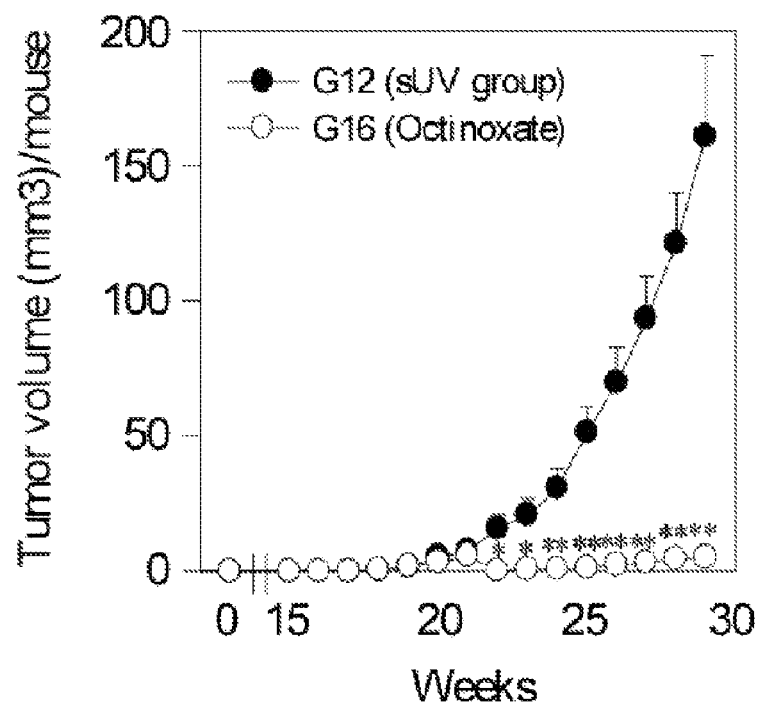
FIG. 31A is a chart illustrating average tumor volume in response to solar ultraviolet exposure in a group of mice treated with octinoxate compared to a group of untreated mice.
Figure 31B:
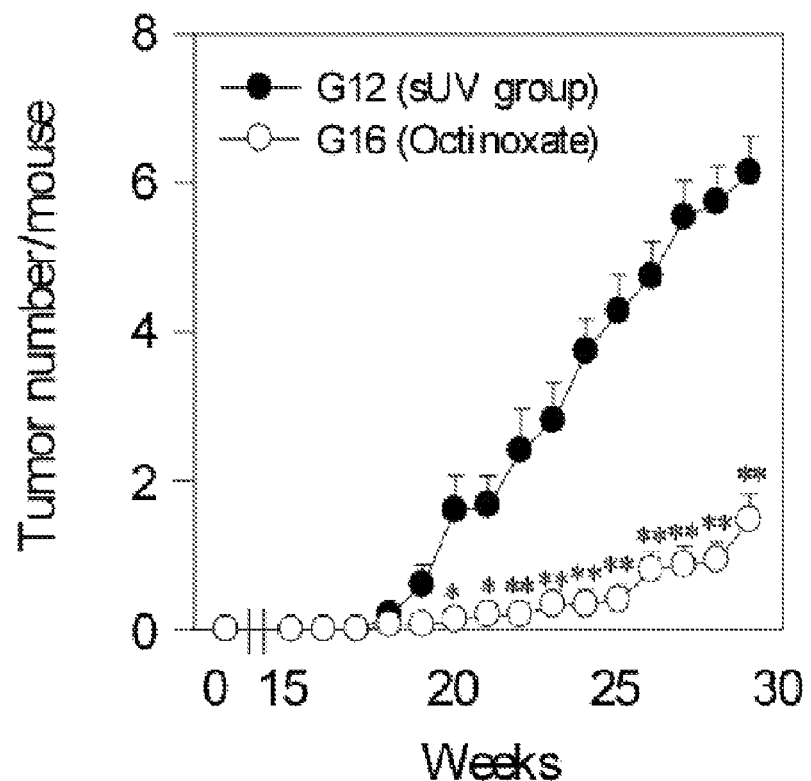
FIG. 31B is a chart illustrating average tumor number in response to solar ultraviolet exposure in a group of mice treated with octinoxate compared to a group of untreated mice.
Figure 32A:
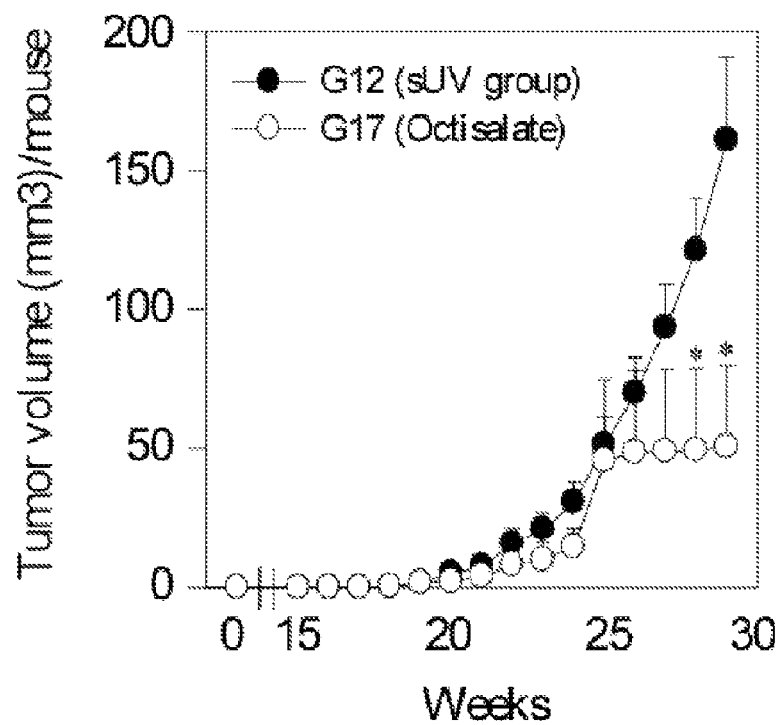
FIG. 32A is a chart illustrating average tumor volume in response to solar ultraviolet exposure in a group of mice treated with octisalate compared to a group of untreated mice.
Figure 32B:
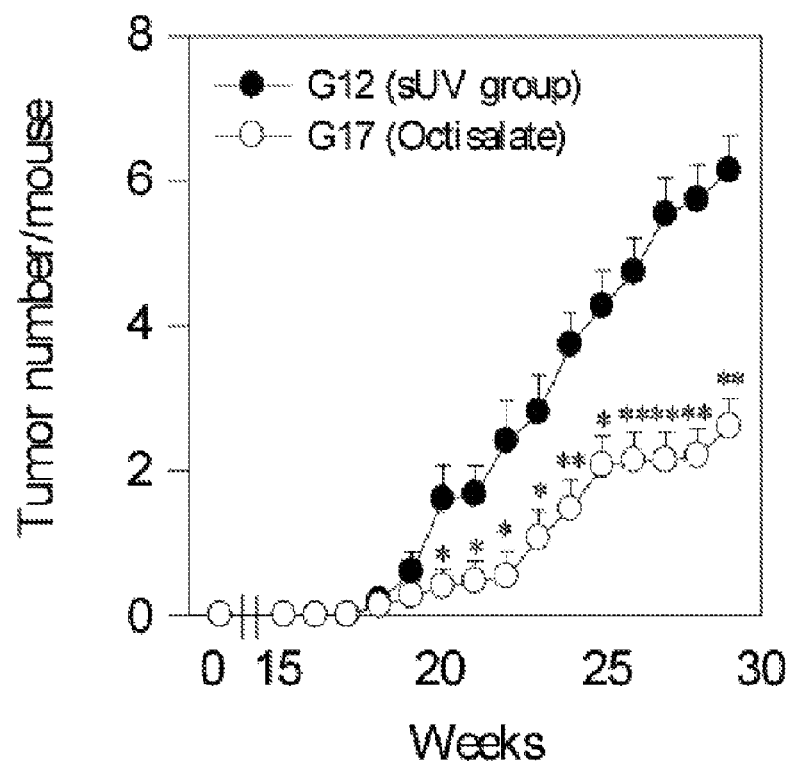
FIG. 32B is a chart illustrating average tumor number in response to solar ultraviolet exposure in a group of mice treated with octisalate compared to a group of untreated mice.
Figure 33A:
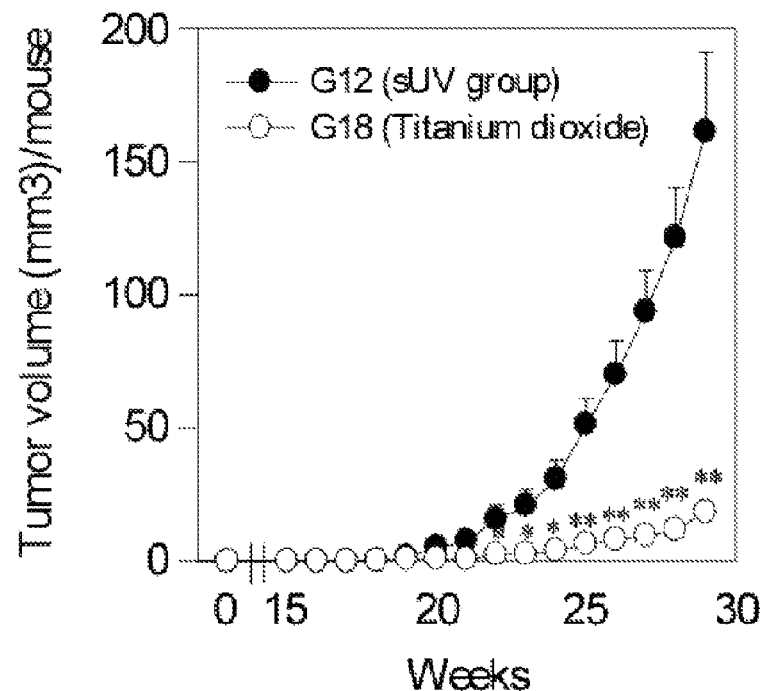
FIG. 33A is a chart illustrating average tumor volume in response to solar ultraviolet exposure in a group of mice treated with titanium dioxide compared to a group of untreated mice.
Figure 33B:
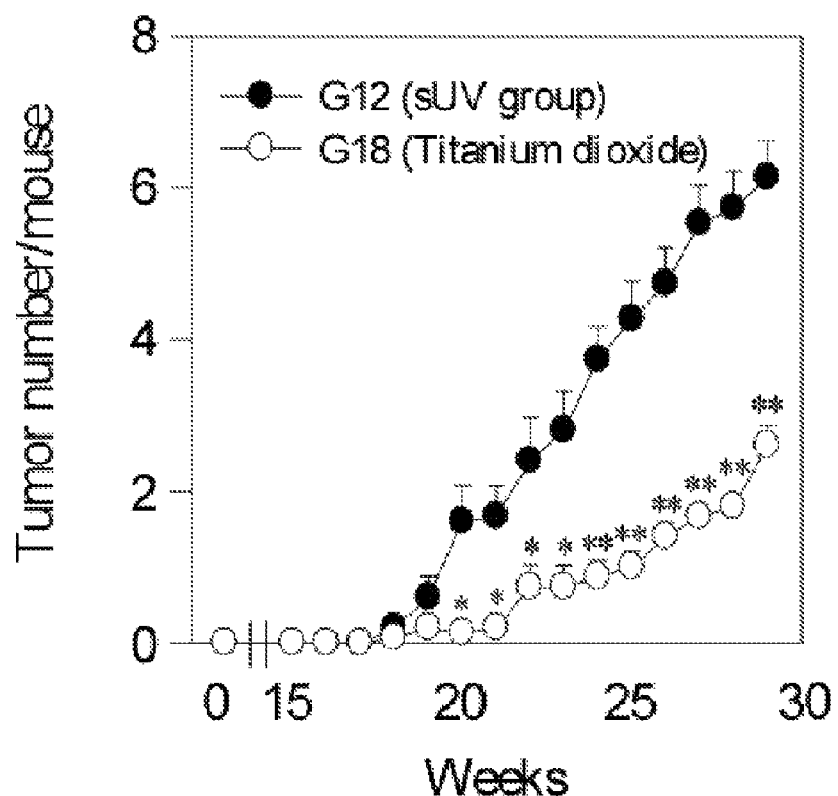
FIG. 33B is a chart illustrating average tumor number in response to solar ultraviolet exposure in a group of mice treated with titanium dioxide compared to a group of untreated mice.
Figure 34A:
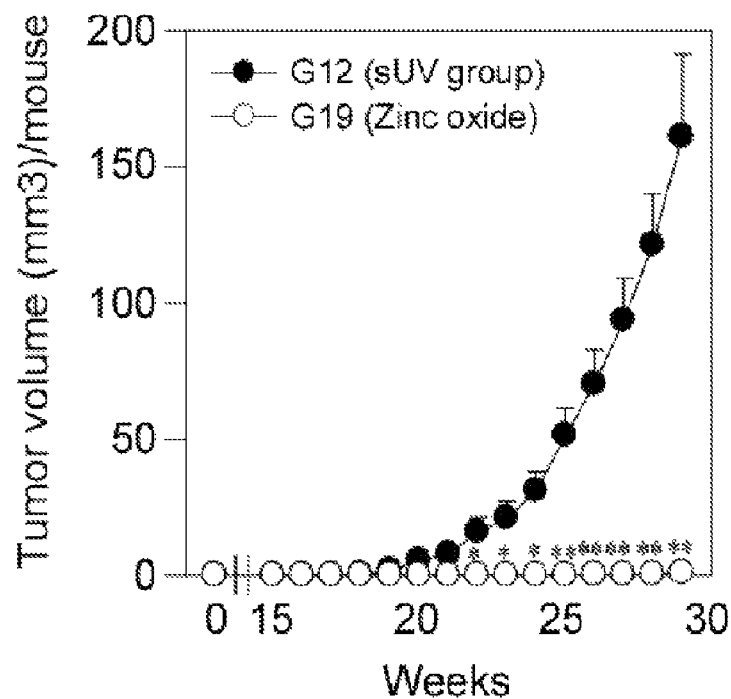
FIG. 34A is a chart illustrating average tumor volume in response to solar ultraviolet exposure in a group of mice treated with zinc oxide compared to a group of untreated mice.
Figure 34B:
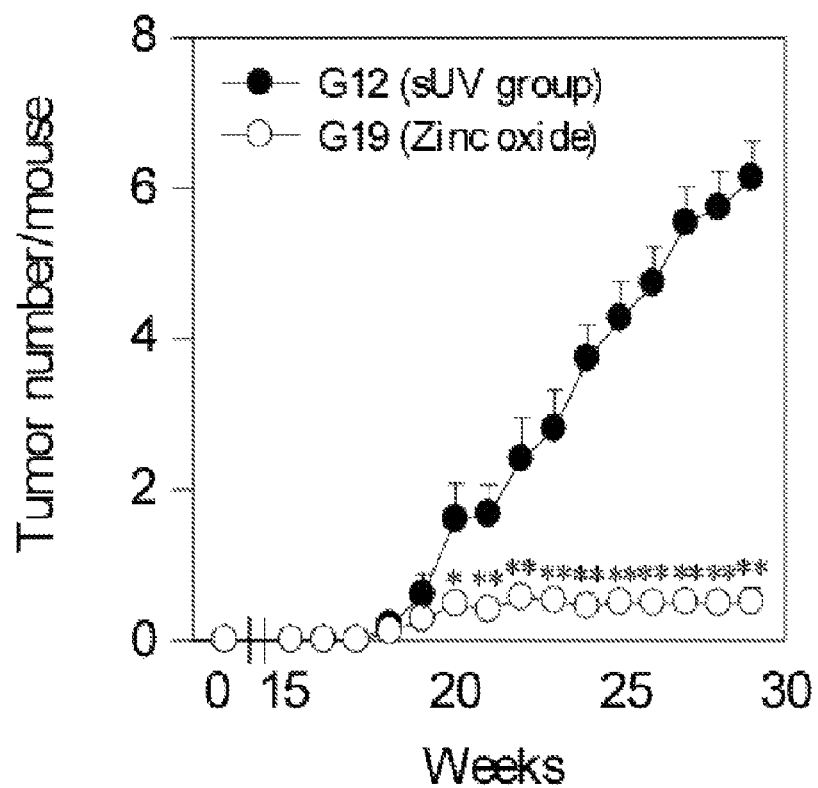
FIG. 34B is a chart illustrating average tumor number in response to solar ultraviolet exposure in a group of mice treated with zinc oxide compared to a group of untreated mice.
Figure 35A:
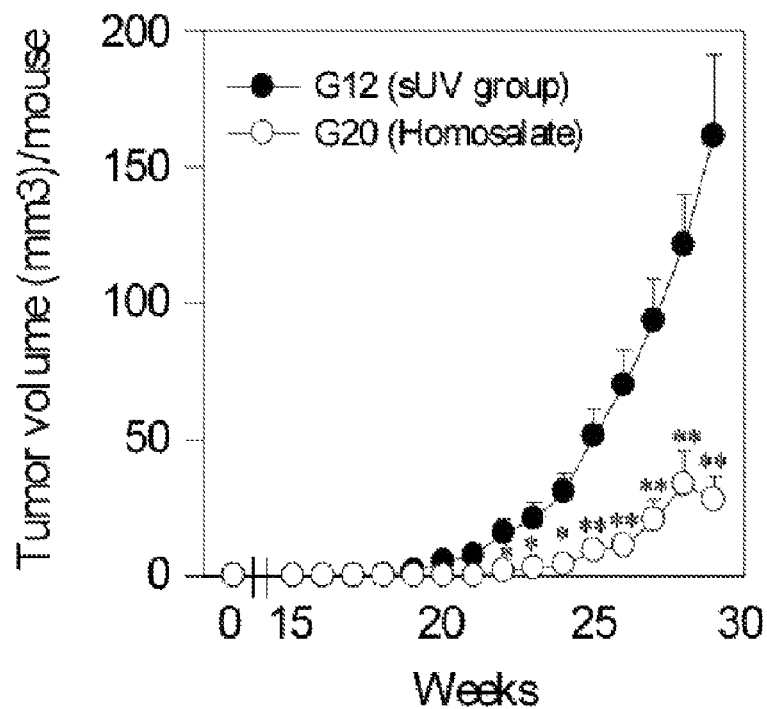
FIG. 35A is a chart illustrating average tumor volume in response to solar ultraviolet exposure in a group of mice treated with homosalate compared to a group of untreated mice.
Figure 35B:
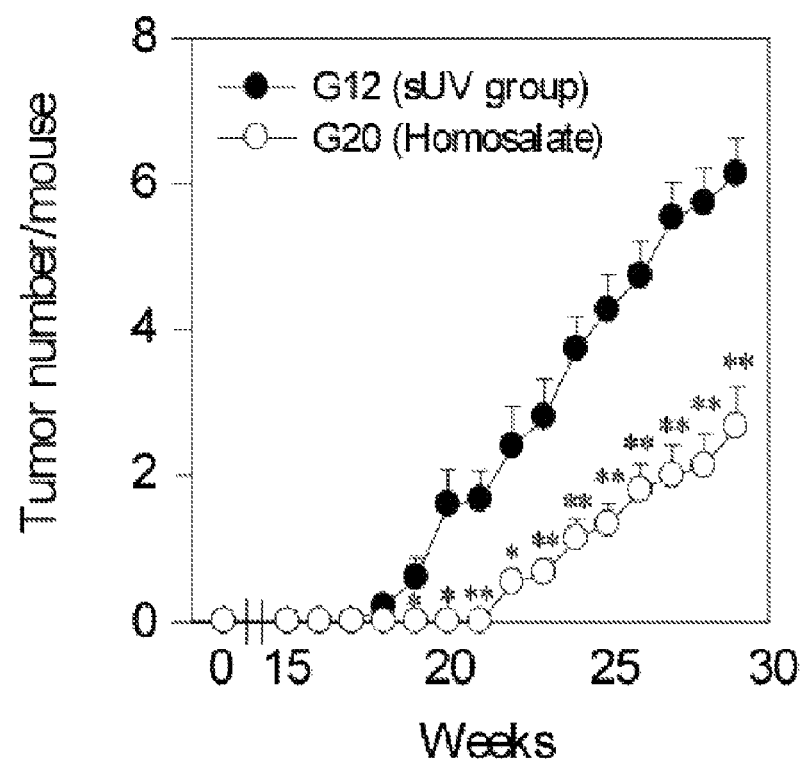
FIG. 35B is a chart illustrating average tumor number in response to solar ultraviolet exposure in a group of mice treated with homosalate compared to a group of untreated mice.
Figure 36A:
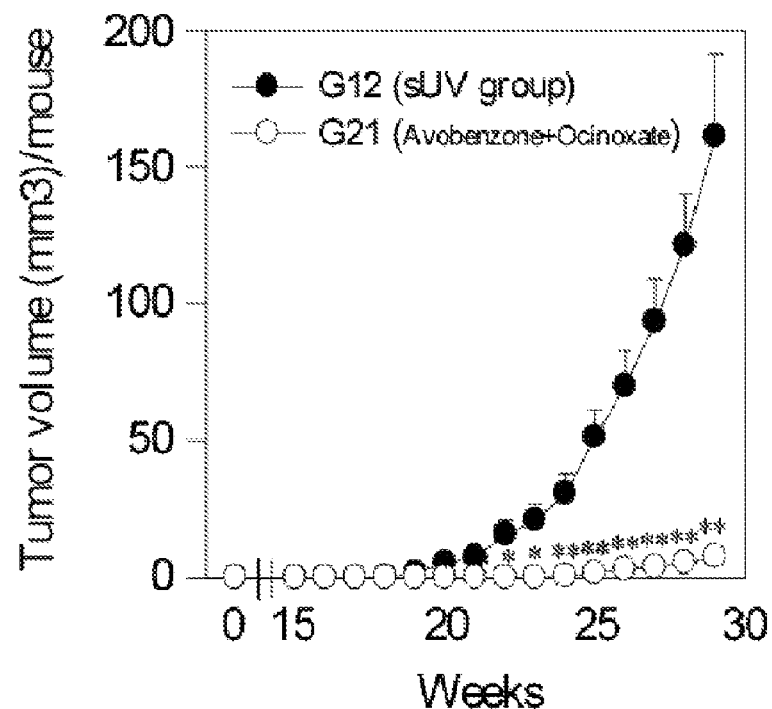
FIG. 36A is a chart illustrating average tumor volume in response to solar ultraviolet exposure in a group of mice treated with a combination of avobenzone and octinoxate compared to a group of untreated mice.
Figure 36B:
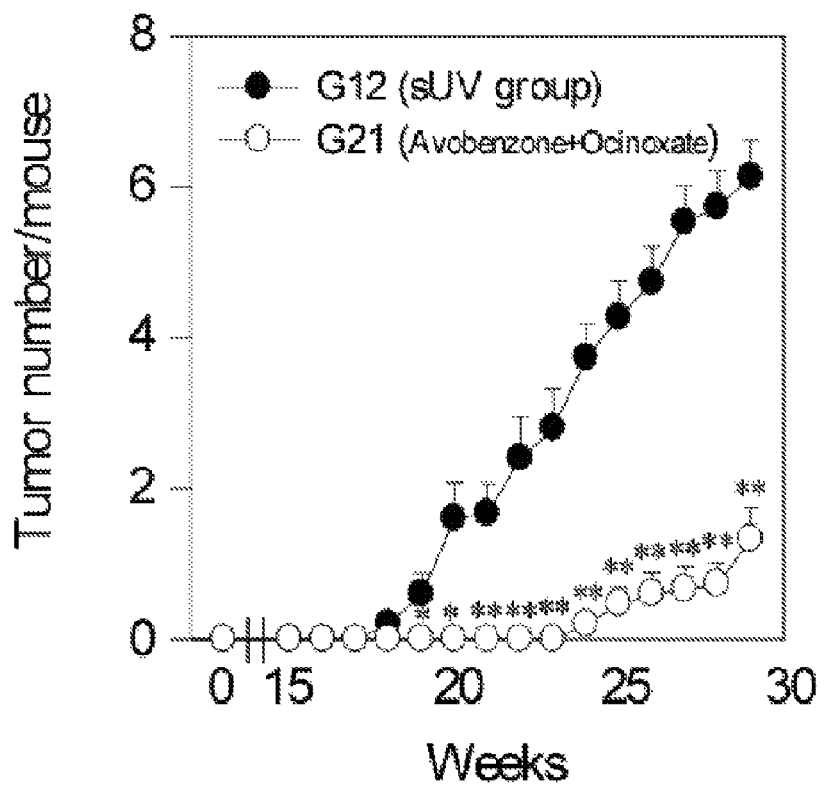
FIG. 36B is a chart illustrating average tumor number in response to solar ultraviolet exposure in a group of mice treated with a combination of avobenzone and octinoxate compared to a group of untreated mice.
Figure 37A:
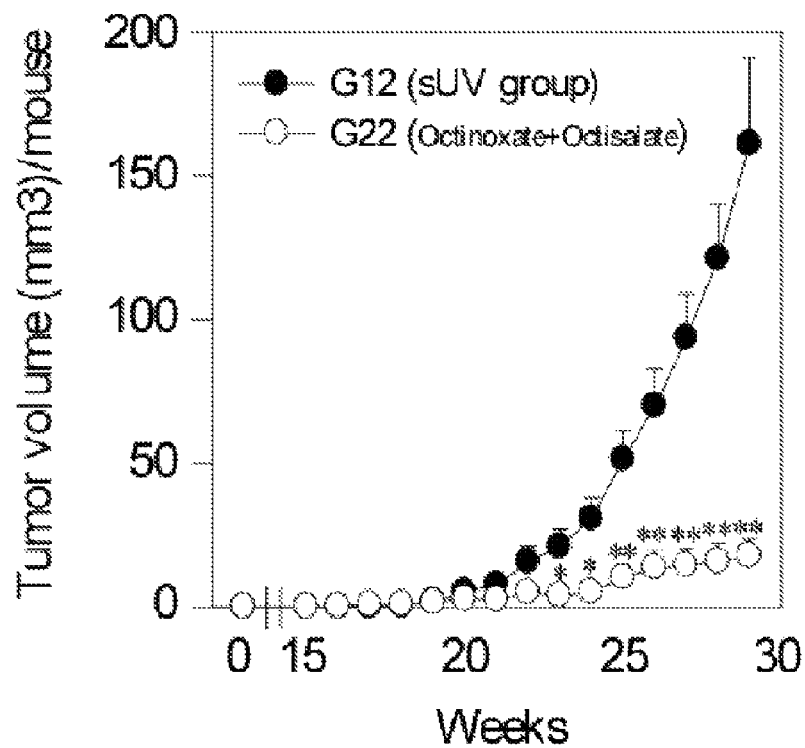
FIG. 37A is a chart illustrating average tumor volume in response to solar ultraviolet exposure in a group of mice treated with a combination of octinoxate and octisalate compared to a group of untreated mice.
Figure 37B:
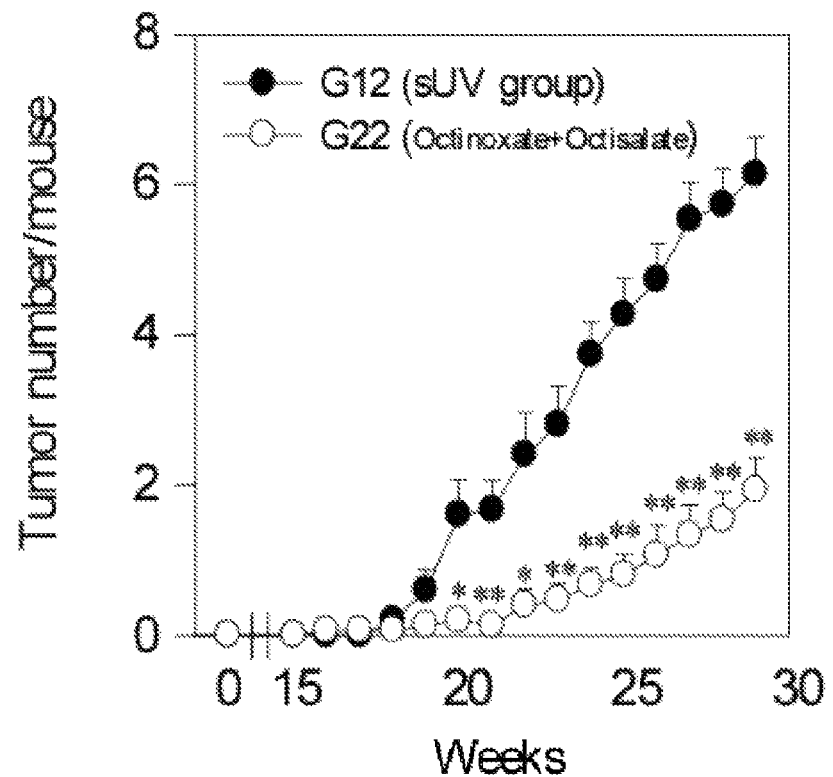
FIG. 37B is a chart illustrating average tumor number in response to solar ultraviolet exposure in a group of mice treated with a combination of octinoxate and octisalate compared to a group of untreated mice.
Figure 38A:
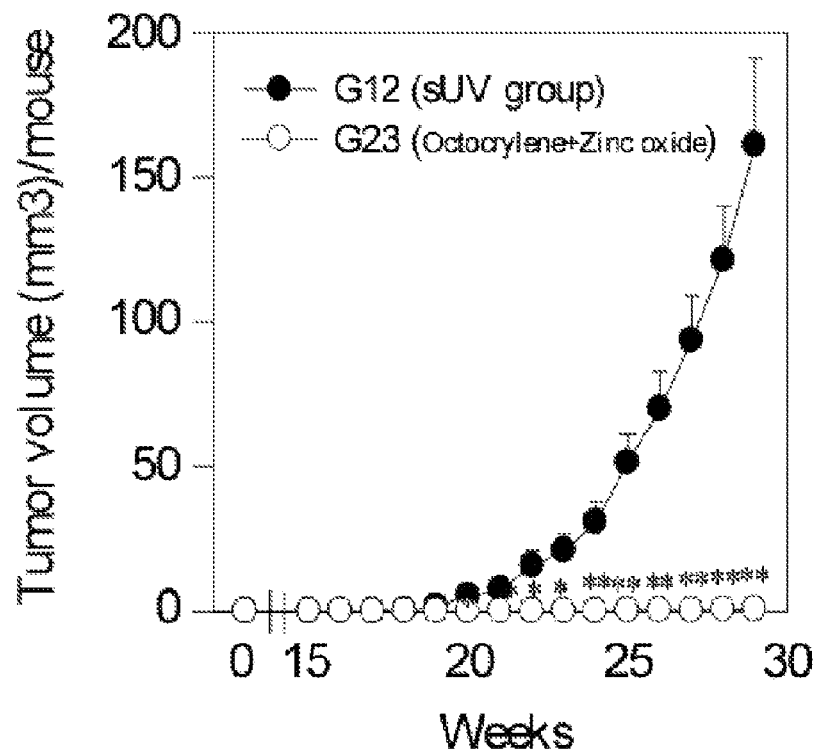
FIG. 38A is a chart illustrating average tumor volume in response to solar ultraviolet exposure in a group of mice treated with a combination of oxtocrylene and zinc oxide compared to a group of untreated mice.
Figure 38B:
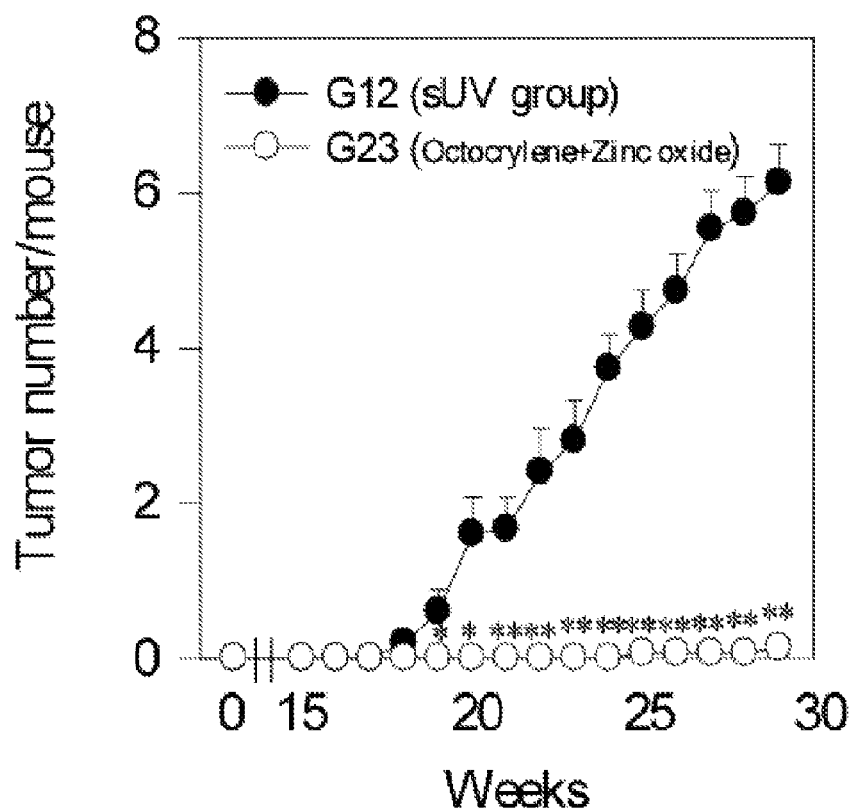
FIG. 38B is a chart illustrating average tumor number in response to solar ultraviolet exposure in a group of mice treated with a combination of octocrylene and zinc oxide compared to a group of untreated mice.
Figure 39A:
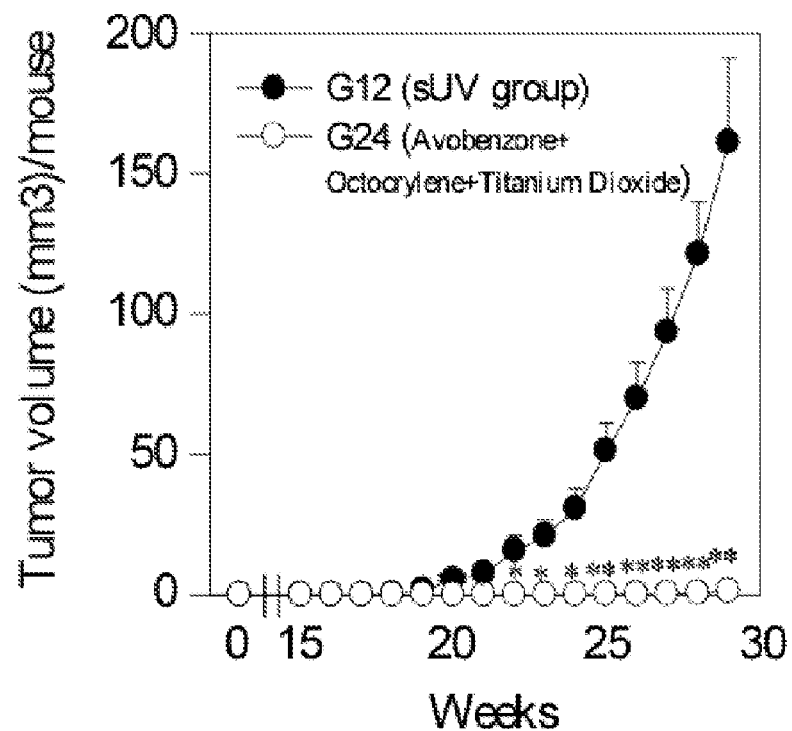
FIG. 39A is a chart illustrating average tumor volume in response to solar ultraviolet exposure in a group of mice treated with a combination of avobenzone, octocrylene, and titanium dioxide compared to a group of untreated mice.
Figure 39B:
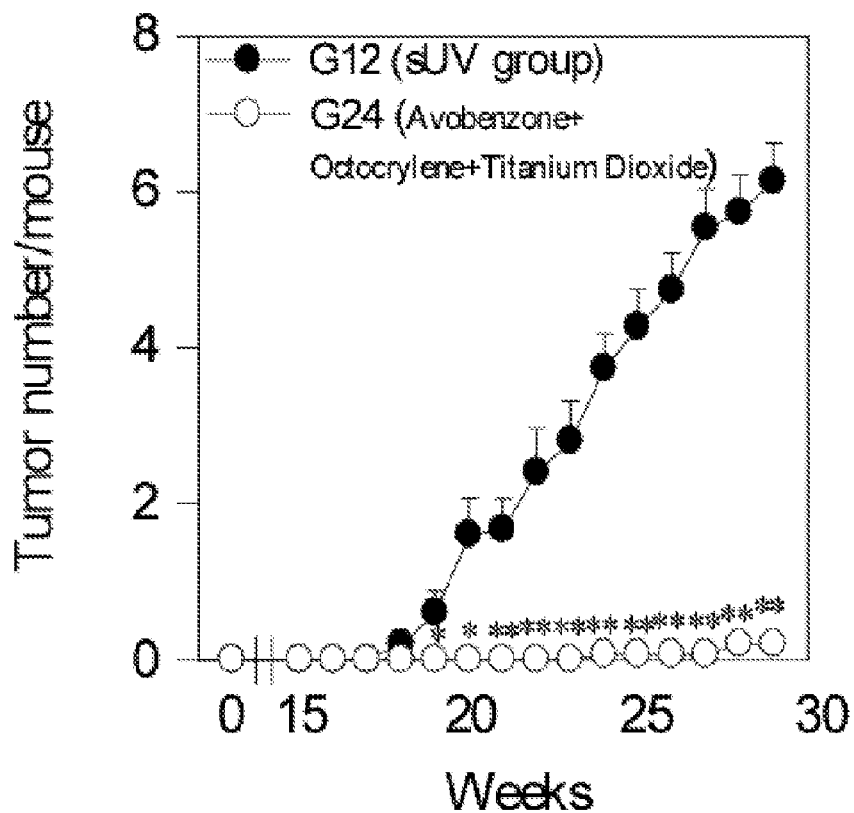
FIG. 39B is a chart illustrating average tumor number in response to solar ultraviolet exposure in a group of mice treated with a combination of avobenzone, octocrylene, and titanium dioxide compared to a group of untreated mice.

FIG. 28A is a chart illustrating average tumor volume in response to solar ultraviolet exposure in a group of mice treated with avobenzone compared to a group of untreated mice. FIG. 28B is a chart illustrating average tumor number in response to solar ultraviolet exposure in a group of mice treated with avobenzone compared to a group of untreated mice. FIG. 29A is a chart illustrating average tumor volume in response to solar ultraviolet exposure in a group of mice treated with octocrylene compared to a group of untreated mice. FIG. 29B is a chart illustrating average tumor number in response to solar ultraviolet exposure in a group of mice treated with octocrylene compared to a group of untreated mice. FIG. 30A is a chart illustrating average tumor volume in response to solar ultraviolet exposure in a group of mice treated with oxybenzone compared to a group of untreated mice. FIG. 30B is a chart illustrating average tumor number in response to solar ultraviolet exposure in a group of mice treated with oxybenzone compared to a group of untreated mice. FIG. 31A is a chart illustrating average tumor volume in response to solar ultraviolet exposure in a group of mice treated with octinoxate compared to a group of untreated mice. FIG. 31B is a chart illustrating average tumor number in response to solar ultraviolet exposure in a group of mice treated with octinoxate compared to a group of untreated mice. FIG. 32A is a chart illustrating average tumor volume in response to solar ultraviolet exposure in a group of mice treated with octisalate compared to a group of untreated mice. FIG. 32B is a chart illustrating average tumor number in response to solar ultraviolet exposure in a group of mice treated with octisalate compared to a group of untreated mice. FIG. 33A is a chart illustrating average tumor volume in response to solar ultraviolet exposure in a group of mice treated with titanium dioxide compared to a group of untreated mice. FIG. 33B is a chart illustrating average tumor number in response to solar ultraviolet exposure in a group of mice treated with titanium dioxide compared to a group of untreated mice. FIG. 34A is a chart illustrating average tumor volume in response to solar ultraviolet exposure in a group of mice treated with zinc oxide compared to a group of untreated mice. FIG. 34B is a chart illustrating average tumor number in response to solar ultraviolet exposure in a group of mice treated with zinc oxide compared to a group of untreated mice. FIG. 35A is a chart illustrating average tumor volume in response to solar ultraviolet exposure in a group of mice treated with homosalate compared to a group of untreated mice. FIG. 35B is a chart illustrating average tumor number in response to solar ultraviolet exposure in a group of mice treated with homosalate compared to a group of untreated mice. FIG. 36A is a chart illustrating average tumor volume in response to solar ultraviolet exposure in a group of mice treated with a combination of avobenzone and octinoxate compared to a group of untreated mice. FIG. 36B is a chart illustrating average tumor number in response to solar ultraviolet exposure in a group of mice treated with a combination of avobenzone and octinoxate compared to a group of untreated mice. FIG. 37A is a chart illustrating average tumor volume in response to solar ultraviolet exposure in a group of mice treated with a combination of octinoxate and octisalate compared to a group of untreated mice. FIG. 37B is a chart illustrating average tumor number in response to solar ultraviolet exposure in a group of mice treated with a combination of octinoxate and octisalate compared to a group of untreated mice. FIG. 38A is a chart illustrating average tumor volume in response to solar ultraviolet exposure in a group of mice treated with a combination of oxtocrylene and zinc oxide compared to a group of untreated mice. FIG. 38B is a chart illustrating average tumor number in response to solar ultraviolet exposure in a group of mice treated with a combination of octocrylene and zinc oxide compared to a group of untreated mice. FIG. 39A is a chart illustrating average tumor volume in response to solar ultraviolet exposure in a group of mice treated with a combination of avobenzone, octocrylene, and titanium dioxide compared to a group of untreated mice. FIG. 39B is a chart illustrating average tumor number in response to solar ultraviolet exposure in a group of mice treated with a combination of avobenzone, octocrylene, and titanium dioxide compared to a group of untreated mice.

No tumors were observed in any animal that received sunblock ingredients in cream and not exposed to solar simulated light (SSL). The positive controls included mice exposed to SSL without vehicle and SSL with cream vehicle. No statistically significant difference was observed between these two positive controls. One hundred percent of mice exposed to SSL with or without topical application of cream before SSL developed tumors. In addition, all mice treated with only titanium dioxide or octisalate in cream developed tumors. Zinc oxide, alone or in combination with octocrylene, or the combination of avobenzone+octocrylene+titanium dioxide had an effectiveness of at least 99% in preventing skin cancer.

Tumors were counted by sight. The dimensions of each tumor were measured using a digital caliper. Tumor volume (mm³) was determined as (length×width²)×0.52, where the length and width were measured in mm. For example, a length of 11 mm and a width of 10 mm results in a tumor volume of 572 mm³ (11×10×10×0.52). Average or total tumor volumes were compared between vehicle (cream)-treated mice exposed to SSL and compound in cream-treated mice exposed to SSL. For example, for avobenzone, the average or total tumor volume for the group was 46.1 or 691.5 mm³, respectively. The average or total tumor volume for vehicle (cream only)-treated mice was 169.4 or 2,540.5 mm³, respectively. The % reduction in volume was 100× (169.4−46.1)/169.4, or a 72.8% reduction in average (or total) tumor volume. Thus the % reduction in volume was considered a measure of effectiveness of the compound or combination of compounds (TABLE 6). Notably, a relatively high mortality rate of mice was observed in the groups treated with octisalate or octisalate combined with octinoxate, respectively, 66.7 and 33.3% (TABLE 6).

Figure 40:
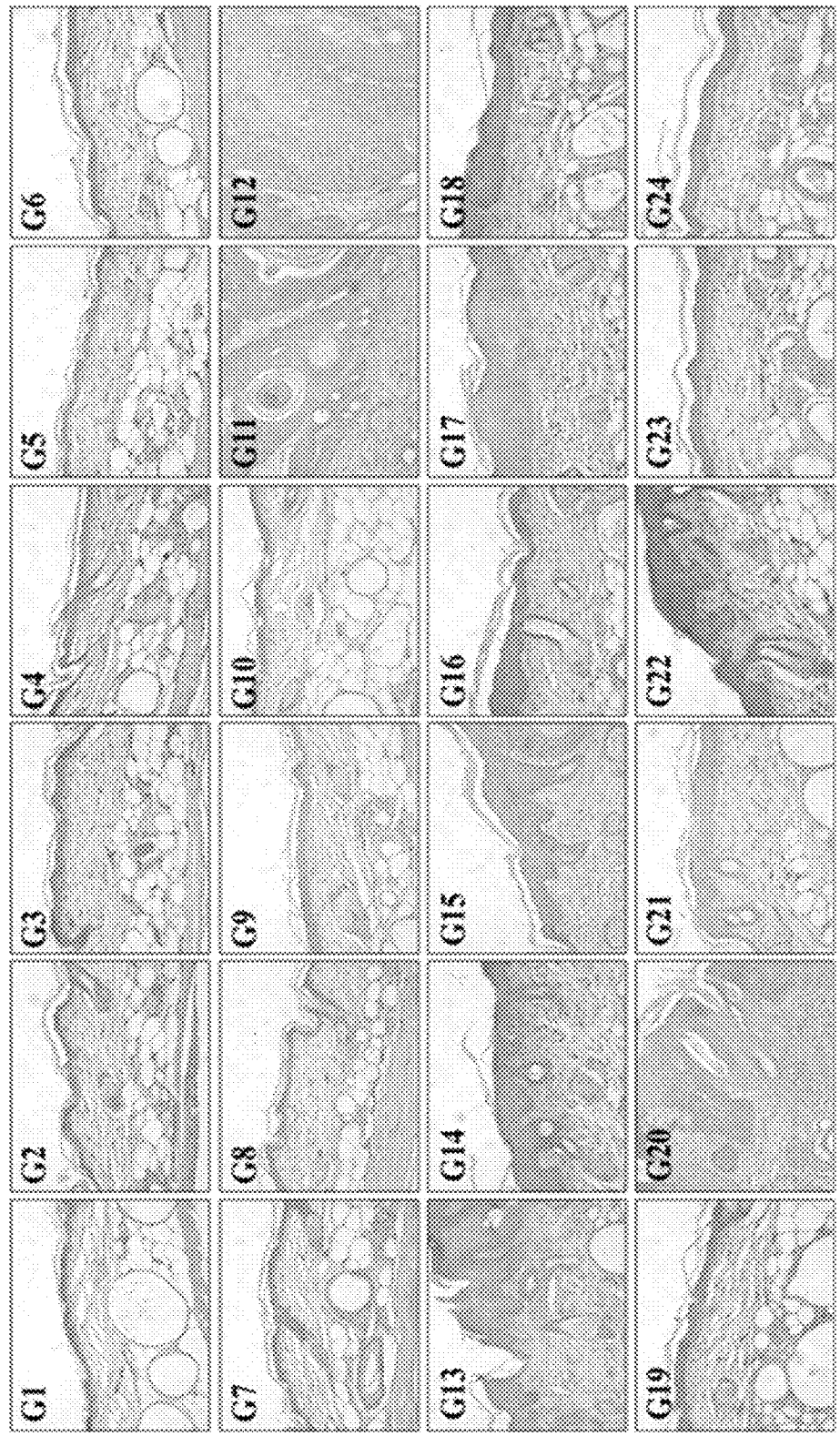
FIG. 40 is a photograph comparing H&E (hematoxylin and eosin) stained tissue sample of mice exposed to solar ultraviolet and treated with anti-sUV agents and mice unexposed to solar ultraviolet.

FIG. 40 is a photograph comparing H&E (hematoxylin and eosin) stained tissue sample of mice exposed to solar ultraviolet and treated with anti-sUV agents and mice unexposed to solar ultraviolet. H&E staining can show skin damage (see TABLE 5 for group identification). As seen in FIG. 40, G (Group) 1-10 are skin samples from mice that were treated as indicated in TABLE 5 but not exposed to solar UV. None of the compounds in the absence of solar UV caused any damage and none had any adverse effect on skin thickness. G11 and G12 are the positive controls, being groups treated with solar UV without or with vehicle (cream). They stained very dark indicating intense damage and G20 (homosalate in cream) was similarly stained. G13 (Avobenzone, anti-UVA), G14 (Octocrylene, anti-UVB), G17 (Octisalate, anti-UVB), G18 (Titanium dioxide, anti-UVA/UVB), and G22 (Octinoxate+Octisalate, anti-UVB) showed epidermal thickening and skin damage. This indicates that compounds blocking only UVA or UVB are ineffective in preventing solar UV-induced skin damage. G15 (Oxybenzone, anti-UVA/UVB) and G16 (Octinoxate, anti-UVB) showed epidermal thickening but less damage. The most protected mice were in G19 (Zinc oxide, UVA/UVB), 21 (Avobenzone+Octinoxate, UVA/UVB), G23 (Octocrylene+Zinc Oxide, UVA/UVB), and G24 (Avobenzone+Octocrylene+Titanium Dioxide, UVA/UVB). Thus, blocking both UVA and UVB prevents solar UV-induced epidermal thickening and skin damage.

Figure 41:
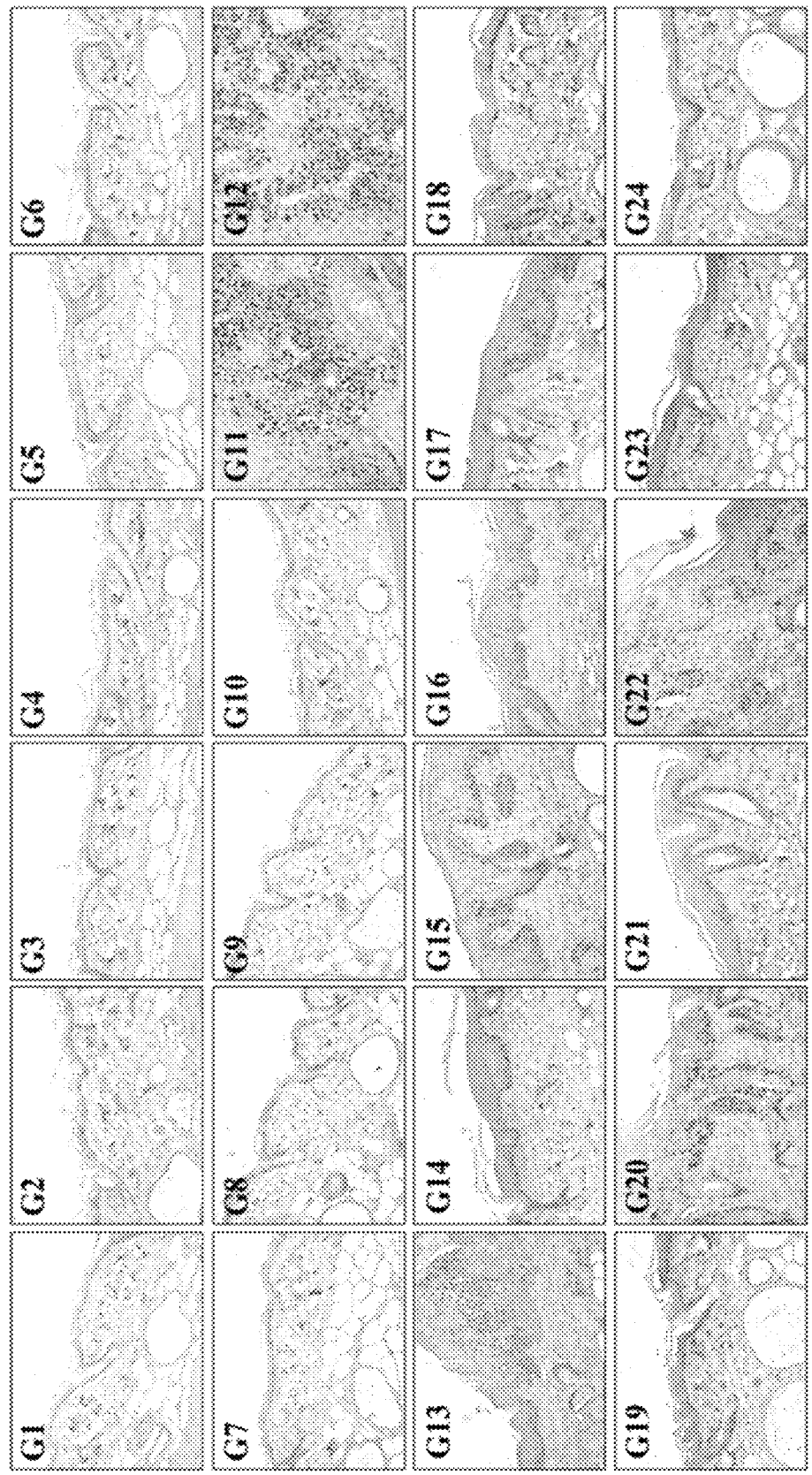
FIG. 41 is a photograph comparing Ki-67 immunohistological-stained tissue samples of mice exposed to solar ultraviolet and treated with anti-sUV agents and mice unexposed to solar ultraviolet.

FIG. 41 is a photograph comparing Ki-67 immunohistological-stained tissue samples of mice exposed to solar ultraviolet and treated with anti-sUV agents and mice unexposed to solar ultraviolet. Ki-67 staining shows the extent of abnormal cell proliferation, which can lead to skin cancer. As seen in FIG. 41, the most proliferation is observed in G11 and G12, which are groups exposed to solar UV and not treated or treated with vehicle (positive controls). G13, G20 and G22 show extensive abnormal proliferation. The least amount of abnormal proliferation is observed in G19, G21, G23 and G24 agreeing with the H&E results in FIG. 40. The remaining groups showed moderate increases in abnormal proliferation.

TABLE 5

| Group number | Sun block Compound/Treatment | Percent | SSL Exposure | Number of Mice |
|---|---|---|---|---|
| 1 | None | N/A | No | 10 |
| 2 | Cream only | N/A | No | 10 |
| 3 | Avobenzone (UVA) | 3% | No | 10 |
| 4 | Octocrylene (UVB/short-wave UVA) | 10% | No | 10 |
| 5 | Oxybenzone (UVB/short-wave UVA) | 6% | No | 10 |
| 6 | Octinoxate (UVB) | 7.50% | No | 10 |
| 7 | Octisalate (UVB) | 5% | No | 10 |
| 8 | Titanium dioxide (UVB/short-wave UVA) | 12% | No | 10 |
| 9 | Zinc oxide (UVA/UVB) | 20% | No | 10 |
| 10 | Homosalate (UVB) | 10% | No | 10 |
| 11 | SSL only | N/A | Yes | 15 |
| 12 | SSL with cream only | N/A | Yes | 15 |
| 13 | Avobenzone (UVA) | 3% | Yes | 15 |
| 14 | Octocrylene (UVB/short-wave UVA | 10% | Yes | 15 |
| 15 | Oxybenzone (UVB/short-wave UVA) | 6% | Yes | 15 |
| 16 | Octinoxate (UVB) | 7.50% | Yes | 15 |
| 17 | Octisalate (UVB) | 5% | Yes | 15 |
| 18 | Titanium dioxide (UVB/short-wave UVA) | 12% | Yes | 15 |
| 19 | Zinc oxide (UVA/UVB) | 20% | Yes | 15 |
| 20 | Homosalate (UVB) | 10% | Yes | 15 |
| 21 | Avobenzone + Octinoxate | 3 + 7.5% | Yes | 15 |
| 22 | Octinoxate + Octisalate | 7.5 + 5% | Yes | 15 |
| 23 | Octocrylene + Zinc Oxide | 7 + 6.9% | Yes | 15 |
| 24 | Avobenzone + Octocrylene + Titanium Dioxide | 3 + 7 + 6% | Yes | 15 |

TABLE 6

| Compound/Treatment | Group/SSL | % Mice with tumor | Total/Avg. no. of tumors | Total/Average volume of tumors | % Mortality/Number of dead mice | % Effective Protection |
|---|---|---|---|---|---|---|
| No treatment | 1-NO | 0 | 0 | 0 | 0 | N/A |
| Cream only | 2-NO | 0 | 0 | 0 | 0 | N/A |
| Avobenzone | 3-NO | 0 | 0 | 0 | 0 | N/A |
| Octocrylene | 4-NO | 0 | 0 | 0 | 0 | N/A |
| Oxybenzone | 5-NO | 0 | 0 | 0 | 0 | N/A |
| Octinoxate | 6-NO | 0 | 0 | 0 | 0 | N/A |
| Octisalate | 7-NO | 0 | 0 | 0 | 0 | N/A |
| Titanium dioxide | 8-NO | 0 | 0 | 0 | 0 | N/A |
| Zinc oxide | 9-NO | 0 | 0 | 0 | 0 | N/A |
| Homosalate | 10-NO | 0 | 0 | 0 | 0 | N/A |
| SSL only | 11-YES | 100 | 101/6.7 | 2421.1/161.4 | 26.7/4 | N/A |
| SSL cream | 12-YES | 100 | 91/6.1 | 2540.5/169.4 | 20/3 | N/A |
| Avobenzone | 13-YES | 93.3 | 55/3.7 | 691.5/46.1 | 6.7/1 | 72.8 |
| Octocrylene | 14-YES | 66.7 | 25/1.7 | 246.7/16.5 | 0/0 | 90.3 |
| Oxybenzone | 15-YES | 86.7 | 35/2.3 | 213.7/14.3 | 6.7/1 | 91.2 |
| Octinoxate | 16-YES | 80 | 21/1.4 | 156.02/10.4 | 13.3/2 | 93.9 |

TABLE 6-continued

| Compound/Treatment | Group/SSL | % Mice with tumor | Total/Avg. no. of tumors | Total/Average volume of tumors | % Mortality/Number of dead mice | % Effective Protection |
|---|---|---|---|---|---|---|
| Octisalate | 17-YES | 100 | 39/2.6 | 758.4/50.6 | 66.7/10 | 70.1 |
| Titanium dioxide | 18-YES | 100 | 39/2.6 | 275.6/18.4 | 13.3/2 | 89.2 |
| Zinc oxide | 19-YES | 6.7 | 2/0.13 | 11.2/0.8 | 0/0 | 99.6 |
| Homosalate | 20-YES | 80 | 39/2.6 | 415.7/27.7 | 6.7/1 | 83.6 |
| Avobenzone + Octinoxate | 21-YES | 53.3 | 20/1.3 | 114.3/7.6 | 13.3/2 | 95.5 |
| Octinoxate + Octisalate | 22-YES | 80 | 29/1.9 | 261.9/17.5 | 33.3/5 | 89.7 |
| Octocrylene + Zinc Oxide | 23-YES | 13.3 | 2/0.13 | 10.3/0.7 | 0/0 | 99.6 |
| Avobenzone + Octocrylene + Titanium dioxide | 24-YES | 20 | 3/0.2 | 17.9/1.2 | 6.7/1 | 99.3 |

Comparative Example 1

The effect of a proprietary moisturizer (MZ) and a proprietary sunblock (SB) on carcinogenicity of UVA light was evaluated using mice models. The moisturizer MZ included purified water, white petrolatum, sorbitol solution, cetearyl alcohol, propylene glycol, ceteareth-20, simethicone, glyceryl monostearate, polyethylene glycol monostearate, sorbic acid, and butylated hydroxytoluene. The sunblock SB included titanium dioxide, zinc oxide, C20-40 alcohols, caprylyl glycol, cetyl PEG/PPG-10/1 dimethicone, cocoglycerides, dicaprylyl carbonate, dimethicone, 1,2 hexanediol, hydrogenated castor oil, hydrogenated polyisobutene, magnesium chloride, octadecene, PEG-30 dipolyhydroxystearate, pentylene glycol, phenyl trimethicone, purified water, silica, silica dimethyl silylate, squalane, stearyl dimethicone, tridecyl salicylate, triethoxycaprylylsilane, and ubiquinone (coenzyme Q10).

Figure 42A:
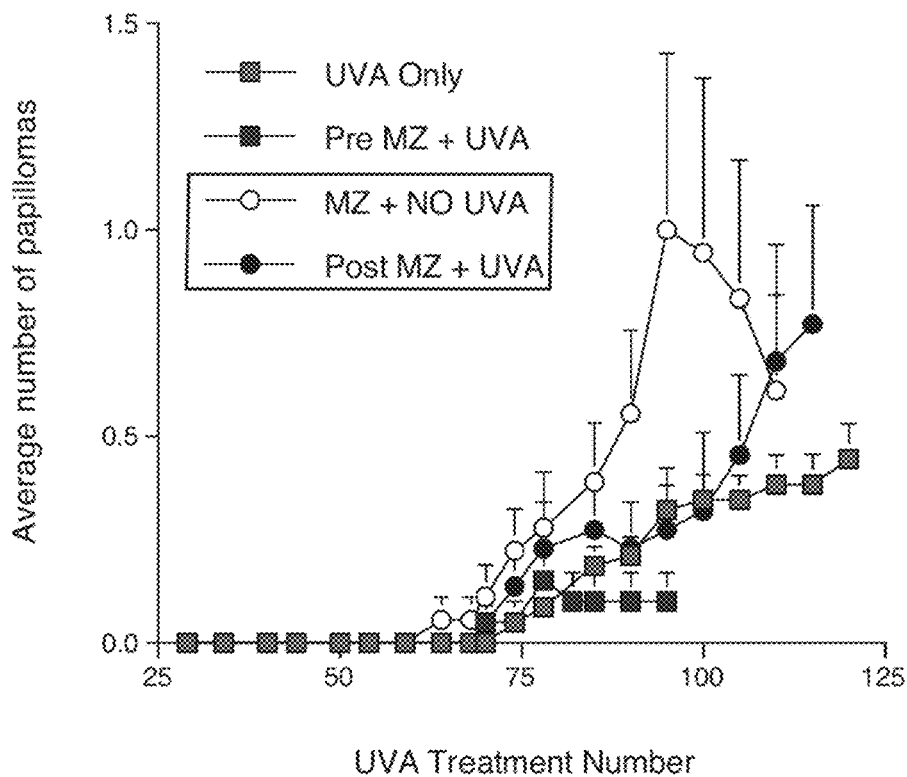
FIG. 42A is a chart illustrating the average number of papillomas in mice treated with a moisturizer and exposed to ultraviolet A (UVA) light.
Figure 42B:
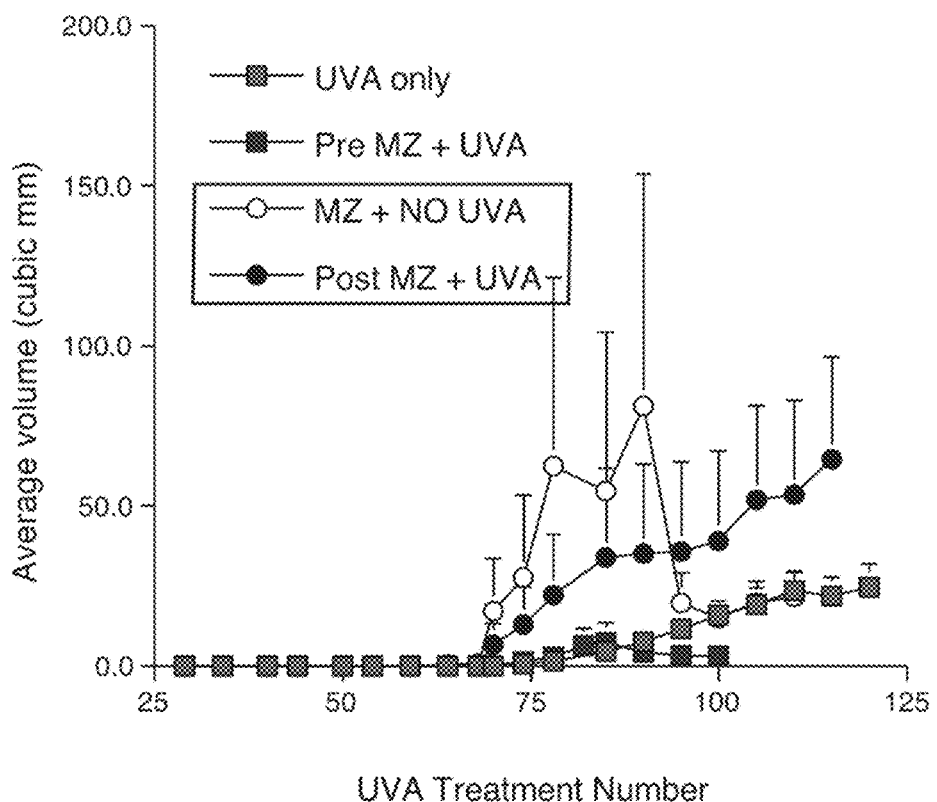
FIG. 42B is a chart illustrating the average volume of papillomas in mice treated with a moisturizer and exposed to ultraviolet A (UVA) light.
Figure 42C:
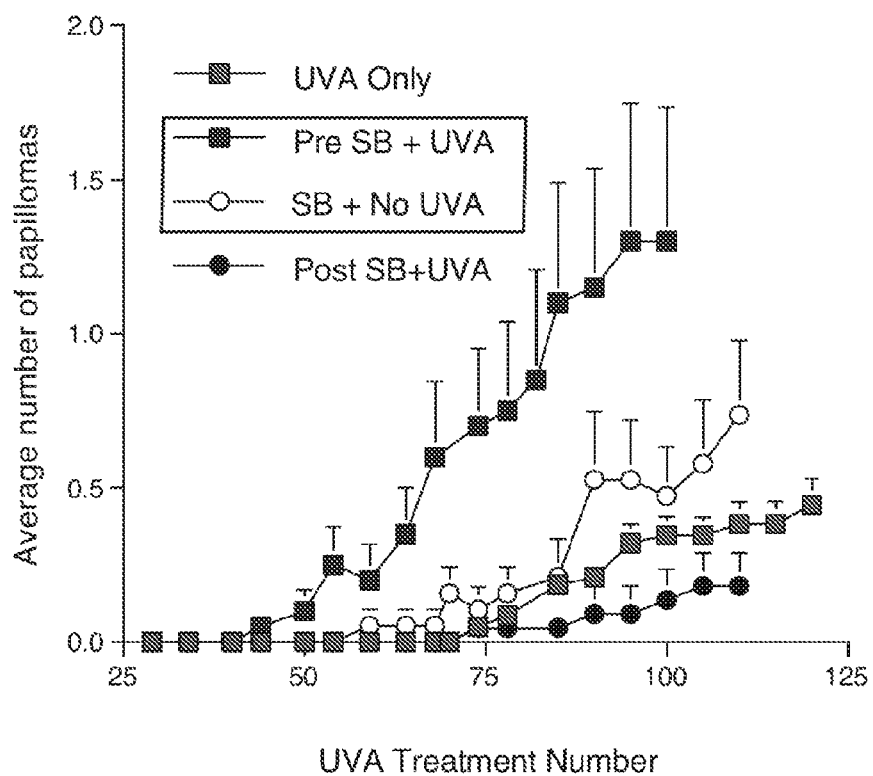
FIG. 42C is a chart illustrating the average number of papillomas in mice treated with a sunblock and exposed to ultraviolet A (UVA) light.
Figure 42D:
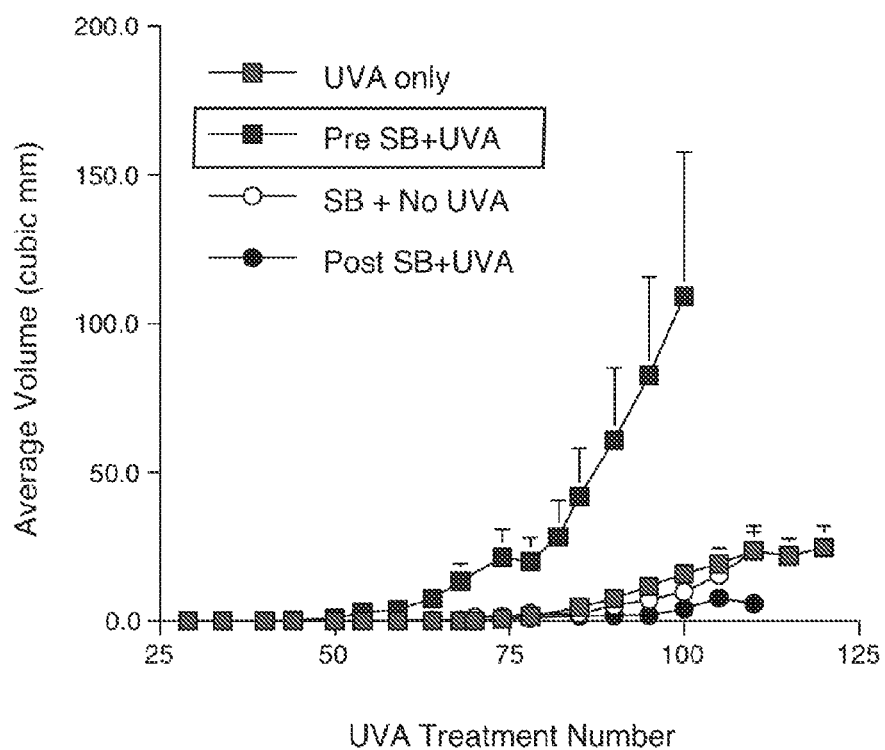
FIG. 42D is a chart illustrating the average volume of papillomas in mice treated with a sunblock and exposed to ultraviolet A (UVA) light.

The development of tumors (papillomas) in mouse skin was monitored before and after UVA exposure by a predetermined number of UVA treatments, and with or without the application of the test skin formulation. The results are illustrated in FIGS. 42A-42D. FIG. 42A is a chart illustrating the average number of papillomas in mice treated with the moisturizer MZ and exposed to ultraviolet A (UVA) light. FIG. 42B is a chart illustrating the average volume of papillomas in mice treated with the moisturizer MZ and exposed to ultraviolet A (UVA) light. FIG. 42C is a chart illustrating the average number of papillomas in mice treated with the sunblock SB and exposed to ultraviolet A (UVA) light. FIG. 42D is a chart illustrating the average volume of papillomas in mice treated with the sunblock SB and exposed to ultraviolet A (UVA) light.

Mice treated with the moisturizer MZ or the sunblock SB with or without exposure to UVA exhibited papillomas, as seen in FIGS. 42A and 42B. In particular, whether before UVA exposure or after UVA exposure, both tumor number (FIG. 42A) and tumor volume (FIG. 42B) were greater in mice treated with the moisturizer MZ than in mice not treated with the moisturizer MZ. Similarly, whether before UVA exposure or after UVA exposure, both tumor number (FIG. 42A) and tumor volume (FIG. 42B) were greater in mice treated with the sunblock SB than in mice not treated with the sunblock SB. Thus, treatment with the moisturizer MZ and the sunblock SB appears to promote papilloma formation and growth, regardless of whether UVA also contributed to papilloma formation and growth.

Example 18

An example skin care formulation was prepared. Two phases were prepared. The first phase, phase A, included 0.05 g EDTA-2Na, 3 ml 1,3-butylene glycol, 4 ml glycerin, 2 ml pentylene glycol, and balance distilled water to prepare 100 ml of phase A composition. The second phase, phase B, included 1.2 g cetyl alcohol, 1.5 g glyceryl stearate, and 8 g poly (1-decene). All ingredients in phase A were mixed and heated to 75° C. in a glass beaker until all of the ingredients are dissolved. Similarly, all ingredients in phase B were mixed and heated to about 75° C. in another glass beaker. The phase B composition was gradually introduced into the phase A composition as the phase A composition was stirred vigorously at 1500-2000 revolutions per minute (rpm) at 70° C. to result in emulsification of phase A and phase B. The rate of stirring was increased to about 3000 rpm while maintaining the temperature at about 70° C. The mixture was allowed to cool to 30° C. while reducing the stirring rate to about 1500 rpm. After cooling, stirring was stopped to obtain the example skin care formulation.

Example 19

Figure 43A:
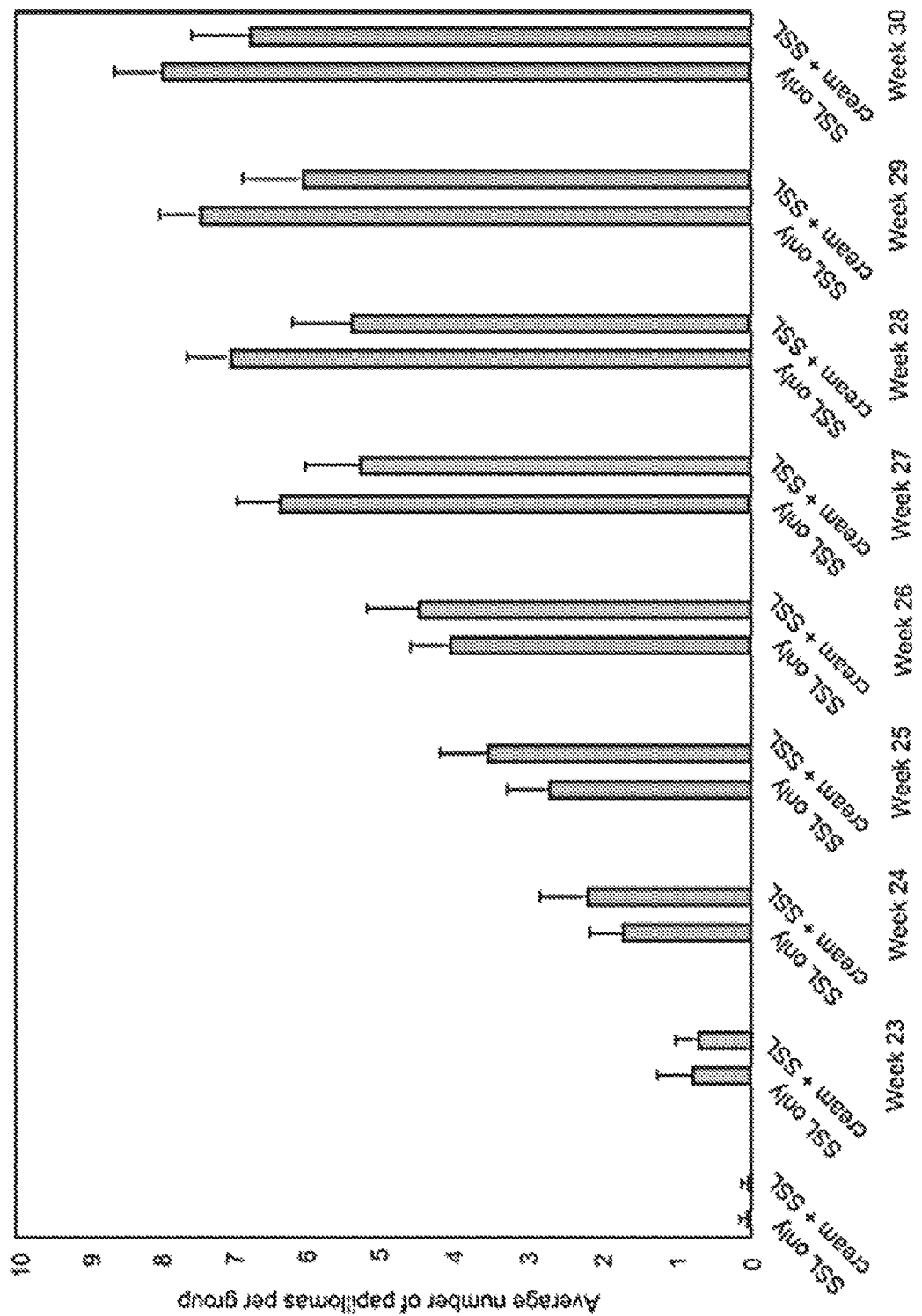
FIG. 43A is a chart illustrating the change in the average number of papillomas with time in mice treated with an example skin care formulation and exposed to solar simulated light (SSL).
Figure 43B:
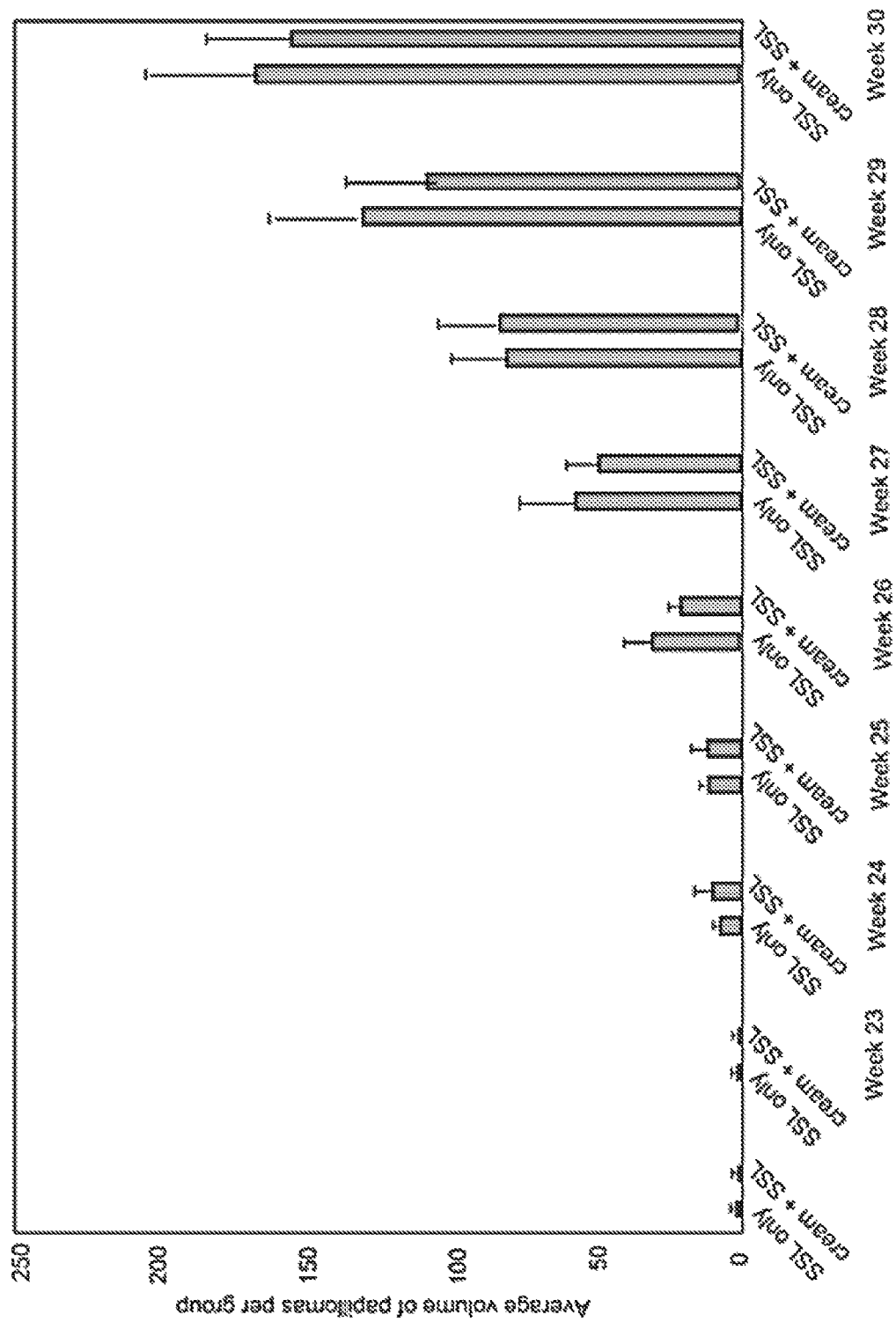
FIG. 43B is a chart illustrating the change in the average volume of papillomas with time in mice treated with an example skin care formulation and exposed to solar simulated light (SSL).
Figure 44A:
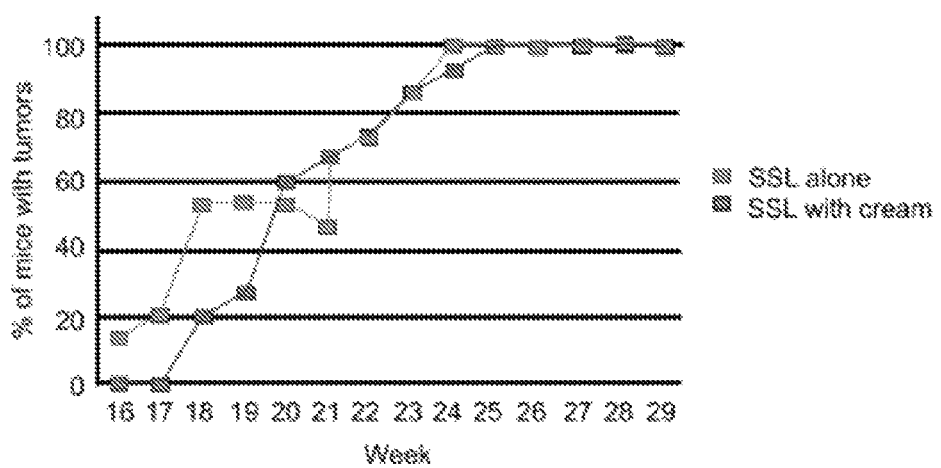
FIG. 44A is a chart illustrating the change in the percentage of papillomas with time in per group of mice treated with an example skin care formulation and exposed to solar simulated light (SSL).
Figure 44B:
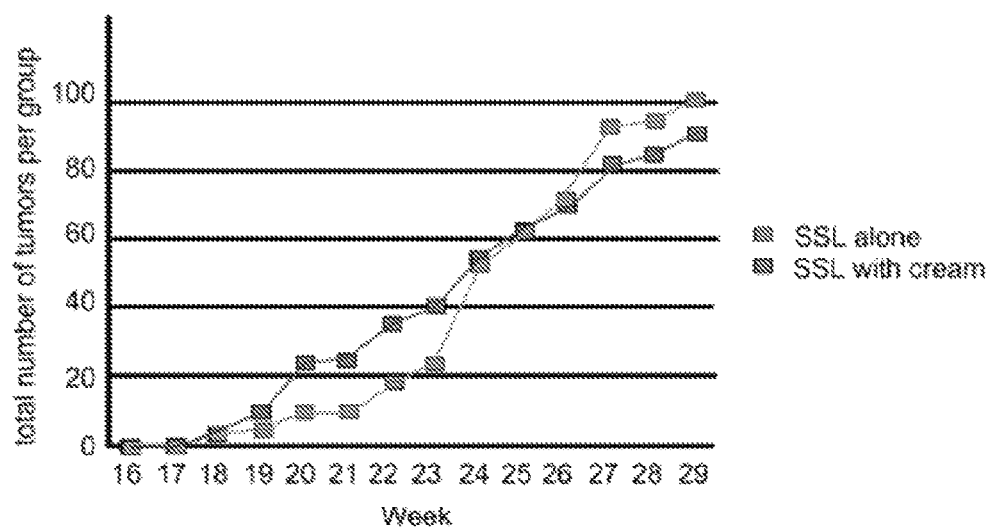
FIG. 44B is a chart illustrating the change in the total number of papillomas with time per group of mice treated with an example skin care formulation and exposed to solar simulated light (SSL).
Figure 44C:
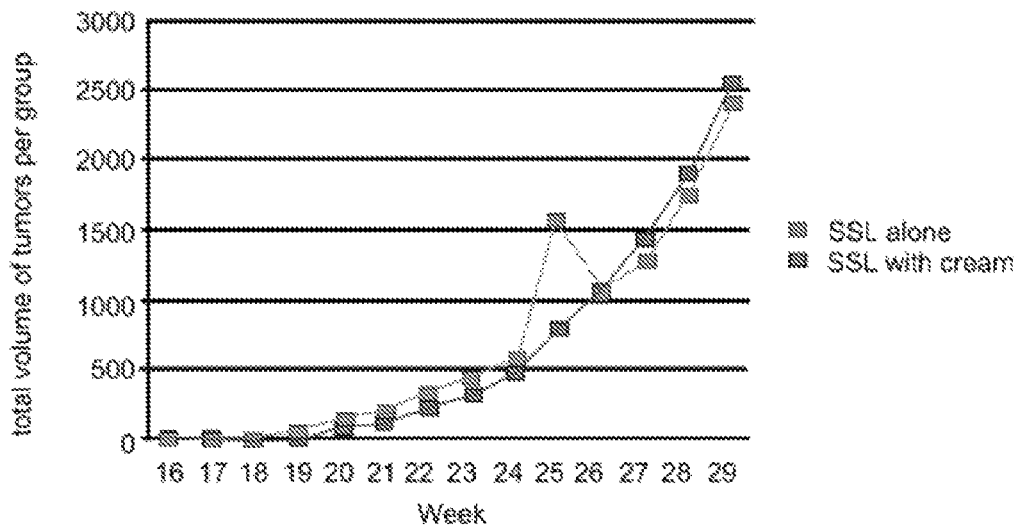
FIG. 44C is a chart illustrating the change in the total volume of papillomas with time per group of mice treated with an example skin care formulation and exposed to solar simulated light (SSL).

The effect of the skin care formulation of EXAMPLE 18 on papilloma formation was evaluated. Solar simulated light (SSL) including wavelengths ranging from 290-400 nm was used. The SSL spectrum comprises a majority of UVA, which is similar to natural sunlight. The dorsal skin of mice was exposed to SSL irradiation, using a bank of 4 UVA-340 sunlamps (Q-Panel Lab Products, Cleveland, OH). UVA-340 sunlamps emit UV between 295 and 390 nm, which closely resembles the UV spectrum of sunshine through the mid-UVA range. The lamp output was measured using an IL1700 Research Radiometer/Photometer (International Light Technologies, Peabody, MA). The mice were exposed to UV at a distance of 15 inches to minimize the influence of heat from the lamps. The mice were not restrained during UV treatment. The total dose was calculated using the measured value and length of exposure. Doses were environmentally relevant, equal to about 60 min of noon summer sun in Austin, MN The results are shown in FIGS. 43A, 43B, and 44A-44C. FIG. 43A is a chart illustrating the change in the average number of papillomas with time in mice treated with the example skin care formulation of EXAMPLE 18 and exposed to solar simulated light (SSL). FIG. 43B is a chart illustrating the change in the average volume of papillomas with time in mice treated with the example skin care formulation of EXAMPLE 18 and exposed to solar simulated light (SSL). FIG. 44A is a chart illustrating the change in the percentage of papillomas with time in per group of mice treated with the example skin care formulation of EXAMPLE 18 and exposed to solar simulated light (SSL). FIG. 44B is a chart illustrating the change in the total number of papillomas with time per group of mice treated with the example skin care formulation of EXAMPLE 18 and exposed to solar simulated light (SSL). FIG. 44C is a chart illustrating the change in the total volume of papillomas with time per group of mice treated with the example skin care formulation of EXAMPLE 18 and exposed to solar simulated light (SSL).

The results shown in FIGS. 43A, 43B, and 44A-44C indicate that the example skin care formulation of EXAMPLE 18 does not cause skin cancer when placed on mouse skin exposed to solar UV In other words, the skin care formulation is noncarcinogenic, in contrast with the moisturizer MZ and the sunblock SB of COMPARATIVE EXAMPLE 1, which were found to be carconogenic. The average number (FIG. 43A) and volume (FIG. 43B) are not different between mice exposed to SSL. All mice developed tumors and the total number and volume were not different (FIGS. 44A-44C).

Example 20

The effect of adding anti-aging and/or anti-wrinkling compounds to the skin care formulation of EXAMPLE 18 on nuclear factor kappa B (NF-κB) mediated-inflammation was evaluated. Twelve compounds, 7,3,4'-trihydroxyisoflavone, delphiniden, magnolol, 6,7,4'-trihydroxyisoflavone, naringenin, caffeic acid phenylethyl ester (CAPE), 3,7,4'-trihydroxyflavone, myricetin, quercetagetin, isorhamnetin, luteolin, and/or herbacetin were tested. The names and chemical structure of these compounds is indicated in TABLE 7.

TABLE 7

| Compound | Common Name | CAS Number; Mol. Weight | Formula | Structure |
|---|---|---|---|---|
| HI 1 7,3',4'-trihydroxy-isoflavone | 3'-hydroxydaidzein | 485-63-2 MW 270.24 | $C_{15}H_{10}O_5$ | 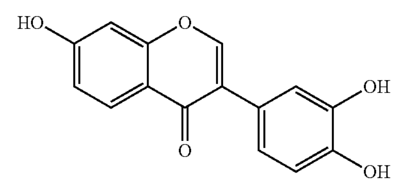 [SMILES: O=c1c(-c2ccc(O)c(O)c2)coc2cc(O)ccc12] |
| HI 2 3,3',4',5,5',7-hexahydroxy-flavylium chloride | delphiniden chloride | 528-53-0 MW 338.7 | $C_{15}H_{11}ClO_7$ | 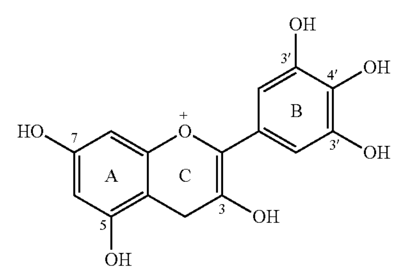 |
| HI 3 5,5'-diallyl-2,2'-biphenyldiol | magnolol | 528-43-8 MW 266.33 | $C_{18}H_{18}O_2$ | 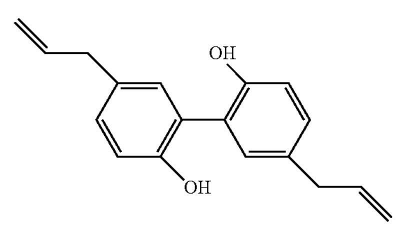 [SMILES: C=CCc1ccc(O)c(-c2cc(CC=C)ccc2O)c1] |
| HI 4 6,7,4'-trihydroxy-isoflavone | | 17817-31-1 MW 270.24 | $C_{15}H_{10}O_5$ | 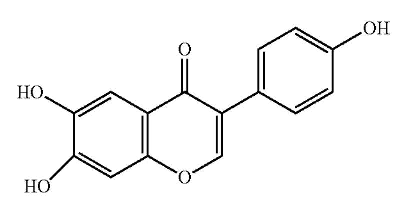 [SMILES: O=c1c(-c2ccc(O)cc2)coc2cc(O)c(O)cc12] |

TABLE 7-continued

| Compound | Common Name | CAS Number; Mol. Weight | Formula | Structure |
|---|---|---|---|---|
| HI 5 5,7-dihydroxy-2-(4-hydroxy-phenyl)-2,3-dihydro-4H-chromen-4-one | naringenin | 480-41-1 MW 272.26 | $C_{15}H_{12}O_5$ | 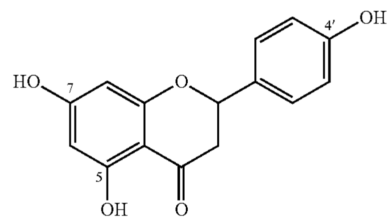 [SMILES: O=C1CC(c2ccc(O)cc2)Oc2cc(O)cc(O)c21] |
| HI 6 phenethyl caffeate | caffeic acid phenylethyl ester (CAPE) | 104594-70-9 MW 284.31 | $C_{17}H_{16}O_4$ | 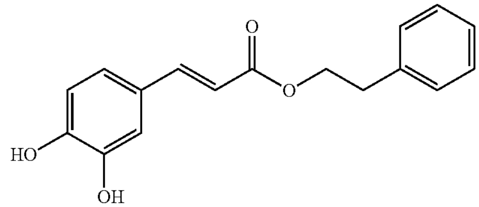 [SMILES: O=C(/C=C/c1ccc(O)c(O)c1)OCCc1ccccc1] |
| HI 7 3,7,4'-trihydroxy-flavone | 5-deoxy-kaempferol | 2034-65-3 MW 270.24 | $C_{15}H_{10}O_5$ | 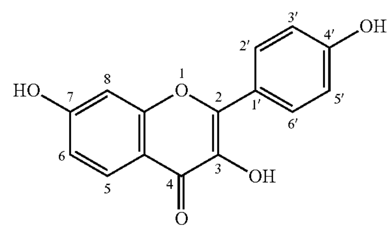 [SMILES: O=c1c(O)c(-c2ccc(O)cc2)oc2cc(O)ccc12] |
| HI 8 3,3',4',5,5',7-hexahydroxy-flavon | myricetin | 529-44-2 MW 318.24 | $C_{15}H_{10}O_8$ | 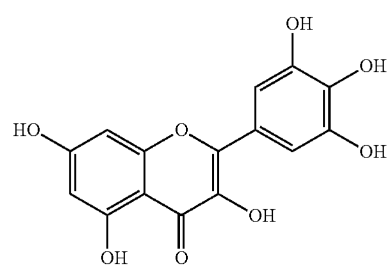 [SMILES: O=c1c(O)c(-c2cc(O)c(O)c(O)c2)oc2cc(O)cc(O)c12] |
| HI 9 3,3',4',5,6,7-hexahydroxy-flavone | quercetagetin | 90-18-6 MW 218.24 | $C_{15}H_{10}O_8$ | 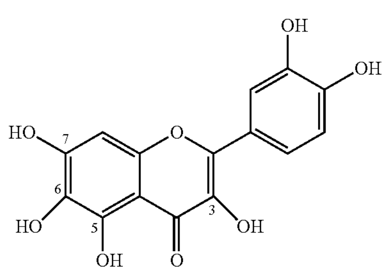 [SMILES: O=c1c(O)c(-c2ccc(O)c(O)c2)oc2cc(O)c(O)c(O)c12] |
| HI 10 3'-methoxy-3,4',5,7-tetrahydroxy-flavone | isorhamnetin | 480-19-3 MW 316.25 | $C_{16}H_{12}O_7$ | 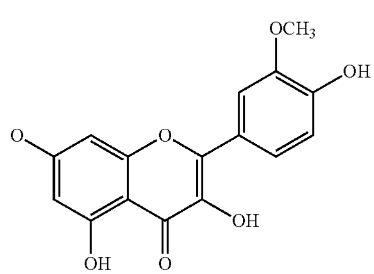 [SMILES: COc1cc(-c2oc3cc(O)cc(O)c3c(=O)c2O)ccc1O] |

TABLE 7-continued

| Compound | Common Name | CAS Number; Mol. Weight | Formula | Structure |
|---|---|---|---|---|
| HI 11 2-(3,4-dihydroxy-phenyl)-5,7-dihydroxy-rh-1-benzo-pyran-4-on | luteolin | 491-70-3 MW 286.24 | $C_{15}H_{10}O_6$ | 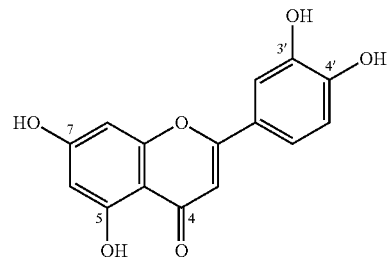 [SMILES: O=c1cc(-c2ccc(O)c(O)c2)oc2cc(O)cc(O)c12] |
| HI 12 3,5,7,8-tetrahydroxy-2-(4-hydroxy-phenyl)-4H-1-benzopyran-4-one | herbacetin | 527-95-7 MW 302.24 | $C_{15}H_{10}O_7$ | 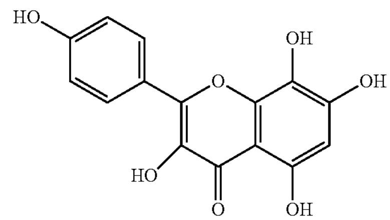 [SMILES: O=c1c(O)c(-c2ccc(O)cc2)oc2c(O)c(O)cc(O)c12] |

A cell-based assay was performed to determine the effective of each of these compounds. The assay involved the effect of each compound on the nuclear factor kappa B (NF-κB) pathway. The inhibition of NF-κB is indicative of a protective effect against aging and wrinkling. The results of the assay using different dosages of each of the compounds are provided in TABLE 8.

TABLE 8

| Compound | Final dose (μg/ml) | % inhibition of NF-κB | Rating |
|---|---|---|---|
| HI-1 | 10 | none | none |
| | 50 | 14% | |
| | 100 | 40% | |
| HI-2 | 10 | none | none |
| | 50 | none | |
| | 100 | none | |
| HI-3 | 10 | >90% | **** (slightly cytotoxic) |
| | 50 | >90% | |
| | 100 | >90% | |
| HI-4 | 10 | none | none |
| | 50 | none | |
| | 100 | none | |
| HI-5 | 10 | none | none |
| | 50 | 56% | |
| | 100 | 62% | |
| HI-6 | 10 | 64% | *** |
| | 50 | >90% | |
| | 100 | >90% | |
| HI-7 | 10 | 9% | none |
| | 50 | 52% | |
| | 100 | 66% | |
| HI-8 | 10 | none | none |
| | 50 | 39% | |
| | 100 | 44% | |
| HI-9 | 10 | none | none |
| | 50 | none | |
| | 100 | 20% | ** |
| HI-10 | 10 | 45% | |
| | 50 | 52% | |
| | 100 | 43% | |
| HI-11 | 10 | 54% | ** |
| | 50 | >90% | |
| | 100 | >90% | |

TABLE 8-continued

| Compound | Final dose (μg/ml) | % inhibition of NF-κB | Rating |
|---|---|---|---|
| HI-12 | 10 | none | none |
| | 50 | none | |
| | 100 | 49% | |

Code:
* low activity (20-30%);
** medium activity (31-55%);
*** high activity (56-75%),
**** very high activity (>76%)

Example 21

The effect of the compounds of EXAMPLE 20 on induction of elastin and collagen 1A was evaluated by an assay. Higher elastin and collagen activity is indicative of anti-wrinkling or anti-aging effects. Activation of the antioxidant response element (ARE) pathway was also evaluated. The NF-E2-related factor (Nrf2) is a critical transcription factor in oxidative stress signaling. Nrf2 binds to the ARE and serves as a master regulator in cellular defense pathways. The ARE pathway mediates the transcriptional induction of a battery of genes that help to protect the cells against oxidative damage. Activation of the ARE promoter leads to more endogenous antioxidants and cell detoxification. The results of the assay using different dosages of each of the compounds are provided in TABLE 9.

TABLE 9

| Compound | Final dose (μg/ml) | Elastin | Collagen 1A | ARE | Rating |
|---|---|---|---|---|---|
| HI-1 | 10 | 1.5x | 1.5x | — | **, **, N/A |
| | 50 | 2x | 3x | 3x | |
| | 100 | — | — | 5x | |

TABLE 9-continued

| Compound | Final dose (μg/ml) | Elastin | Collagen 1A | ARE | Rating |
|---|---|---|---|---|---|
| HI-2 | 10 | 1.5x | — | — | none |
|  | 50 | — | — | — |  |
|  | 100 | — | — | 1.7x |  |
| HI-3 | 10 | — | — | — | none |
|  | 50 | 4x | — | — |  |
|  | 100 | 2.8x | — | — |  |
| HI-4 | 10 | 2x | 2x | 2x | ****, ****, **** |
|  | 50 | 2x | — | — |  |
|  | 100 | — | — | — |  |
| HI-5 | 10 | 1.5x | — | 2x | **, *, **** |
|  | 50 | — | — | 2x |  |
|  | 100 | 1.5x | 1.3x | 2x |  |
| HI-6 | 10 | — | — | — | none, none, N/A |
|  | 50 | — | — | — |  |
|  | 100 | 2x | — | — |  |
| HI-7 | 10 | 3x | 3x | 2x | ****, ****, **** |
|  | 50 | 2x | — | 1.5x |  |
|  | 100 | — | — | — |  |
| HI-8 | 10 | — | — | — | *, none, none |
|  | 50 | 3x | — | — |  |
|  | 100 | 2.8x | — | — |  |
| HI-9 | 10 | — | 1.6x | — | none, ***, none |
|  | 50 | 2x | — | — |  |
|  | 100 | 4x | — | — |  |
| HI-10 | 10 | 1.7x | 1.4x | 2x | ***, **, **** |
|  | 50 | 1.8x | — | — |  |
|  | 100 | 4x | — | — |  |
| HI-11 | 10 | 1.8x | 2x | 1.5x | ****, ****, **** |
|  | 50 | — | — | 5x |  |
|  | 100 | — | — | 2x |  |
| HI-12 | 10 | 2x | — | — | ****, none, none |
|  | 50 | — | — | — |  |
|  | 100 | 2x | — | — |  |

Code:
* low activity (20-30%);
** medium activity (31-55%);
*** high activity (56-75%),
**** very high activity (>76%).
The dash (—) indicates <1.3x or no induction.

Example 22

The effect of the compounds of EXAMPLE 20 on inhibition of the production of reactive oxygen species (ROS), which can damage skin cells, was evaluated. The results of the assay using different dosages of each of the compounds are provided in TABLE 10.

TABLE 10

| Compound | Final dose (μg/ml) | % inhibition of UV-induced ROS |
|---|---|---|
| HI-1 | 10 | >70% |
| HI-2 | 10 | >70% |
| HI-3 | 10 | ~10% |
| HI-4 | 10 | >70% |
| HI-5 | 10 | ~25% |
| HI-6 | 10 | >70% |
| HI-7 | 10 | ~50% |
| HI-8 | 10 | >70% |
| HI-9 | 10 | >70% |
| HI-10 | 10 | ~50% |
| HI-11 | 10 | >70% |
| HI-12 | 10 | ~50% |

Example 23

The effect of the compounds of EXAMPLE 20 on inhibition of the secretion of inflammatory cytokines from human peripheral blood mononuclear cells (PBMCs) was evaluated. Upon stimulation with phytohemagglutinin (PHA), mature T cells respond by clonal expansion and the secretion of cytokines. Samples were evaluated to assess their ability to inhibit the activation of PHA-stimulated PBMCs. IL-2, IL-4, IFN-γ and TNF-α levels were assessed after treatment with each compound. Most of the 12 compounds showed good inhibition of these cytokines at 100 μg/mL dose.

Clause 1: A method for treating a skin cancer condition, the method comprising administering a therapeutically effective amount of a p53-related protein kinase (PRPK) inhibitor to a patient having skin cancer or having a high risk of developing skin cancer.

Clause 2: The method of clause 1, wherein the skin cancer condition comprises one or more of actinic keratosis, squamous cell carcinoma, or basal cell carcinoma.

Clause 3: The method of clause 1 or 2, wherein the skin cancer condition is associated with T-LAK cell-originated protein kinase (TOPK)-dependent PRPK phosphorylation.

Clause 4: The method of any of clauses 1 to 3, further comprising comparing the concentration of phosphorylated PRPK (p-PRPK) in a first biological sample of the patient obtained prior to the administration of the PRPK inhibitor and in a second biological sample of the patient obtained after the administration of the PRPK inhibitor.

Clause 5: The method of clause 4, wherein a lower concentration of p-PRPK in the second biological sample compared to the concentration of p-PRPK in the first biological sample is indicative of inhibition of PRPK phosphorylation by the PRPK inhibitor.

Clause 6: The method of clause 4 or 5, further comprising adjusting a dosage of the PRPK inhibitor administered to the patient based on the comparison.

Clause 7: The method of any of clauses 1 to 6, wherein the patient is administered at least 0.1 mg/day, 1 mg/day, 5 mg/day, 10 mg/day, 20 mg/day, 50 mg/day, or 100 mg/day of the PRPK inhibitor.

Clause 8: The method of any of clauses 1 to 7, wherein the PRPK inhibitor comprises one or both of rocuronium bromide or betamethasone 17-valerate, or analogs thereof.

Clause 9: The method of any of clauses 1 to 8, wherein the administering the PRPK inhibitor comprises administering a pharmaceutically acceptable carrier including the PRPK inhibitor to the patient.

Clause 10: The method of clause 9, wherein the pharmaceutically acceptable carrier comprises a topical formulation including the PRPK inhibitor.

Clause 11: The method of any of clauses 1 to 10, further comprising administering at least another treatment comprising one or more of chemotherapy, immunotherapy, radiation therapy, DNA therapy, RNA therapy, nanotherapy, adjuvant therapy, viral therapy, photodynamic therapy, electrocautery, laser therapy, or surgery.

Clause 12: The method of any of clauses 1 to 11, wherein a therapeutic effect is obtained by administering the PRPK inhibitor, wherein the therapeutic effect comprises one or more of: a reduction or a stability in one or more of an average volume of lesions, an average number of lesions, an average volume of tumors, an average number of tumors, or partial remission, complete remission, or metastasis.

Clause 13: A composition comprising a therapeutically effective amount of a PRPK inhibitor for treating a skin cancer condition.

Clause 14: The composition of clause 13, wherein the skin cancer condition comprises one or more of actinic keratosis, squamous cell carcinoma, or basal cell carcinoma.

Clause 15: The composition of clause 13 or 14, wherein the PRPK inhibitor comprises one or more of a steroid, a steroid derivative, a corticosteroid, or a gonane derivative.

Clause 16: The composition of any of clauses 13 to 15, wherein the PRPK inhibitor comprises one or both of rocuronium bromide or betamethasone 17-valerate, or analogs thereof.

Clause 17: The composition of any of clauses 13 to 15, wherein the PRPK inhibitor comprises at least one compound having the structure:

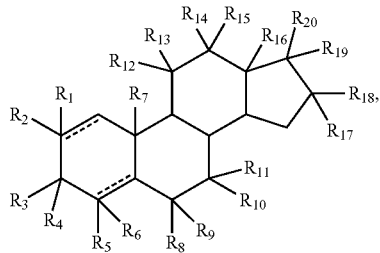

where any of $R_1$ to $R_{16}$=any of H, halo, hydroxy, substituted hydroxy, amino, substituted (acyl, alkyl, aralkyl, heteroaryl, cycloalkyl, aryl) amino, or carbonyl; any of $R_{17}$ or $R_{18}$=any of H, halo, hydroxy, substituted hydroxy, amino, substituted (acyl, alkyl, aralkyl, heteroaryl, cycloalkyl, aryl) amino, or quaternary ammonium group; any of $R_{19}$ or $R_{20}$=H, halo, hydroxy, substituted hydroxy, amino, or substituted (acyl, alkyl, aralkyl, heteroaryl, cycloalkyl, aryl) amino, or

wherein Q=H, allyl, substituted alkyl, aryl, substituted aryl, heteroaryl, substituted heteroaryl, hydroxy, substituted hydroxy, amino, substituted (acyl, alkyl, aralkyl, heteroaryl, cycloalkyl, aryl) amino, alkanol, alkenyl, or substituted alkenyl.

Clause 18: The composition of clause 17, wherein each of $R_2$, $R_4$, $R_5$, $R_6$, $R_7$, $R_8$, $R_9$, $R_{10}$, $R_{11}$, $R_{12}$, $R_{14}$, $R_{15}$, and $R_{18}$=H, wherein any of $R_1$, $R_3$, $R_7$, $R_{13}$, $R_{16}$, $R_{17}$, or $R_{20}$=any of H, allyl, substituted alkyl, aryl, substituted aryl, heteroaryl, substituted heteroaryl, sulfonyl, halo, hydroxy, substituted hydroxy, amino, dialkylamino, substituted (acyl, alkyl, aralkyl, heteroaryl, cycloalkyl, aryl) amino, carbonyl, substituted quarternary amino, O-glycosylated, alkenyl, substituted alkenyl, alkynyl, or substituted alkynyl, and wherein

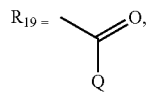

wherein Q=H, allyl, substituted alkyl, aryl, substituted aryl, heteroaryl, substituted heteroaryl, hydroxy, substituted hydroxy, amino, substituted (acyl, alkyl, aralkyl, heteroaryl, cycloalkyl, aryl) amino, alkanol, alkenyl, or substituted alkenyl.

Clause 19. The composition of any of clauses 13 to 18, wherein the composition comprises 0.01%, 0.1%, 1%, 2%, 5%, or 10% (weight/weight) of the PRPK inhibitor.

Clause 20. A topical formulation comprising the composition of any of clauses 13 to 19.

Clause 21. A composition comprising a pharmaceutically effective amount of at least one anti-solar ultraviolet (anti-sUV) combination for preventing a skin cancer condition, wherein the at least one anti-sUV combination is chosen from the combinations:
avobenzone and octinoxate,
octocrylene and zinc oxide,
avobenzone, octocrylene, and titanium dioxide, or
avobenzone, octocrylene, and zinc oxide.

Clause 22: The composition of clause 21, wherein the at least one anti-sUV combination is chosen from the combinations:
3% (weight/weight) avobenzone and 7.5% (weight/weight) octinoxate,
7% (weight/weight) octocrylene and 6.9% (weight/weight) zinc oxide, or
3% (weight/weight) avobenzone, 7% (weight/weight) octocrylene, and 6% (weight/weight) titanium dioxide,
wherein the respective concentrations are with reference to a total weight of the composition.

Clause 23: The composition of clause 21 or 22, wherein the pharmaceutically effective amount of the at least one anti-sUV combination has an anti-sUV effectiveness of at least 95% against the skin cancer condition, wherein the anti-sUV effectiveness is a percentage reduction in average tumor volume.

Clause 24: The composition of clause 23, wherein the anti-sUV effectiveness is at least 99%.

Clause 25: The composition of any of clauses 21 to 24, further comprising at least one anti-sUV agent chosen from avobenzone, octocrylene, oxybenzone, octinoxate, octisalate, titanium dioxide, zinc oxide, or homosalate.

Clause 26: The composition of any of clauses 21 to 25, wherein the skin cancer condition comprises one or more of actinic keratosis, squamous cell carcinoma, or basal cell carcinoma.

Clause 27: The composition of any of clauses 21 to 26, comprising a pharmaceutically acceptable carrier.

Clause 28: The composition of clause 27, wherein the pharmaceutically acceptable carrier comprises one or more of a cream, a lotion, a spray, a gel, an ointment, a paste, a solution, a suspension, an emulsion, a powder, a liquid, or a solid.

Clause 29: The composition of any of clauses 21 to 28, comprising the composition of any of clauses 13 to 20.

Clause 30: A topical formulation comprising the composition of any of clauses 21 to 28.

Clause 31: A composition comprising at least one of a first phase or a second phase, wherein the first phase comprises 1,3-butylene glycol, glycerin, pentylene glycol, a salt of ethylenediaminetetraacetic acid (EDTA), and water, and wherein the second phase comprises cetyl alcohol, glyceryl stearate, and hydrogenated polydecene.

Clause 32: The composition of clause 31, comprising both the first phase and the second phase.

Clause 33: The composition of clause 31 or 32, wherein the salt of EDTA comprises one or more of calcium disodium EDTA, diammonium EDTA, dipotassium EDTA, disodium EDTA, triethanolamine EDTA (TEA-EDTA), tetrasodium EDTA, tripotassium EDTA, trisodium EDTA, hydroxyethyl ethylenediamine triacetic acid (HEDTA), or trisodium HEDTA.

Clause 34: The composition of any of clauses 31 to 33, wherein the composition is substantially free of one or more allergenic preservatives.

Clause 35: The composition of clause 34, wherein the one or more allergenic preservatives comprise one or more of benzyl alcohol, phenoxyethanol, sorbic acid, benzoic acid, chlorphenesin, dehydroacetic acid, salicylic acid, methylparaben, ethylparaben, propylparaben, isobutylparaben, butylparaben, imidazolidinyl urea, or diazolidinyl urea.

Clause 36: The composition of any of clauses 31 to 35, wherein the composition comprises an oil in water emulsion, wherein the oil in water emulsion comprises the first phase and the second phase.

Clause 37: The composition of any of clauses 31 to 36, consisting essentially of 1,3-butylene glycol, glycerin, pentylene glycol, a salt of ethylenediaminetetraacetic acid (EDTA), water, cetyl alcohol, glyceryl stearate, and hydrogenated polydecene.

Clause 38: The composition of any of clauses 31 to 37, wherein the first phase comprises 0.01% to 0.05% (weight/volume) salt of EDTA, 4% to 6% (volume/volume) 1,3-butylene glycol, 5% to 10% (volume/volume) glycerin, 1.3% to 3.0% (volume/volume) pentylene glycol, and 81% to 90% (volume/volume) water, and wherein the second phase comprises 10% to 25% (weight/volume) cetyl alcohol, 10% to 25% (weight/volume) glyceryl stearate, and 50% to 80% (volume/volume) hydrogenated polydecene.

Clause 39: The composition of any of clauses 31 to 38, wherein the composition has a pH in a range from 6.8 to 7.5.

Clause 40: The composition of any of clauses 31 to 39, further comprising one or more anti-wrinkling or anti-aging compounds chosen from 7,3,4'-trihydroxyisoflavone, delphiniden, magnolol, 6,7,4'-trihydroxyisoflavone, naringenin, caffeic acid phenylethyl ester (CAPE), 3,7,4'-trihydroxyflavone, myricetin, quercetagetin, isorhamnetin, luteolin, or herbacetin.

Clause 41: The composition of any of clauses 31 to 40, further comprising one or more skin lightning agents chosen from hydroquinone (also known as benzene-1,4-diol or quinol), alpha arbutin (bearberry bush leaf extract), resveratrol (3,5,4'-trihydroxy-trans-stilbene), or sepicalm-S.

Clause 42: The composition of any of clauses 31 to 41, comprising the composition of any of clauses 13 to 29.

Clause 43: A formulation comprising the composition of any of clauses 31 to 42, wherein the formulation is a topical skin care formulation capable of being applied to skin.

Clause 44: The formulation of clause 43, wherein the formulation is noncarcinogenic.

Clause 45: The formulation of clause 44, wherein the formulation does not increase the incidence of average number of papillomas on the skin on exposure for a predetermined period of time to predetermined ultraviolet wavelengths.

Clause 46: A method comprising:
agitating a first phase comprising 1,3-butylene glycol, glycerin, pentylene glycol, a salt of ethylenediaminetetraacetic acid (EDTA), and water; and
forming a composition by introducing a second phase into the first phase during the agitating, wherein the second phase comprises cetyl alcohol, glyceryl stearate, and hydrogenated polydecene.

Clause 47: The method of clause 46, wherein the agitating comprises stirring the first phase and the second phase by a rotation of 1500 to 2000 rotations per minute (rpm).

Clause 48: The method of clause 47, further comprising increasing the agitation by increasing the rotation to 3000 to 3500 rpm.

Clause 49: The method of clause 48, further comprising reducing the agitation by reducing the agitation to 1500 to 2000 rpm.

Clause 50: The method of any of clauses 46 to 49, comprising maintaining a temperature of one or more of the first phase, the second phase, or the composition at about 70° C. for a predetermined period of time.

Clause 51: The method of clause 50, further comprising cooling the composition or allowing the composition to cool to a temperature of about 45° C. during the agitating.

Clause 52: The method of clause 50 or 51, further comprising cooling the composition or allowing the composition to cool to a temperature of about 30° C. during the agitating.

Clause 53: The method of any of clauses 46 to 52, wherein forming the composition comprises emulsifying the second phase into the first phase to form an oil in water emulsion.

Various examples have been described. These and other examples are within the scope of the following claims.

What is claimed is:

1. A method for treating a skin condition, the method comprising administering a composition comprising a therapeutically effective amount of a p53-related protein kinase (PRPK) inhibitor to a patient having skin cancer or having a high risk of developing skin cancer, wherein the composition comprises 0.1% to 1% (weight/volume) of the PRPK inhibitor, and wherein the PRPK inhibitor comprises rocuronium bromide or analogs thereof.

2. The method of claim 1, wherein the skin cancer condition comprises one or more of actinic keratosis, squamous cell carcinoma, or basal cell carcinoma.

3. The method of claim 1, wherein the skin cancer condition is associated with T-LAK cell-originated protein kinase (TOPK)-dependent PRPK phosphorylation.

4. The method of claim 1, further comprising comparing the concentration of phosphorylated PRPK (p-PRPK) in a first biological sample of the patient obtained prior to the administration of the PRPK inhibitor and in a second biological sample of the patient obtained after the administration of the PRPK inhibitor.

5. The method of claim 4, wherein a lower concentration of p-PRPK in the second biological sample compared to the concentration of p-PRPK in the first biological sample is indicative of inhibition of PRPK phosphorylation by the PRPK inhibitor.

6. The method of claim 4, further comprising adjusting a dosage of the PRPK inhibitor administered to the patient based on the comparison.

7. The method of claim 1, wherein the patient is administered at least 0.1 mg/day, 1 mg/day, 5 mg/day, 10 mg/day, 20 mg/day, 50 mg/day, or 100 mg/day of the PRPK inhibitor.

8. The method of claim 1, wherein the PRPK inhibitor comprises the rocuronium bromide and betamethasone 17-valerate, or analogs thereof.

9. The method of claim 1, wherein the administering the PRPK inhibitor comprises administering a pharmaceutically acceptable carrier including the PRPK inhibitor to the patient.

10. The method of claim 9, wherein the pharmaceutically acceptable carrier comprises a topical formulation including the PRPK inhibitor.

11. The method of claim 1, further comprising administering at least another treatment comprising one or more of chemotherapy, immunotherapy, radiation therapy, DNA therapy, RNA therapy, nanotherapy, adjuvant therapy, viral therapy, photodynamic therapy, electrocautery, laser therapy, or surgery.

12. The method of claim 1, wherein a therapeutic effect is obtained by administering the PRPK inhibitor, wherein the therapeutic effect comprises one or more of: a reduction or a stability in one or more of an average volume of lesions, an average number of lesions, an average volume of tumors, an average number of tumors, or partial remission, complete remission, or metastasis.

13. The method of claim 1, wherein the skin condition comprises actinic keratosis.

14. The method of claim 1, wherein the skin condition comprises precursor condition to cutaneous squamous cell carcinoma.

15. The method of claim 1, wherein administering the composition comprising the therapeutically effective amount of the PRPK inhibitor to the patient comprises administering a lotion comprising the therapeutically effective amount of the PRPK inhibitor to the patient.

16. A method for treating a skin condition, the method comprising administering a composition comprising a therapeutically effective amount of a p53-related protein kinase (PRPK) inhibitor to a patient having actinic keratosis, wherein the composition comprises 0.1% to 1% (weight/volume) of the PRPK inhibitor, and wherein the PRPK inhibitor comprises rocuronium bromide or analogs thereof.

17. The method of claim 16, wherein administering the composition comprising the therapeutically effective amount of the PRPK inhibitor to the patient comprises administering a lotion comprising the therapeutically effective amount of the PRPK inhibitor to the patient.

18. The method of claim 17, wherein the lotion comprises a salt of ethylenediamine tetra-acetic acid, 1,3-butylene glycol, glycerin, pentylene glycol, cetyl alcohol, glyceryl stearate, and hydrogenated polydecene.

19. The method of claim 1, wherein the composition comprises an oil in water emulsion.

20. The method of claim 19, wherein the oil in water emulsion comprises a salt of ethylenediamine tetra-acetic acid, 1,3-butylene glycol, glycerin, pentylene glycol, cetyl alcohol, glyceryl stearate, and hydrogenated polydecene.

* * * * *